United States Patent
Anryu et al.

(10) Patent No.: US 10,431,760 B2
(45) Date of Patent: Oct. 1, 2019

(54) LIGHT EMITTING DEVICE

(71) Applicant: Sumitomo Chemical Company, Limited, Tokyo (JP)

(72) Inventors: Makoto Anryu, Osaka (JP); Nobuhiko Akino, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 44 days.

(21) Appl. No.: 15/315,110

(22) PCT Filed: May 22, 2015

(86) PCT No.: PCT/JP2015/064766
§ 371 (c)(1),
(2) Date: Nov. 30, 2016

(87) PCT Pub. No.: WO2015/186539
PCT Pub. Date: Dec. 10, 2015

(65) Prior Publication Data
US 2017/0194584 A1 Jul. 6, 2017

(30) Foreign Application Priority Data

Jun. 4, 2014 (JP) .................................. 2014-115533
Dec. 25, 2014 (JP) .................................. 2014-262000

(51) Int. Cl.
*H01L 51/54* (2006.01)
*C09K 11/06* (2006.01)
*H01L 51/50* (2006.01)
*H01L 51/00* (2006.01)
*C07F 15/00* (2006.01)
*C08G 61/12* (2006.01)

(52) U.S. Cl.
CPC .............. *H01L 51/50* (2013.01); *C07F 15/00* (2013.01); *C08G 61/12* (2013.01); *C09K 11/06* (2013.01); *H01L 51/0043* (2013.01); *H01L 51/0085* (2013.01); *H01L 51/504* (2013.01); *H01L 51/5016* (2013.01); *H01L 51/5036* (2013.01); *C09K 2211/1029* (2013.01); *C09K 2211/185* (2013.01)

(58) Field of Classification Search
None
See application file for complete search history.

(56) References Cited

U.S. PATENT DOCUMENTS

| | | |
|---|---|---|
| 2009/0212693 A1 | 8/2009 | Yamada |
| 2010/0073602 A1 | 3/2010 | Akino |
| 2010/0207105 A1 | 8/2010 | Katakura et al. |
| 2011/0114926 A1 | 5/2011 | Okabe et al. |
| 2011/0215309 A1 | 9/2011 | D'Andrade et al. |
| 2012/0199825 A1 | 8/2012 | Soga et al. |
| 2014/0027751 A1 * | 1/2014 | Furukawa et al. ..... C09K 11/06 257/40 |
| 2014/0070180 A1 | 3/2014 | Choi et al. |
| 2014/0197399 A1 | 7/2014 | Taka |
| 2014/0361274 A1 | 12/2014 | King et al. |

(Continued)

FOREIGN PATENT DOCUMENTS

| | | |
|---|---|---|
| CN | 102203977 A | 9/2011 |
| EP | 1995292 A1 | 11/2008 |

(Continued)

OTHER PUBLICATIONS

Office Action dated Sep. 4, 2017 in CN Application No. 201580029549.6, with English Translation.
Office Action dated May 28, 2015 in JP Application No. 2014-262000.
Office Action dated Sep. 11, 2015 in JP Application No. 2014-262000.
Extended Search Report dated Nov. 8, 2017 in EP Application No. 15803761.
Second Office Action dated May 21, 2018 in CN Application No. 201580029549.6.
Office Action dated Oct. 31, 2018 in TW Application No. 104117748.6.
Office Action dated Dec. 24, 2018 in CN Application No. 201580029549.6.

*Primary Examiner* — Marie R. Yamnitzky
(74) *Attorney, Agent, or Firm* — Panitch Schwarze Belisario & Nadel LLP

(57) ABSTRACT

A light emitting device excellent in luminance life includes an anode, a cathode, a first organic layer (containing at least one phosphorescent compound) disposed between the anode and cathode and a second organic layer (containing at least one phosphorescent compound and a crosslinked body) disposed between the anode and first organic layer. At least one phosphorescent compound contained in the first and second organic layers is the same phosphorescent compound and is represented by the formula (1):

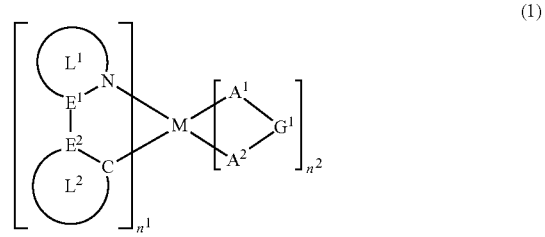

(1)

wherein M may be an iridium atom, $n^1$ represents an integer of 1 or more, $n^2$ may be 0 or more, $E^1$ and $E^2$ may be a carbon atom, ring $L^1$ represents an aromatic heterocyclic ring, ring $L^2$ may be an aromatic hydrocarbon ring, $A^1$-$G^1$-$A^2$ represents an anionic bidentate ligand, and at least one of rings $L^1$ and $L^2$ has an aryl group, a monovalent heterocyclic group or a substituted amino group.

7 Claims, No Drawings

(56) References Cited

U.S. PATENT DOCUMENTS

2014/0374727 A1    12/2014    Akino et al.
2015/0014669 A1    1/2015    Akino et al.

FOREIGN PATENT DOCUMENTS

| | | |
|---|---|---|
| JP | 200898619 A | 4/2008 |
| JP | 2008147425 A | 6/2008 |
| JP | 2008-174499 A | 7/2008 |
| JP | 2008218987 A | 9/2008 |
| JP | 2009152435 A | 7/2009 |
| JP | 2012-502485 A | 1/2012 |
| JP | 201228726 A | 2/2012 |
| JP | 201236388 A | 2/2012 |
| JP | 2013147449 A | 8/2013 |
| JP | 2013147450 A | 8/2013 |
| JP | 201429875 A | 2/2014 |
| JP | 2014239219 A | 12/2014 |
| TW | 201313774 A | 4/2013 |
| WO | 02071813 A1 | 9/2002 |
| WO | 2008101842 A1 | 8/2008 |
| WO | 2008146838 A1 | 12/2008 |
| WO | 2010028262 A1 | 3/2010 |
| WO | 2011132550 A1 | 10/2011 |
| WO | WO 2012/137640 A1 * | 10/2012 |
| WO | 2013005031 A1 | 1/2013 |
| WO | 2013021180 A1 | 2/2013 |
| WO | 2013027711 A1 | 2/2013 |
| WO | 2013108037 A1 | 7/2013 |
| WO | 2013164647 A2 | 11/2013 |

* cited by examiner

LIGHT EMITTING DEVICE

CROSS-REFERENCE TO RELATED APPLICATION

This application is a Section 371 of International Application No. PCT/JP2015/064766, filed May 22, 2015, which was published in the Japanese language on Dec. 10, 2015, under International Publication No. WO 2015/186539 A1, and the disclosure of which is incorporated herein by reference.

TECHNICAL FIELD

The present invention relates to a light emitting device.

BACKGROUND ART

Light emitting devices such as an organic electroluminescent device (organic EL device) can be suitably used for applications of displays and illumination because of properties such as high light emission efficiency and driving at low voltage, and are recently attracting attention. This light emitting device comprises organic layers such as a light emitting layer and a charge transporting layer.

Patent document 1 discloses a light emitting device comprising a light emitting layer formed by using a phosphorescent compound and a hole transporting layer formed by using a polymer compound comprising a fluorene constitutional unit, an aromatic amine constitutional unit and a crosslinkable constitutional unit. For formation of a hole transporting layer, only a polymer compound comprising a fluorene constitutional unit, an aromatic amine constitutional unit and a crosslinkable constitutional unit is used.

PRIOR ART DOCUMENT

Patent Document

[Patent document 1] JP-A No. 2012-036388

SUMMARY OF THE INVENTION

Problem to be Solved by the Invention

The above-described light emitting device disclosed in Patent document 1, however, does not necessarily have sufficient luminance life.

Then, the present invention has an object of providing a light emitting device excellent in luminance life.

Means for Solving the Problem

The present invention provides the following [1] to [10].

[1] A light emitting device comprising an anode, a cathode, a first organic layer disposed between the anode and the cathode and a second organic layer disposed between the anode and the first organic layer, wherein the first organic layer is a layer comprising one or more phosphorescent compounds, the second organic layer is a layer comprising one or more phosphorescent compounds and a crosslinked body of a crosslinkable material, and at least one phosphorescent compound contained in the first organic layer and at least one phosphorescent compound contained in the second organic layer are the same phosphorescent compound represented by the formula (1):

[Chemical formula 1]

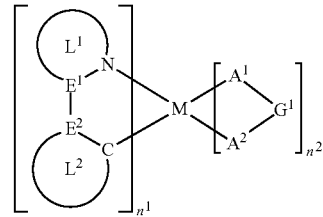

(1)

[wherein,

M represents a ruthenium atom, a rhodium atom, a palladium atom, an iridium atom or a platinum atom.

$n^1$ represents an integer of 1 or more, $n^2$ represents an integer of C or more, and $n^1+n^2$ is 2 or 3. $n^1+n^2$ is 3 when M is a ruthenium atom, a rhodium atom or an iridium atom, while $n^1+n^2$ is 2 when M is a palladium atom or a platinum atom.

$E^1$ and $E^2$ each independently represent a carbon atom or a nitrogen atom. At least one of $E^1$ and $E^2$ is a carbon atom.

The ring $L^1$ represents a 5-membered or 6-membered aromatic heterocyclic ring, and the ring optionally has a substituent. When a plurality of the substituents are present, they may be the same or different and may be combined together to form a ring together with the atoms to which they are attached. When a plurality of the rings $L^1$ are present, they may be the same or different. $E^1$ is a carbon atom when the ring $L^1$ is a 6-membered aromatic heterocyclic ring.

The ring $L^2$ represents a 5-membered or 6-membered aromatic hydrocarbon ring or a 5-membered or 6-membered aromatic heterocyclic ring, and these rings each optionally have a substituent. When a plurality of the substituents are present, they may be the same or different and may be combined together to form a ring together with the atoms to which they are attached. When a plurality of the rings $L^2$ are present, they may be the same or different. $E^2$ is a carbon atom when the ring $L^2$ is a 6-membered aromatic heterocyclic ring.

At least one ring selected from the group consisting of the ring $L^1$ and the ring $L^2$ has a group represented by the formula (2).

$A^1$-$G^1$-$A^2$ represents an anionic bidentate ligand. $A^1$ and $A^2$ each independently represent a carbon atom, an oxygen atom or a nitrogen atom, and these atoms each may be an atom constituting the ring. $G^1$ represents a single bond or an atomic group constituting the bidentate ligand together with $A^1$ and $A^2$. When a plurality of $A^1$-$G^1$-$A^2$ are present, they may be the same or different.]

$$—R^2 \qquad (2)$$

[wherein, $R^2$ represents an aryl group, a monovalent heterocyclic group or a substituted amino group, and these groups each optionally have a substituent.].

[2] The light emitting device according to [1], wherein the group represented by the formula (2) is a group represented by the formula (D-A) or a group represented by the formula (D-B):

[Chemical formula 2]

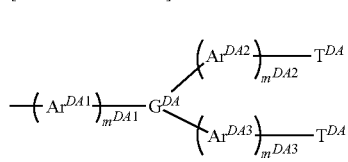
(D-A)

[wherein, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, and these groups each optionally have a substituent.

$Ar^{DA1}$, $Ar^{DA2}$ and $Ar^{DA3}$ each independently represent an arylene group or a divalent heterocyclic group, and these groups each optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and these groups each optionally have a substituent. The plurality of $T^{DA}$ may be the same or different.]

[Chemical formula 3]

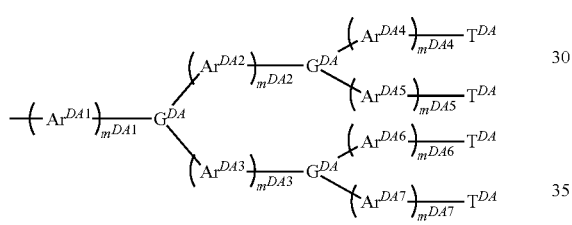
(D-B)

[wherein, $m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents a nitrogen atom, an aromatic hydrocarbon group or a heterocyclic group, and these groups each optionally have a substituent. The plurality of $G^{DA}$ may be the same or different.

$Ar^{DA1}$, $Ar^{DA2}$, $Ar^{DA3}$, $A^{DA4}$, $Ar^{DA5}$, $Ar^{DA6}$, and $Ar^{DA7}$ each independently represent an arylene group or a divalent heterocyclic group, and these groups each optionally have a substituent. When a plurality of $Ar^{DA1}$, $Ar^{DA2}$, $Ar^{DA3}$, $A^{DA4}$, $Ar^{DA5}$, $Ar^{DA6}$, and $Ar^{DA7}$ are present, they may be the same or different at each occurrence.

$T^{DA}$ represents an aryl group or a monovalent heterocyclic group, and these groups each optionally have a substituent. The plurality of $T^{DA}$ may be the same or different.].

[3] The light emitting device according to [1] or [2], wherein the crosslinkable material is a polymer compound comprising a crosslinkable constitutional unit having at least one crosslinkable group selected from Group A of crosslinkable group:

(Group A of crosslinkable group)

[Chemical formula 4]

(XL-1)

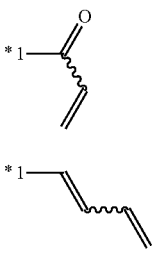
(XL-2)

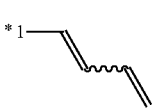
(XL-3)

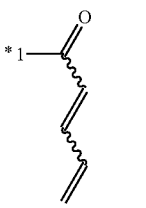
(XL-4)

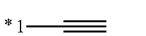
(XL-5)

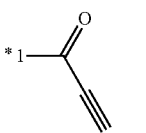
(XL-6)

(XL-7)

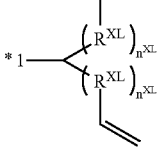
(XL-8)

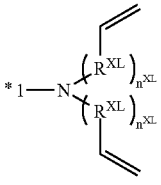
(XL-9)

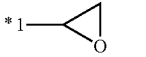
(XL-10)

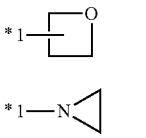
(XL-11)

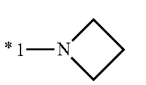
(XL-12)

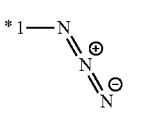
(XL-13)

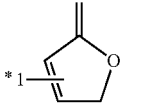
(XL-14)

-continued

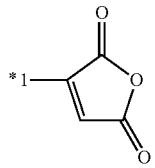
(XL-15)

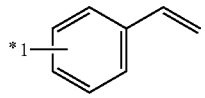
(XL-16)

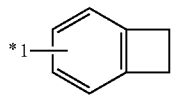
(XL-17)

[wherein, $R^{XL}$ represents a methylene group, an oxygen atom or a sulfur group, and $n^{XL}$ represents an integer of 0 to 5. When a plurality of $R^{XL}$ are present, they may be the same or different, and when a plurality of $n^{XL}$ are present, they may be the same or different. *1 represents a binding site. These crosslinkable groups each optionally have a substituent.).

[4] The light emitting device according to [3], wherein the crosslinkable constitutional unit is a constitutional unit represented by the formula (3) or a constitutional unit represented by the formula (4):

[Chemical formula 5]

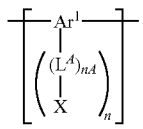
(3)

[wherein, nA represents an integer of 0 to 5, and n represents 1 or 2.

$Ar^1$ represents an aromatic hydrocarbon group or a heterocyclic group, and these groups each optionally have a substituent.

$L^A$ represents an alkylene group, a cycloalkylene group, an arylene group, a divalent heterocyclic group, a group represented by —NR'—, an oxygen atom or a sulfur atom, and these groups each optionally have a substituent. R' represents a hydrogen atom, an alkyl group, a cycloalkyl group, an aryl group or a monovalent heterocyclic group, and these groups each optionally have a substituent. When a plurality of $L^A$ are present, they may be the same or different.

X represents a crosslinkable group selected from Group A of crosslinkable group. When a plurality of X are present, they may be the same or different.]

[Chemical formula 6]

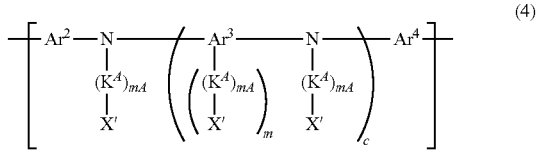
(4)

[wherein, mA represents an integer of 0 to 5, m represents an integer of 1 to 4, and c represents 0 or 1. When a plurality of mA are present, they may be the same or different.

$Ar^3$ represents an aromatic hydrocarbon group, a heterocyclic group or a group in which at least one aromatic hydrocarbon ring and at least one heterocyclic ring are bonded directly to each other, and these groups each optionally have a substituent.

$Ar^2$ and $Ar^4$ each independently represent an arylene group or a divalent heterocyclic group, and these groups each optionally have a substituent.

Each of $Ar^2$, $Ar^3$ and $Ar^4$ may be bonded directly or via an oxygen atom or a sulfur atom to a group that is different from that group and that is attached to the nitrogen atom to which that group is attached, thereby forming a ring.

$K^A$ represents an alkylene group, a cycloalkylene group, an arylene group, a divalent heterocyclic group, a group represented by —NR"—, an oxygen atom or a sulfur atom, and these groups each optionally have a substituent. R" represents a hydrogen atom, an alkyl group, a cycloalkyl group, an aryl group or a monovalent heterocyclic group, and these groups each optionally have a substituent. When a plurality of $K^A$ are present, they may be the same or different.

X' represents a crosslinkable group selected from Group A of crosslinkable group, a hydrogen atom, an alkyl group, a cycloalkyl group, an aryl group or a monovalent heterocyclic group, and these groups each optionally have a substituent. At least one X' is a crosslinkable group selected from Group A of crosslinkable group.].

[5] The light emitting device according to any one of [1] to [4], wherein the phosphorescent compound represented by the formula (1) is a phosphorescent compound represented by the formula (1-A):

[Chemical formula 7]

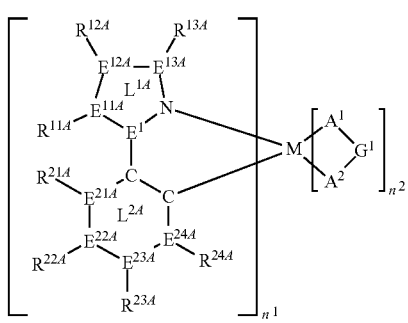
(1-A)

[wherein,

M, $n^1$, $n^2$, $E^1$ and $A^1$-$G^1$-$A^2$ represent the same meaning as described above.

$E^{11A}$, $E^{12A}$, $E^{13A}$, $E^{21A}$, $E^{22A}$, $E^{23A}$ and $E^{24A}$ each independently represent a nitrogen atom or a carbon atom. When a plurality of $E^{11A}$, $E^{12A}$, $E^{13A}$, $E^{21A}$, $E^{22A}$, $E^{23A}$ and $E^{24A}$ are present, they may be the same or different at each occurrence. $R^{11A}$, $R^{12A}$ and $R^{13A}$ may be either present or not present when $E^{11A}$, $E^{12A}$ and $E^{13A}$ are nitrogen atoms. $R^{21A}$, $R^{22A}$, $R^{23A}$ and $R^{24A}$ are not present when $E^{21A}$, $E^{22A}$, $E^{23A}$ and $E^{24A}$ are nitrogen atoms.

$R^{11A}$, $R^{12A}$, $R^{13A}$, $R^{21A}$, $R^{22A}$, $R^{23A}$ and $R^{24A}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. When a plurality of $R^{11A}$, $R^{12A}$, $R^{13A}$, $R^{21A}$, $R^{22A}$, $R^{23A}$ and $R^{24A}$ are present, they may be the same or different at each occurrence. $R^{11A}$ and $R^{12A}$, $R^{12A}$ and $R^{13A}$, $R^{11A}$ and $R^{21A}$, $R^{21A}$ and $R^{22A}$, $R^{22A}$ and $R^{23A}$, and $R^{23A}$ and $R^{24A}$ each may be combined together to form a ring together with the atoms to which they are attached. At least one selected from the group consisting of $R^{11A}$, $R^{12A}$, $R^{13A}$, $R^{21A}$, $R^{22A}$, $R^{23A}$ and $R^{24A}$ is a group represented by the formula (2).

The ring $L^{1A}$ represents a triazole ring or an imidazole ring constituted of a nitrogen atom, $E^1$, $E^{11A}$, $E^{12A}$ and $E^{13A}$.

The ring $L^{2A}$ represents a benzene ring, a pyridine ring or a pyrimidine ring constituted of two carbon atoms, $E^{21A}$, $E^{22A}$, $E^{23A}$ and $E^{24A}$.].

[6] The light emitting device according to [5], wherein the phosphorescent compound represented by the formula (1-A) is a phosphorescent compound represented by the formula (1-A1), (1-A2), (1-A3) or (1-A4):

[Chemical formula 8]

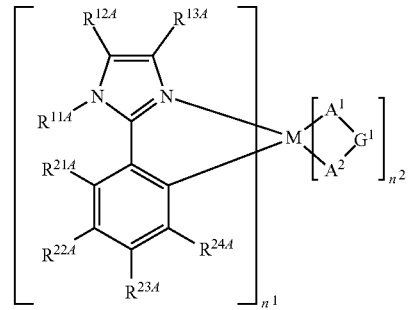

(1-A1)

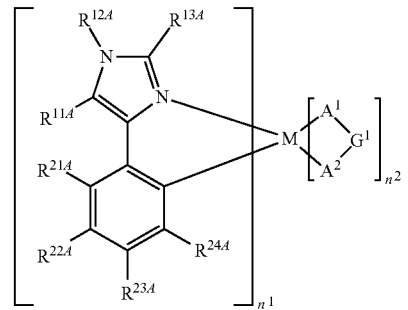

(1-A2)

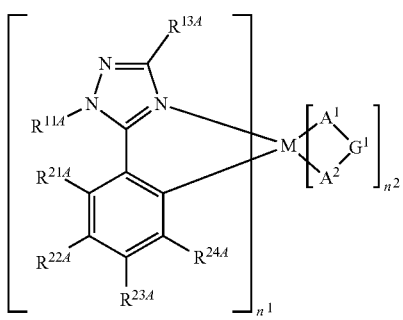

(1-A3)

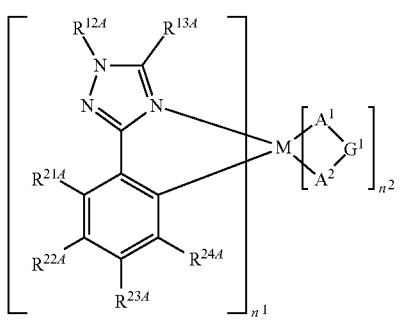

(1-A4)

[wherein,
M, $n^1$, $n^2$, $R^{11A}$, $R^{12A}$, $R^{13A}$, $R^{21A}$, $R^{22A}$, $R^{23A}$, $R^{24A}$ and $A^1$-$G^1$-$A^2$ represent the same meaning as described above.].

[7] The light emitting device according to any one of [1] to [4], wherein the phosphorescent compound represented by the formula (1) is a phosphorescent compound represented by the formula (1-B):

[Chemical formula 9]

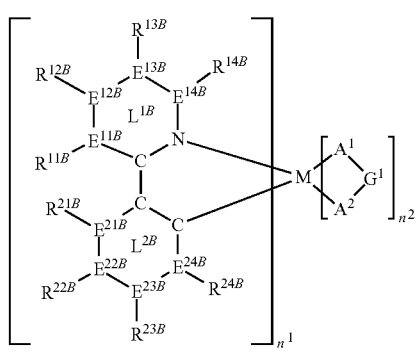

(1-B)

[wherein,
M, $n^1$, $n^2$ and $A^1$-$G^1$-$A^2$ represent the same meaning as described above.

$E^{11B}$, $E^{12B}$, $E^{13B}$, $E^{14B}$, $E^{21B}$, $E^{22B}$, $E^{23B}$ and $E^{24B}$ each independently represent a nitrogen atom or a carbon atom. When a plurality of $E^{11B}$, $E^{12B}$, $E^{13B}$, $E^{14B}$, $E^{21B}$, $E^{22B}$, $E^{23B}$ and $E^{24B}$ are present, they may be the same or different at each occurrence. $R^{11B}$, $R^{12B}$, $R^{13B}$, $R^{14B}$, $R^{21B}$, $R^{22B}$, $R^{23B}$ and $R^{24B}$ are not present when $E^{11B}$, $E^{12B}$, $E^{13B}$, $E^{14B}$, $E^{21B}$, $E^{22B}$, $E^{23B}$ and $E^{24B}$ are nitrogen atoms.

$R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups each optionally have a substituent. When a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence. $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ each may be combined together to form a ring together with the atoms to which they are attached. At least one selected from the group consisting of $R^{11B}$, $R^{12B}$, $R^{13B}$, $R^{14B}$, $R^{21B}$, $R^{22B}$, $R^{23B}$ and $R^{24B}$ is a group represented by the formula (2).

The ring $L^{1B}$ represents a pyridine ring or a pyrimidine ring constituted of a nitrogen atom, a carbon atom, $E^{11B}$, $E^{12B}$, $E^{13B}$ and $E^{14B}$.

The ring $L^{2B}$ represents a benzene ring, a pyridine ring or a pyrimidine ring constituted of two carbon atoms, $E^{21B}$, $E^{22B}$, $E^{23B}$ and $E^{24B}$.].

[8] The light emitting device according to [7], wherein the phosphorescent compound represented by the formula (1-B) is a phosphorescent compound represented by the formula (1-B1), (1-B2) or (1-B3):

[Chemical formula 10]

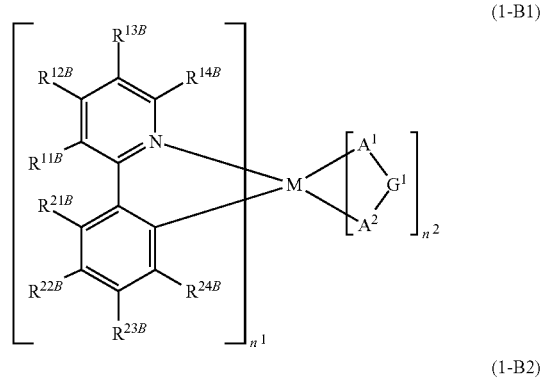

(1-B1)

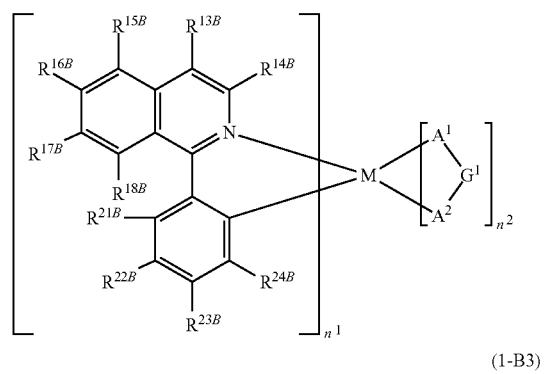

(1-B2)

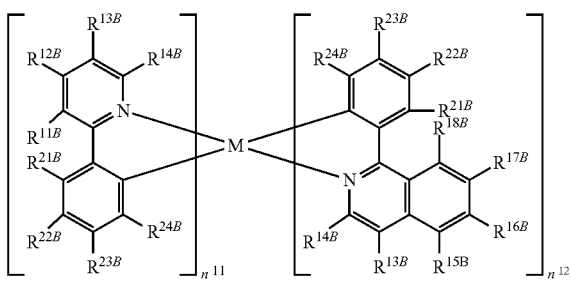

(1-B3)

[wherein,
M, $n^1$, $n^2$, $A^1$-$G^1$-$A^2$, $R^{11B}$, $R^{12B}$, $R^{13B}$, $R^{14B}$, $R^{21B}$, $R^{22B}$, $R^{23B}$ and $R^{24B}$ represent the same meaning as described above.

$n^{11}$ and $n^{12}$ each independently represent an integer of 1 or more, and $n^{11}+n^{12}$ is 2 or 3. $n^{11}+n^{12}$ is 3 when M is a ruthenium atom, a rhodium atom or an iridium atom, while $n^{11}+n^{12}$ is 2 when M is a palladium atom or a platinum atom.

$R^{15B}$, $R^{16B}$, $R^{17B}$ and $R^{18B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. When a plurality of $R^{15B}$, $R^{16B}$, $R^{17B}$ and $R^{18B}$ are present, they may be the same or different at each occurrence. $R^{13B}$ and $R^{15B}$, $R^{15B}$ and $R^{16B}$, $R^{16B}$ and $R^{17B}$, $R^{17B}$ and $R^{18B}$, and $R^{18B}$ and $R^{21B}$ each may be combined together to form a ring together with the atoms to which they are attached.

At least one selected from the group consisting of $R^{11B}$, $R^{12B}$, $R^{13B}$, $R^{14B}$, $R^{21B}$, $R^{22B}$, $R^{23B}$ and $R^{24B}$ is a group represented by the formula (2).].

[9] The light emitting device according to any one of [1] to [8], wherein the first organic layer is a layer comprising one or more phosphorescent compounds and a polymer compound comprising a constitutional unit represented by the formula (Y):

[Chemical formula 11]

 (Y)

[wherein, $Ar^{Y1}$ represents an arylene group, a divalent heterocyclic group or a divalent group in which at least one arylene group and at least one divalent heterocyclic group are bonded directly to each other, and these groups each optionally have a substituent.].

[10] The light emitting device according to any one of [1] to [8], wherein the first organic layer is a layer comprising one or more phosphorescent compounds and a compound represented by the formula (H-1):

[Chemical formula 12]

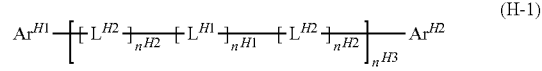 (H-1)

[wherein,
$Ar^{H1}$ and $Ar^{H2}$ each independently represent an aryl group or a monovalent heterocyclic group, and these groups each optionally have a substituent.

$n^{H1}$ and $n^{H2}$ each independently represent 0 or 1. When a plurality of $n^{H1}$ are present, they may be the same or different. The plurality of $n^{H2}$ may be the same or different. $n^{H3}$ represents an integer of 0 or more.

$L^{H1}$ represents an arylene group, a divalent heterocyclic group or a group represented by —[C($R^{H11}$)$_2$]$n^{H11}$-, and these groups each optionally have a substituent. When a plurality of $L^{H1}$ are present, they may be the same or different. $n^{H11}$ represents an integer of 1 to 10. $R^{H11}$ represents a hydrogen atom, an alkyl group, a cycloalkyl group, an alkoxy group, a cycloalkoxy group, an aryl group or a monovalent heterocyclic group, and these groups each optionally have a substituent. The plurality of $R^{H11}$ may be the same or different and may be combined together to form a ring together with the carbon atoms to which they are attached.

$L^{H2}$ represents a group represented by —N(-$L^{H21}$-$R^{H21}$)—. When a plurality of $L^{H2}$ are present, they may be the same or different. $L^{H21}$ represents a single bond, an arylene group or a divalent heterocyclic group, and these groups each optionally have a substituent. $R^{H21}$ represents a hydrogen atom, an alkyl group, a cycloalkyl group, an aryl group or a monovalent heterocyclic group, and these groups each optionally have a substituent.].

Effect of the Invention

According to the present invention, a light emitting device excellent in luminance life can be provided.

MODES FOR CARRYING OUT THE INVENTION

Suitable embodiments of the present invention will be illustrated in detail below.

Explanation of Common Term

Terms commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a heavy hydrogen atom or a light hydrogen atom.

A solid line representing a bond to a central metal in a formula representing a metal complex denotes a covalent bond or a coordinate bond.

"Polymer compound" denotes a polymer having molecular weight distribution and having a polystyrene-equivalent number average molecular weight of $1 \times 10^3$ to $1 \times 10^8$.

A polymer compound may be any of a block copolymer, a random copolymer, an alternating copolymer and a graft copolymer, and may also be another embodiment.

An end group of a polymer compound is preferably a stable group because if a polymerization active group remains intact at the end, when the polymer compound is used for fabrication of a light emitting device, the light emitting property or luminance life possibly becomes lower. This end group is preferably a group having a conjugated bond to the main chain, and includes, for example, groups bonding to an aryl group or a monovalent heterocyclic group via a carbon-carbon bond.

"Low molecular weight compound" denotes a compound having no molecular weight distribution and having a molecular weight of $1 \times 10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group and a dodecyl group, and groups obtained by substituting a hydrogen atom in these groups with a cycloalkyl group, an alkoxy group, a cycloalkoxy group, an aryl group, a fluorine atom or the like, and the alkyl group having a substituent includes, for example, a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl) propyl group and a 6-ethyloxyhexyl group.

The number of carbon atoms of "Cycloalkyl group" is, not including the number of carbon atoms of a substituent, usually 3 to 50, preferably 3 to 30, more preferably 4 to 20.

The cycloalkyl group optionally has a substituent, and examples thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group and a lauroyloxy group, and groups obtained by substituting a hydrogen atom in these groups with a cycloalkyl group, an alkoxy group, a cycloalkoxy group, an aryl group, a fluorine atom or the like.

The number of carbon atoms of "Cycloalkoxy group" is, not including the number of carbon atoms of a substituent, usually 3 to 40, preferably 4 to 10.

The cycloalkoxy group optionally has a substituent, and examples thereof include a cyclohexyloxy group.

The number of carbon atoms of "Aryloxy group" is, not including the number of carbon atoms of a substituent, usually 6 to 60, preferably 7 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidyl group, a quinolinyl group, an isoquinolinyl group, a pyrimidinyl group, a triazinyl group, and groups obtained by substituting a hydrogen atom in these groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl) amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group each optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and these groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group each optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group, a 5-hexynyl group, and these groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, preferably, groups represented by the formulae (A-1) to (A-20). The arylene group includes groups obtained by linking a plurality of these groups.

[Chemical formula 13]

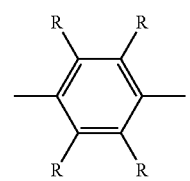

(A-1)

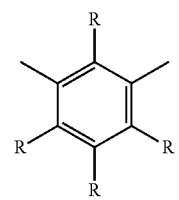

(A-2)

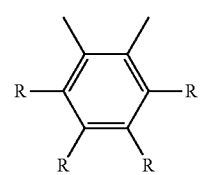

(A-3)

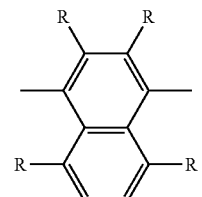

(A-4)

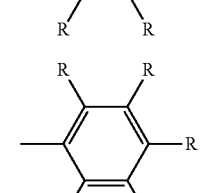

(A-5)

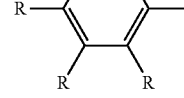

-continued
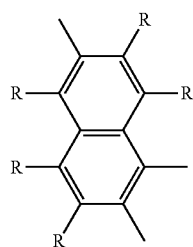
(A-6)
[Chemical formula 14]
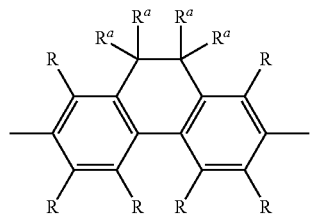
(A-7)
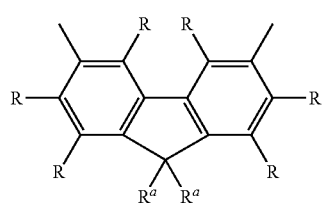
(A-8)
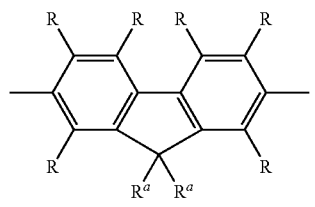
(A-9)
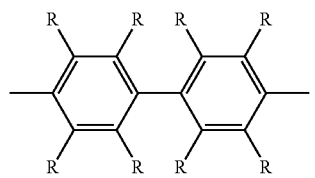
(A-10)
[Chemical formula 15]
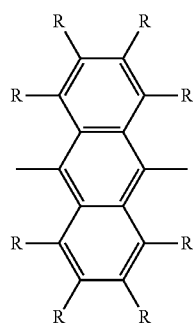
(A-11)
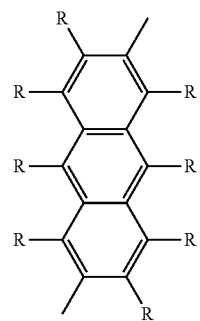
(A-12)
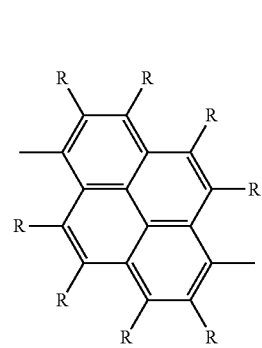
(A-13)
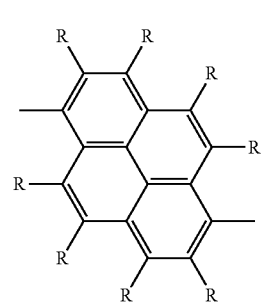
(A-14)
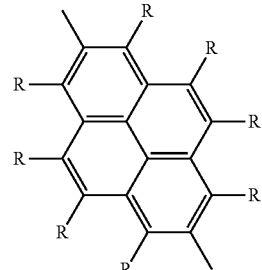
(A-15)
[Chemical formula 16]
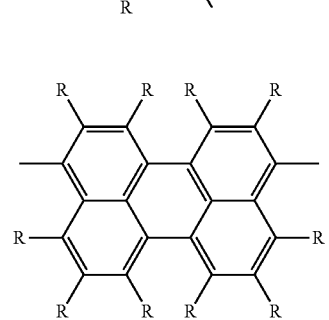
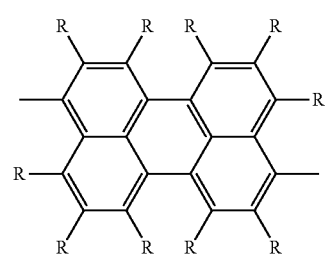
(A-16)

-continued

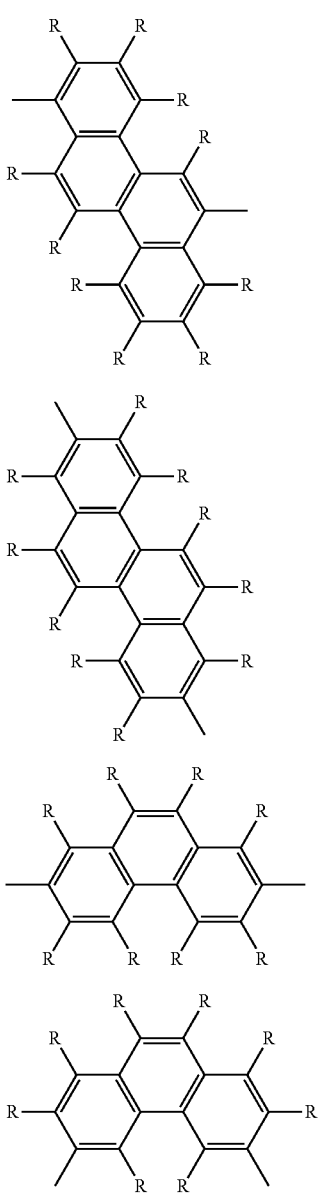

(A-17)

(A-18)

(A-19)

(A-20)

[wherein, R and $R^a$ each independently represent a hydrogen atom, an alkyl group, a cycloalkyl group, an aryl group or a monovalent heterocyclic group. The plurality of R and $R^a$ each may be the same or different, and groups $R^a$ may be combined together to form a ring together with the atoms to which they are attached.]

The number of carbon atoms of the divalent heterocyclic group is, not including the number of carbon atoms of a substituent, usually 2 to 60, preferably 3 to 20, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.

[Chemical formula 17]

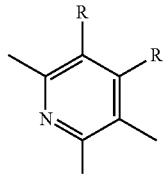

(AA-1)

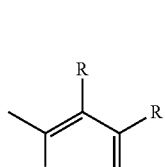

(AA-2)

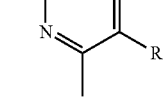

(AA-3)

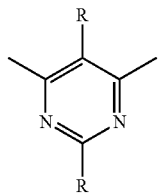

(AA-4)

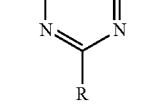

(AA-5)

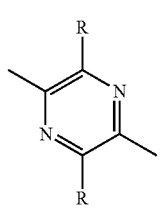

(AA-6)

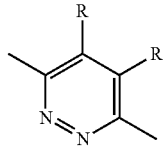

(AA-7)

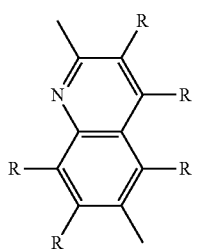

[Formula formula 18]
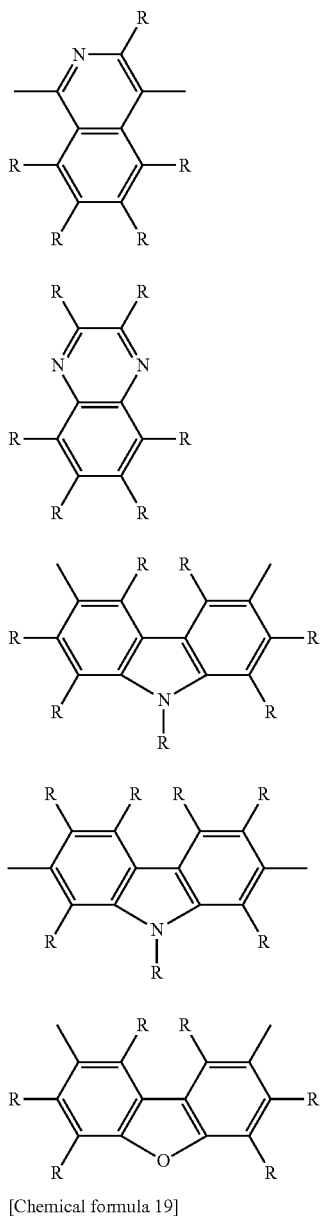
[Chemical formula 19]
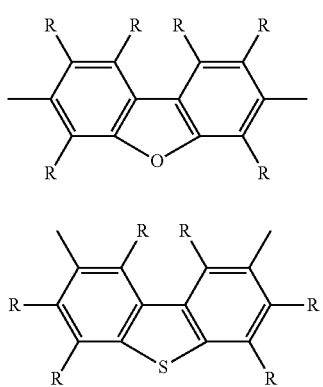
(AA-8)
(AA-9)
(AA-10)
(AA-11)
(AA-12)
(AA-13)
(AA-14)
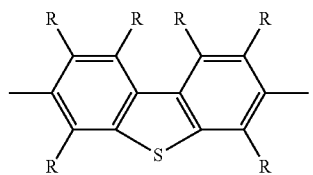  (AA-15)
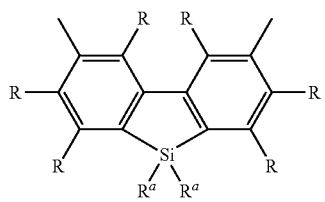  (AA-16)
[Chemical formula 20]
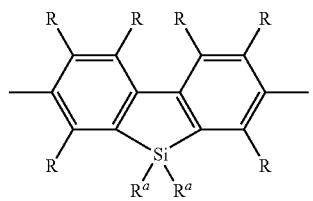  (AA-17)
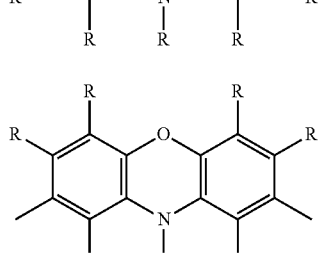  (AA-18)
(AA-19)
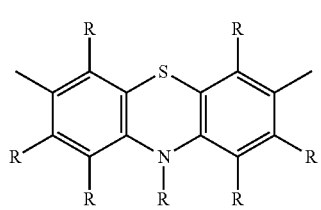  (AA-20)
[Chemical formula 21]
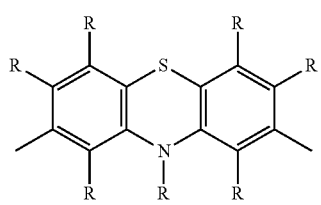  (AA-21)

-continued (AA-22) (AA-23) (AA-24) (AA-25) (AA-26) (AA-27) (AA-28) (AA-29) (AA-30) (AA-31)

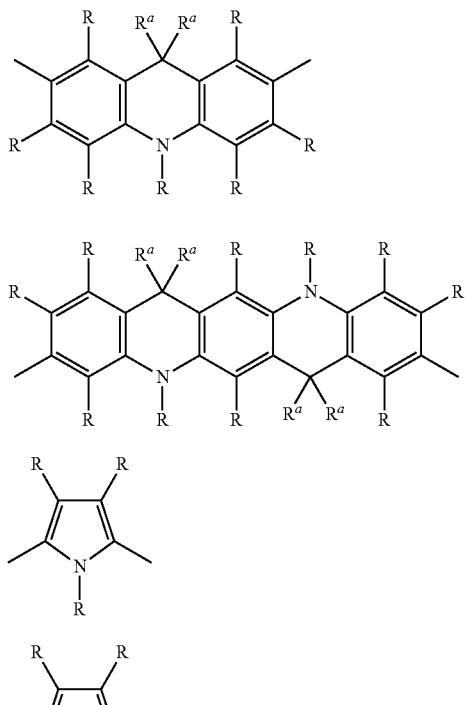

[Chemical formula 22]

-continued (AA-32)

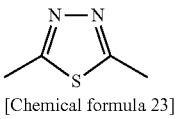

[Chemical formula 23]

(AA-33) (AA-34)

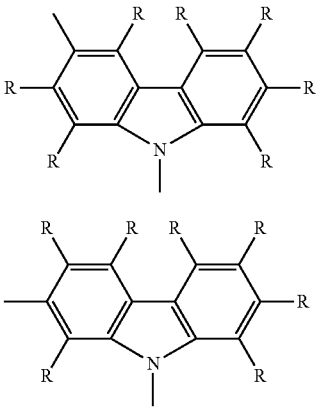

[wherein, R and R$^a$ represent the same meaning as described above.]

"Crosslinkable group" is a group capable of forming a new bond by being subjected to a heating treatment, an ultraviolet irradiation treatment, a radical reaction and the like, and crosslinkable groups are preferably groups represented by the formulae (XL-1) to (XL-17) of the above-described Group A of crosslinkable group.

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

<Light Emitting Device>

Next, the light emitting device of the present invention will be explained.

The light emitting device of the present invention is a light emitting device comprising an anode, a cathode, a first organic layer disposed between the anode and the cathode and a second organic layer disposed between the anode and the first organic layer, wherein the first organic layer is a layer formed by using one or more phosphorescent compounds, the second organic layer is a layer formed by using a composition comprising one or more phosphorescent compounds and a crosslinkable material, and at least one phosphorescent compound used for formation of the first organic layer and at least one phosphorescent compound used for formation of the second organic layer are the same phosphorescent compound represented by the formula (1).

The expression "formed by using" used for a relation between the first organic layer and the phosphorescent compound means that the first organic layer is formed using the phosphorescent compound. The phosphorescent compound may be contained, as it is, in the first organic layer, or the phosphorescent compound may be contained, in the form crosslinked intramolecularly, crosslinked intermolecularly or crosslinked in both modes (in the form of a crosslinked body of the phosphorescent compound), in the first organic layer.

The expression "formed by using" used for a relation between the second organic layer and the composition means that the second organic layer is formed using the composition. The phosphorescent compound and the crosslinkable material contained in the composition may be contained, as they are, in the second organic layer, or the phosphorescent compound or the crosslinkable material contained in the composition may be contained, in the form crosslinked intramolecularly, crosslinked intermolecularly or crosslinked in both modes (in the form of a crosslinked body of the phosphorescent compound or a crosslinked body of the crosslinkable material), in the second organic layer.

The method of forming the first organic layer and the second organic layer includes, for example, a vacuum vapor deposition method, and application methods typified by a spin coat method and an inkjet printing method.

When the first organic layer is formed by an application method, it is preferable to use an ink of first organic layer described later. After formation of the first organic layer, the phosphorescent compound can be crosslinked by heating or light irradiation. When the phosphorescent compound is contained, in the crosslinked form (in the form of a crosslinked body of the phosphorescent compound), in the first organic layer, the first organic layer is substantially insolubilized in a solvent. For this reason, the first organic layer can be suitably used for lamination of a light emitting device.

When the second organic layer is formed by an application method, it is preferable to use an ink of second organic layer described later. After formation of the second organic layer, the phosphorescent compound or the crosslinkable material contained in the composition can be crosslinked by heating or light irradiation. When the phosphorescent compound or the crosslinkable material is contained, in the crosslinked condition (in the form of a crosslinked body of the phosphorescent compound or a crosslinked body of the crosslinkable material), in the second organic layer, the second organic layer is substantially insolubilized in a solvent. For this reason, the second organic layer can be suitably used for lamination of a light emitting device.

It is preferable for the light emitting device of the present invention that the crosslinkable material contained in the composition is contained, in the crosslinked condition (in the form of a crosslinked body of the crosslinkable material), in the second organic layer.

That is, the light emitting device of the present invention is preferably a light emitting device comprising an anode, a cathode, a first organic layer disposed between the anode and the cathode and a second organic layer disposed between the anode and the first organic layer, wherein the first organic layer is a layer comprising one or more phosphorescent compounds, the second organic layer is a layer comprising one or more phosphorescent compounds and a crosslinked body of a crosslinkable material, and at least one phosphorescent compound contained in the first organic layer and at least one phosphorescent compound contained in the second organic layer are the same phosphorescent compound represented by the formula (1).

The temperature of heating for crosslinking is usually 25 to 300° C., preferably 50 to 250° C., more preferably 150 to 200° C.

The light used in light irradiation for crosslinking is, for example, ultraviolet light, near-ultraviolet light or visible light.

The method of analyzing the form of the first organic layer (the phosphorescent compound is contained as it is or a crosslinked body of the phosphorescent compound is contained) and the form of the second organic layer (the phosphorescent compound and the crosslinkable material are contained as they are or a crosslinked body of the phosphorescent compound or a crosslinked body of the crosslinkable material is contained) includes, for example, chemical separation and analysis methods typified by extraction and the like, instrumental analysis methods typified by infrared spectroscopy (IR), nuclear magnetic resonance spectroscopy (NMR), mass spectrometry (MS) and the like, and analysis methods combining chemical separation and analysis methods and instrumental analysis methods.

The first organic layer or the second organic layer can be subjected to solid-liquid extraction using an organic solvent typified by toluene, xylene, chloroform, tetrahydrofuran and the like, thereby separating components substantially insoluble in the organic solvent (insoluble components) and components soluble in the organic solvent (soluble components). The resultant insoluble components can be analyzed by infrared spectroscopy (IR) or nuclear magnetic resonance spectroscopy (NMR) and the resultant soluble components can be analyzed by nuclear magnetic resonance spectroscopy (NMR) or mass spectrometry (MS).

<First Organic Layer>

The first organic layer is a layer formed by using one or more phosphorescent compounds. As described above, the first organic layer is preferably a layer comprising one or more phosphorescent compounds.

[Phosphorescent Compound]

The phosphorescent compound used for formation of the first organic layer is preferably a phosphorescent compound represented by the formula (1). Also the phosphorescent compound used for formation of the second organic layer described later is preferably a phosphorescent compound represented by the formula (1). At least one phosphorescent compound used for formation of the first organic layer and at least one phosphorescent compound used for formation of the second organic layer are the same phosphorescent compound represented by the formula (1).

[Chemical formula 24]

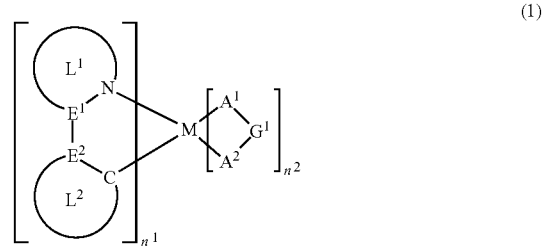

(1)

The phosphorescent compound represented by the formula (1) is constituted of a central metal M, a ligand of which number is defined by a subscript $n^1$ and a ligand of which number is defined by a subscript $n^2$.

M is preferably an iridium atom or a platinum atom, more preferably an iridium atom, because the light emitting device of the present invention is excellent in light emission efficiency.

$n^1$ is preferably 2 or 3, more preferably 3 when M is a ruthenium atom, a rhodium atom or an iridium atom.

$n^1$ is preferably 2 when M is a palladium atom or a platinum atom.

$E^1$ and $E^2$ are preferably carbon atoms.

The ring $L^1$ is preferably a pyridine ring, a pyrimidine ring, an imidazole ring or a triazole ring, and these rings each optionally have a substituent.

The ring $L^2$ is preferably a benzene ring, a naphthalene ring, a fluorene ring, a phenanthrene ring, a pyridine ring, a diazabenzene ring or a triazine ring, more preferably a benzene ring, a pyridine ring or a pyrimidine ring, and these rings each optionally have a substituent.

At least one ring selected from the group consisting of the ring $L^1$ and the ring $L^2$ has a group represented by the formula (2). It is preferable that the ring $L^2$ has a group represented by the formula (2).

When a plurality of the rings $L^1$ and the rings $L^2$ are present, it is recommendable that at least one ring of them has a group represented by the formula (2), and it is preferable that all of the plurality of the rings $L^1$, all of the plurality of the rings $L^2$, or all of the plurality of the rings $L^1$ and the rings $L^2$ have a group represented by the formula (2), and it is more preferable that all of the plurality of the rings $L^2$ have a group represented by the formula (2).

In the formula (2), $R^2$ is preferably an aryl group or a monovalent heterocyclic group, more preferably an aryl group, and these groups each optionally have a substituent.

The substituent which the aryl group, the monovalent heterocyclic group and the substituted amino group represented by $R^2$ optionally have is preferably an alkyl group, a cycloalkyl group, an aryl group, a monovalent heterocyclic group, an alkoxy group, a cycloalkoxy group, an aryloxy group or a substituted amino group, more preferably an alkyl group, a cycloalkyl group, an aryl group, a monovalent heterocyclic group, an alkoxy group or a cycloalkoxy group, further preferably an alkyl group, a cycloalkyl group or an aryl group, particularly preferably an alkyl group, and these groups each optionally further have a substituent.

The aryl group, the monovalent heterocyclic group or the substituted amino group represented by $R^2$ is preferably a dendron, because the light emitting device of the present invention is more excellent in luminance life.

"Dendron" denotes a group having a regular dendritic branched structure having a branching point at an atom or ring (that is, a dendrimer structure). A compound having a dendron (hereinafter, referred to as "dendrimer") includes, for example, structures described in literatures such as International Publication WO02/067343, JP-A No. 2003-231692, International Publication WO2003/079736, International Publication WO2006/097717 and the like.

The dendron is preferably a group represented by the formula (D-A) or (D-B).

[Chemical formula 25]

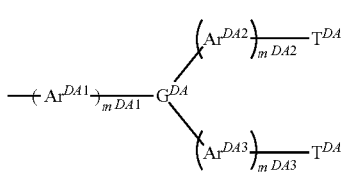
(D-A)

[Chemical formula 26]

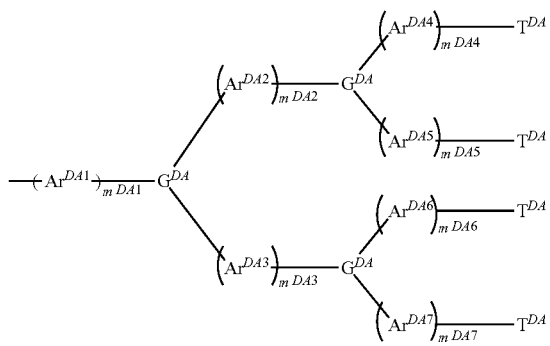
(D-B)

$m^{DA1}$, $m^{DA2}$, $m^{DA3}$, $m^{DA4}$, $m^{DA5}$, $m^{DA6}$ and $m^{DA7}$ are usually an integer of 10 or less, preferably an integer of 5 or less, more preferably 0 or 1. It is preferable that $m^{DA1}$, $m^{DA2}$, $m^{DA3}$, $m^{DA4}$, $m^{DA5}$, $m^{DA6}$ and $m^{DA7}$ are the same integer.

$G^{DA}$ is preferably a group represented by the formula (GDA-11) to (GDA-15), and these groups each optionally have a substituent.

[Chemical formula 27]

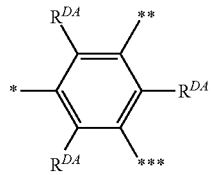
(GDA-11)

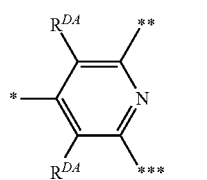
(GDA-12)

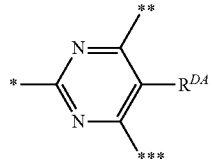
(GDA-13)

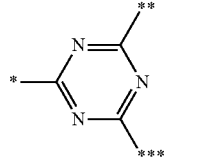
(GDA-14)

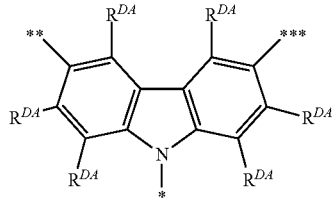
(GDA-15)

[wherein,

\* represents a linkage to Ar$^{DA1}$ in the formula (D-A), Ar$^{DA1}$ in the formula (D-B), Ar$^{DA2}$ in the formula (D-B) or Ar$^{DA3}$ in the formula (D-B).

\*\* represents a linkage to Ar$^{DA2}$ in the formula (D-A), Ar$^{DA2}$ in the formula (D-B), Ar$^{DA4}$ in the formula (D-B) or Ar$^{DA6}$ in the formula (D-B).

\*\*\* represents a linkage to Ar$^{DA3}$ in the formula (D-A), Ar$^{DA3}$ in the formula (D-B), Ar$^{DA5}$ in the formula (D-B) or Ar$^{DA7}$ in the formula (D-B).

R$^{DA}$ represents a hydrogen atom, an alkyl group, a cycloalkyl group, an alkoxy group, a cycloalkoxy group, an aryl group or a monovalent heterocyclic group, and these groups each optionally have a substituent. When a plurality of R$^{DA}$ are present, they may be the same or different.]

R$^{DA}$ is preferably a hydrogen atom, an alkyl group, a cycloalkyl group, an alkoxy group or a cycloalkoxy group, more preferably a hydrogen atom, an alkyl group or cycloalkyl group, and these groups each optionally have a substituent.

It is preferable that Ar$^{DA1}$, Ar$^{DA2}$, Ar$^{DA3}$, Ar$^{DA4}$, Ar$^{DA5}$, Ar$^{DA6}$ and Ar$^{DA7}$ are groups represented by the formulae (ArDA-1) to (ArDA-3).

[Chemical formula 28]

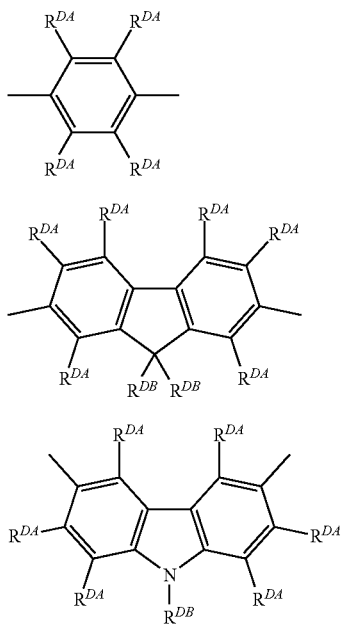

(ArDA-1)

(ArDA-2)

(ArDA-3)

[wherein,

R$^{DA}$ represents the same meaning as described above.

R$^{DB}$ represents a hydrogen atom, an alkyl group, a cycloalkyl group, an aryl group or a monovalent heterocyclic group, and these groups each optionally have a substituent. When a plurality of R$^{DB}$ are present, they may be the same or different.]

R$^{DB}$ is preferably an alkyl group, a cycloalkyl group, an aryl group or a monovalent heterocyclic group, more preferably an aryl group or a monovalent heterocyclic group, further preferably an aryl group, and these groups each optionally have a substituent.

T$^{DA}$ is preferably groups represented by the formulae (TDA-1) to (TDA-3).

[Chemical formula 29]

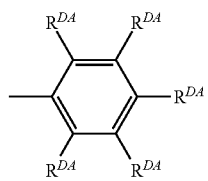

(TDA-1)

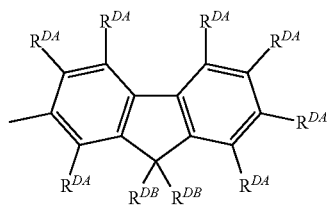

(TDA-2)

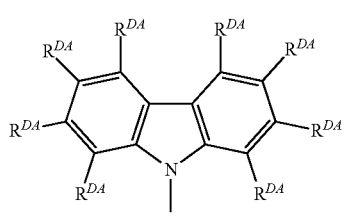

(TDA-3)

[wherein, R$^{DA}$ and R$^{DB}$ represent the same meaning described above.]

The group represented by the formula (D-A) is preferably a group represented by the formula (D-A1) to (D-A3).

[Chemical formula 30]

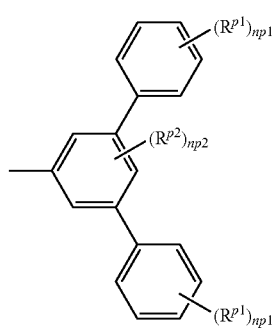

(D-A1)

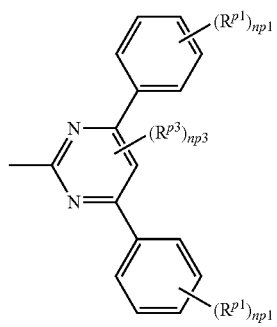

(D-A2)

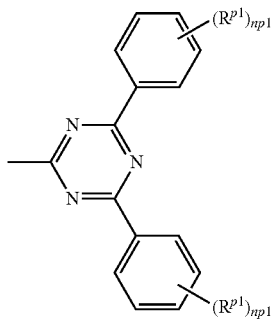

(D-A3)

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. The plurality of np1 may be the same or different.]

The group represented by the formula (D-B) is preferably a group represented by the formula (D-B1) to (D-B3).

[Chemical formula 31]

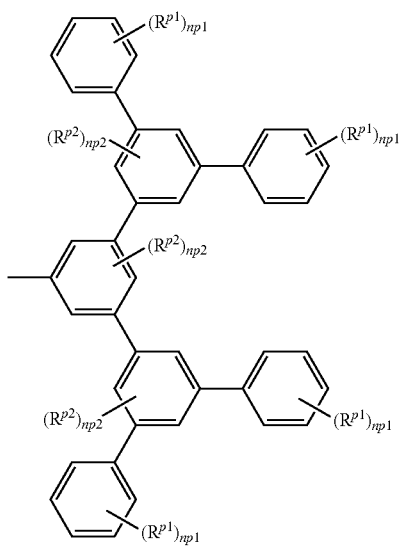

(D-B1)

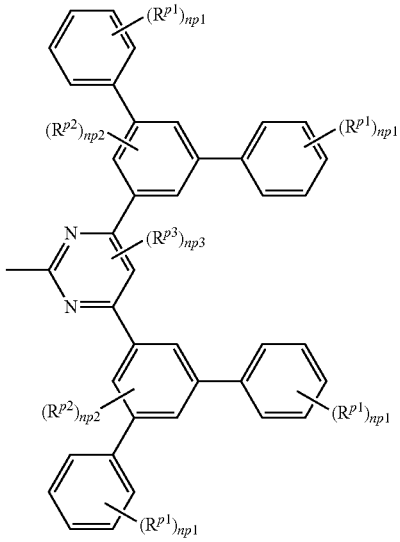

(D-B2)

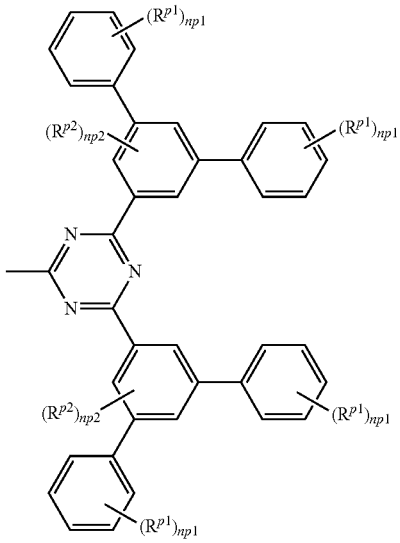

(D-B3)

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. When a plurality of np1 and np2 are present, they may be the same or different at each occurrence.]

np1 is preferably 0 or 1, more preferably 1. np2 is preferably 0 or 1, more preferably 0. np3 is preferably 0.

$R^{p1}$, $R^{p2}$ and $R^{p3}$ are preferably an alkyl group or a cycloalkyl group.

The anionic bidentate ligand represented by $A^1$-$G^1$-$A^2$ includes, for example, ligands shown below.

[Chemical formula 32]

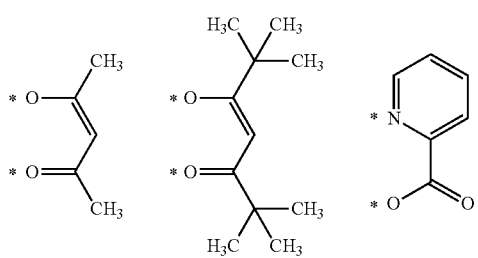

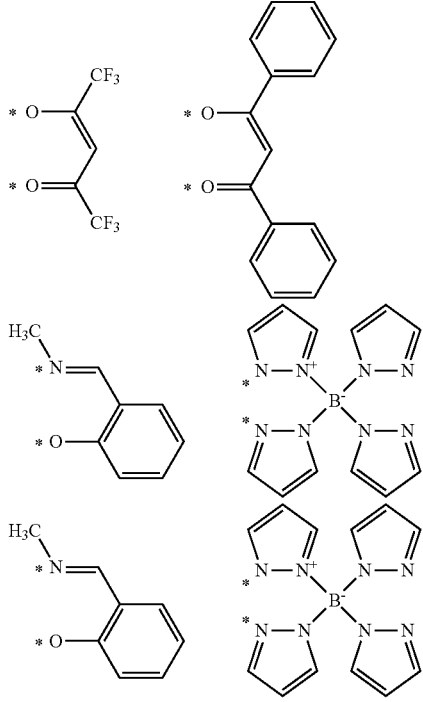

[Chemical formula 33]

[wherein, * represents a site binding to M.]

The anionic bidentate ligand represented by $A^1$-$G^1$-$A^1$ may be a ligand shown below. The anionic bidentate ligand represented by $A^1$-$G^1$-$A^2$ is different from the ligand of which number is defined by a subscript $n^1$.

[Chemical formula 34]

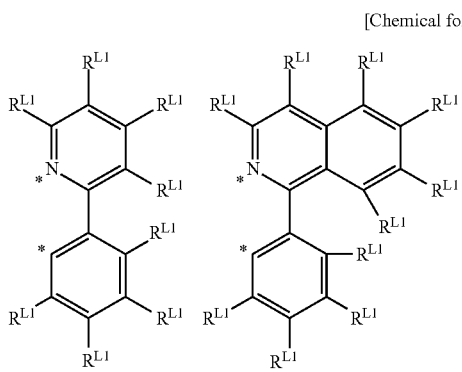

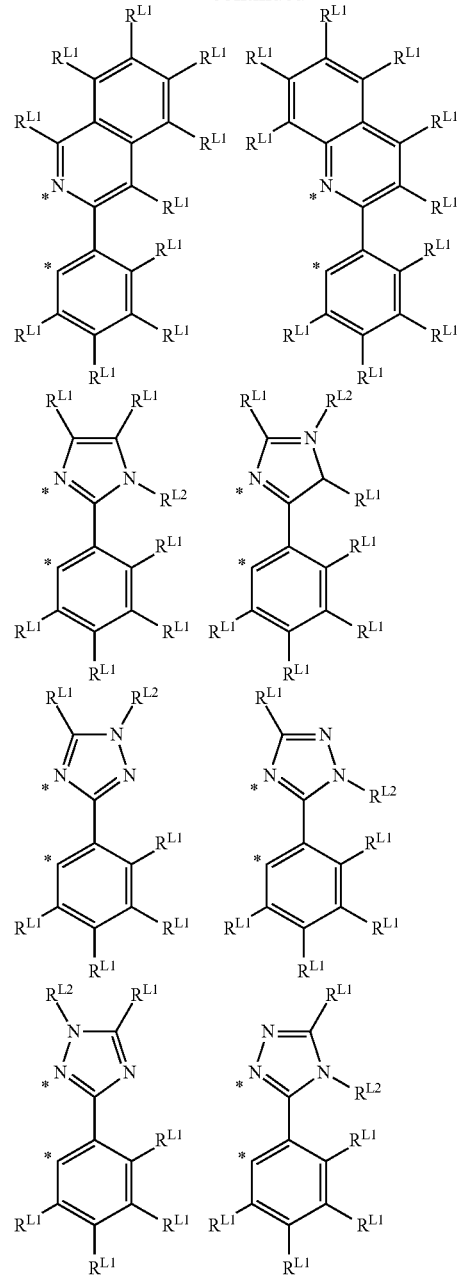

[wherein,

* represents a site binding to M.

$R^{L1}$ represents a hydrogen atom, an alkyl group, a cycloalkyl group or a halogen atom, and these groups each optionally have a substituent. The plurality of $R^{L1}$ may be the same or different.

$R^{L2}$ represents an alkyl group, a cycloalkyl group or a halogen atom, and these groups each optionally have a substituent.]

The phosphorescent compound represented by the formula (1) is preferably a phosphorescent compound represented by the formula (1-A) or a phosphorescent compound represented by the formula (1-B), because the light emitting device of the present invention is excellent in light emission efficiency.

[Chemical formula 35]

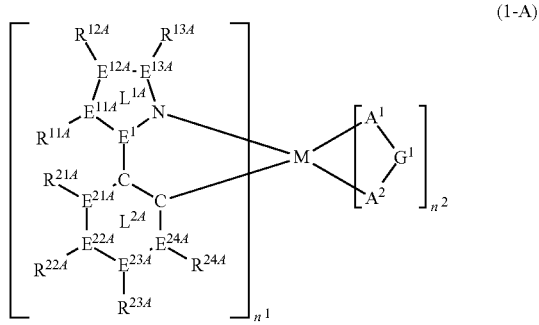

(1-A)

When the ring $L^{1A}$ is an imidazole ring, an imidazole ring in which $E^{11A}$ is a nitrogen atom or an imidazole ring in which $E^{12A}$ is a nitrogen atom is preferable, an imidazole ring in which $E^{11A}$ is a nitrogen atom is more preferable.

When the ring $L^{1A}$ is a triazole ring, a triazole ring in which $E^{11A}$ and $E^{12A}$ are nitrogen atoms or a triazole ring in which $E^{11A}$ and $E^{13A}$ are nitrogen atoms is preferable, a triazole ring in which $E^{11A}$ and $E^{12A}$ are nitrogen atoms is more preferable.

When $E^{11A}$ is a nitrogen atom and $R^{11A}$ is present, $R^{11A}$ is preferably an alkyl group, a cycloalkyl group or a group represented by the formula (2), and these groups each optionally have a substituent.

When $E^{11A}$ is a carbon atom, $R^{11A}$ is preferably a hydrogen atom, an alkyl group, a cycloalkyl group, an aryl group or a monovalent heterocyclic group, more preferably a hydrogen atom, an alkyl group, a cycloalkyl group or an aryl group, further preferably a hydrogen atom, an alkyl group or a cycloalkyl group, and these groups each optionally have a substituent.

When $E^{12A}$ is a nitrogen atom and $R^{12A}$ is present, $R^{12A}$ is preferably an alkyl group, a cycloalkyl group or a group represented by the formula (2), and these groups each optionally have a substituent.

When $E^{12A}$ is a carbon atom, $R^{12A}$ is preferably a hydrogen atom, an alkyl group, a cycloalkyl group, an aryl group or a monovalent heterocyclic group, more preferably a hydrogen atom, an alkyl group, a cycloalkyl group or an aryl group, further preferably a hydrogen atom, an alkyl group or a cycloalkyl group, and these groups each optionally have a substituent.

When $E^{13A}$ is a nitrogen atom and $R^{13A}$ is present, $R^{13A}$ is preferably an alkyl group, a cycloalkyl group or a group represented by the formula (2), and these groups each optionally have a substituent.

When $E^{13A}$ is a carbon atom, $R^{13A}$ is preferably a hydrogen atom, an alkyl group, a cycloalkyl group, an aryl group or a monovalent heterocyclic group, more preferably a hydrogen atom, an alkyl group, a cycloalkyl group or an aryl group, further preferably a hydrogen atom, an alkyl group or a cycloalkyl group, and these groups each optionally have a substituent.

When the ring $L^{1A}$ has a group represented by the formula (2), it is preferable that $R^{11A}$ or $R^{12A}$ is a group represented by the formula (2), it is more preferable that $R^{11A}$ is a group represented by the formula (2). The group represented by the formula (2) is preferably a dendron.

When the ring $L^{2A}$ is a pyridine ring, a pyridine ring in which $E^{21A}$ is a nitrogen atom, a pyridine ring in which $E^{22A}$ is a nitrogen atom or a pyridine ring in which $E^{23A}$ is a nitrogen atom is preferable, a pyridine ring in which $E^{22A}$ is a nitrogen atom is more preferable.

When the ring $L^{2A}$ is a pyrimidine ring, a pyrimidine ring in which $E^{21A}$ and $E^{23A}$ are nitrogen atoms or a pyrimidine ring in which $E^{22A}$ and $E^{24A}$ are nitrogen atoms is preferable, a pyrimidine ring in which $E^{22A}$ and $E^{24A}$ are nitrogen atoms is more preferable.

The ring $L^{2A}$ is preferably a benzene ring.

$R^{21A}$, $R^{22A}$, $R^{23A}$ and $R^{24A}$ represent preferably a hydrogen atom, an alkyl group, a cycloalkyl group or a group represented by the formula (2), more preferably a hydrogen atom or a group represented by the formula (2), and these groups each optionally have a substituent.

When the ring $L^{2A}$ has a group represented by the formula (2), it is preferable that $R^{22A}$ or $R^{23A}$ is a group represented by the formula (2), it is more preferable that $R^{22A}$ is a group represented by the formula (2). The group represented by the formula (2) is preferably a dendron.

[Chemical formula 36]

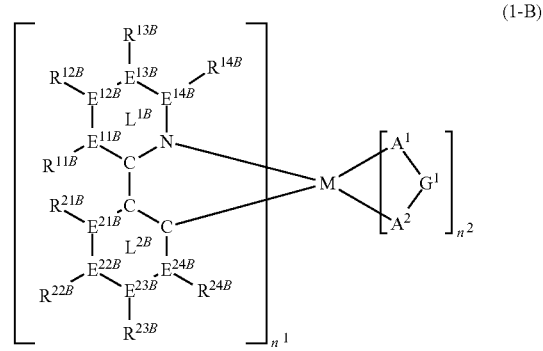

(1-B)

When the ring $L^{1B}$ is a pyrimidine ring, a pyrimidine ring in which $E^{11B}$ is a nitrogen atom or a pyrimidine ring in which $E^{13B}$ is a nitrogen atom is preferable, a pyrimidine ring in which $E^{11B}$ is a nitrogen atom is more preferable.

$R^{11B}$, $R^{12B}$, $R^{13B}$ and $R^{14B}$ represent preferably a hydrogen atom, an alkyl group, a cycloalkyl group or a group represented by the formula (2), more preferably a hydrogen atom or a group represented by the formula (2), and these groups each optionally have a substituent.

When the ring $L^{1B}$ has a group represented by the formula (2), it is preferable that $R^{11B}$, $R^{12B}$ or $R^{13B}$ a is a group represented by the formula (2), it is more preferable $R^{11B}$ or $R^{13B}$ is a group represented by the formula (2), it is further preferable that $R^{11B}$ is a group represented by the formula (2). The group represented by the formula (2) is preferably a dendron.

When the ring $L^{2B}$ is a pyridine ring, a pyridine ring in which $E^{21B}$ is a nitrogen atom, a pyridine ring in which $E^{22B}$ is a nitrogen atom or a pyridine ring in which $E^{23B}$ is a nitrogen atom is preferable, a pyridine ring in which $E^{22B}$ is a nitrogen atom is more preferable.

When the ring $L^{2B}$ is a pyrimidine ring, a pyrimidine ring in which $E^{21B}$ and $E^{23B}$ are nitrogen atoms or a pyrimidine ring in which $E^{22B}$ and $E^{24B}$ are nitrogen atoms is preferable, a pyrimidine ring in which $E^{22B}$ and $E^{24B}$ are nitrogen atoms is more preferable.

The ring $L^{2B}$ is preferably a benzene ring.

$R^{21B}$, $R^{22B}$, $R^{23B}$ and $R^{24B}$ represent preferably a hydrogen atom, an alkyl group, a cycloalkyl group or a group represented by the formula (2), more preferably a hydrogen atom or a group represented by the formula (2), and these groups each optionally have a substituent.

When the ring $L^{2B}$ has a group represented by the formula (2), it is preferable that $R^{22B}$ or $R^{23B}$ is a group represented by the formula (2), it is more preferable that $R^{22B}$ is a group represented by the formula (2). The group represented by the formula (2) is preferably a dendron.

The phosphorescent compound represented by the formula (1-A) is preferably a phosphorescent compound represented by the formula (1-A1), a phosphorescent compound represented by the formula (1-A2), a phosphorescent compound represented by the formula (1-A3) or a phosphorescent compound represented by the formula (1-A4), more preferably a phosphorescent compound represented by the formula (1-A1) or a phosphorescent compound represented by the formula (1-A3), further preferably a phosphorescent compound represented by the formula (1-A3).

The phosphorescent compound represented by the formula (1-B) is preferably a phosphorescent compound represented by the formula (1-B1), a phosphorescent compound represented by the formula (1-B2) or a phosphorescent compound represented by the formula (1-B3), more preferably a phosphorescent compound represented by the formula (1-B1) or a phosphorescent compound represented by the formula (1-B2).

[Chemical formula 37]

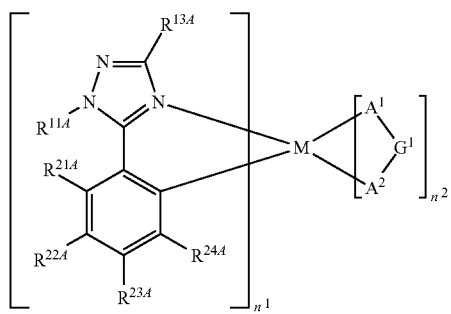

(1-A1)

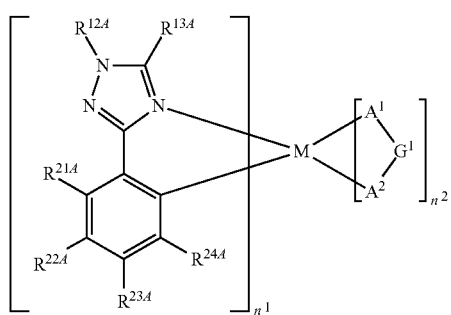

(1-A2)

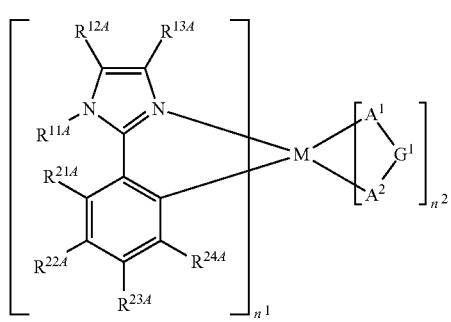

(1-A3)

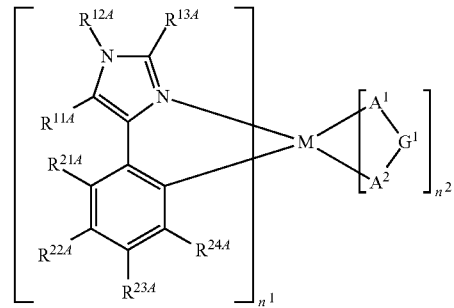

(1-A4)

[Chemical formula 38]

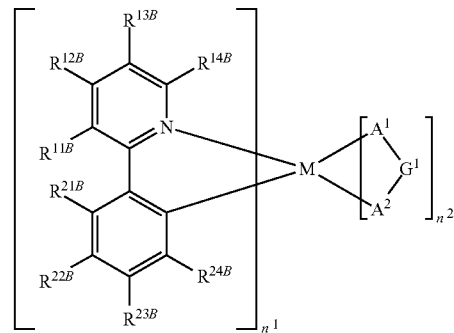

(1-B1)

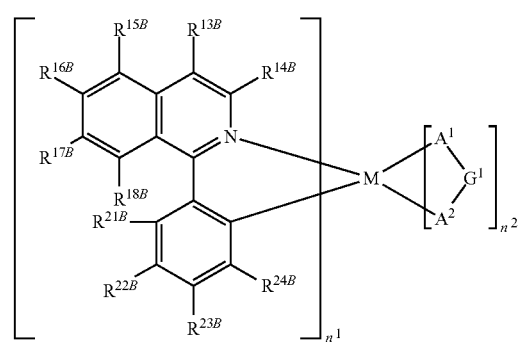

(1-B2)

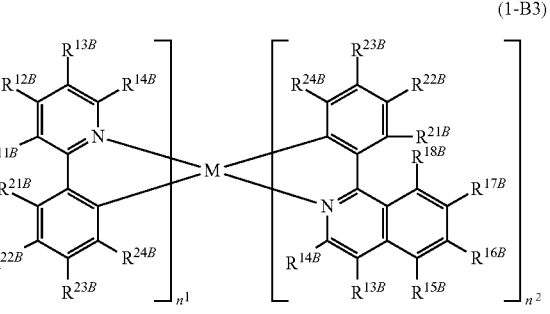

(1-B3)

The phosphorescent compound represented by the formula (1) includes, for example, phosphorescent compounds shown below.
[Chemical formula 39]
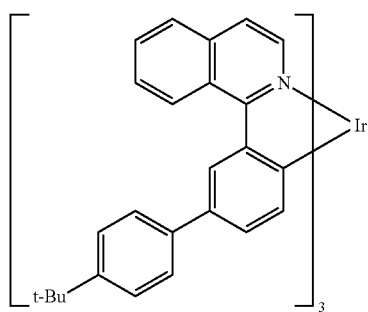
COM-3
[Chemical formula 40]
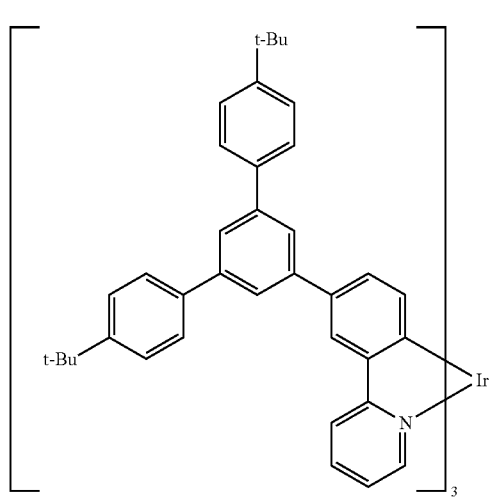
COM-4
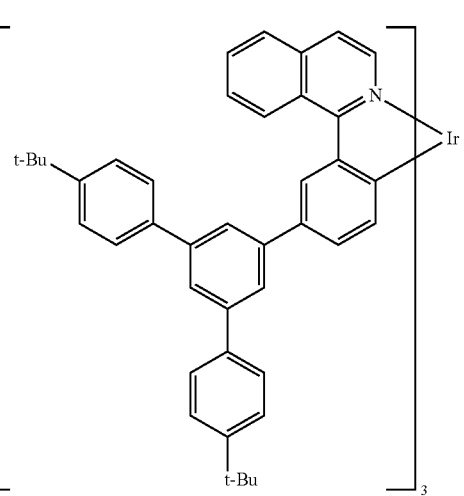
COM-5
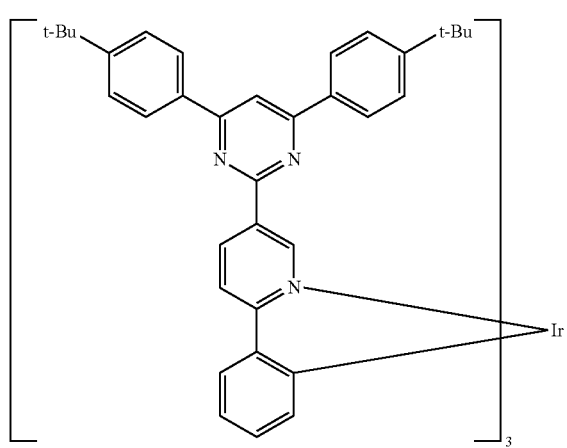
COM-6

-continued
[Chemical formula 41]
COM-7
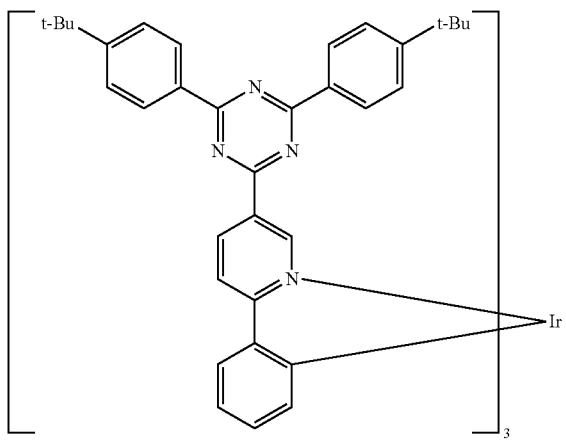
COM-8
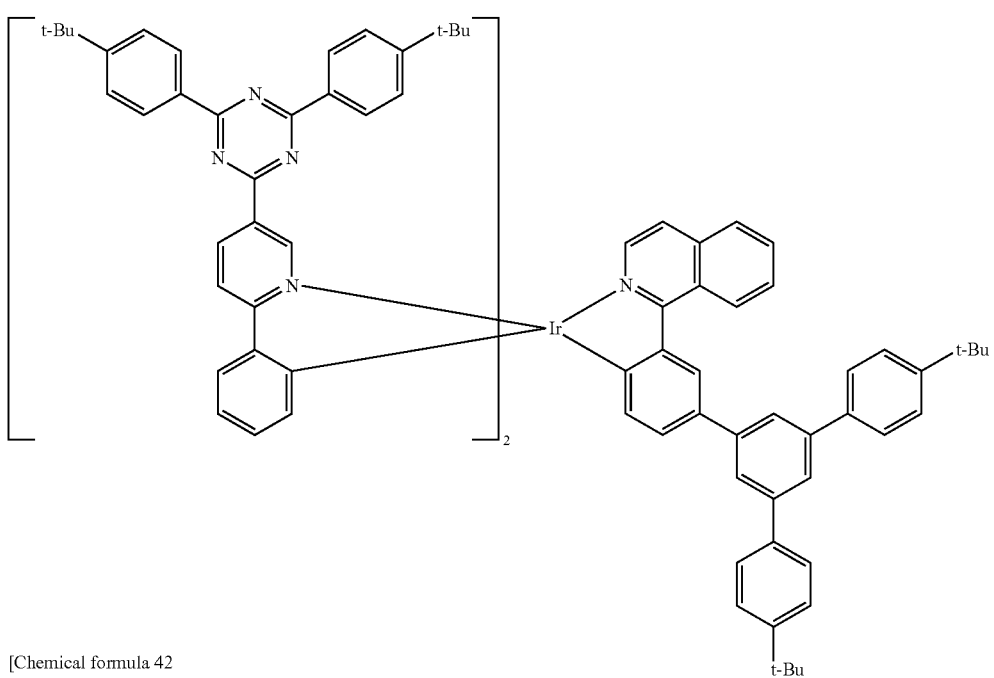
[Chemical formula 42]
COM-9
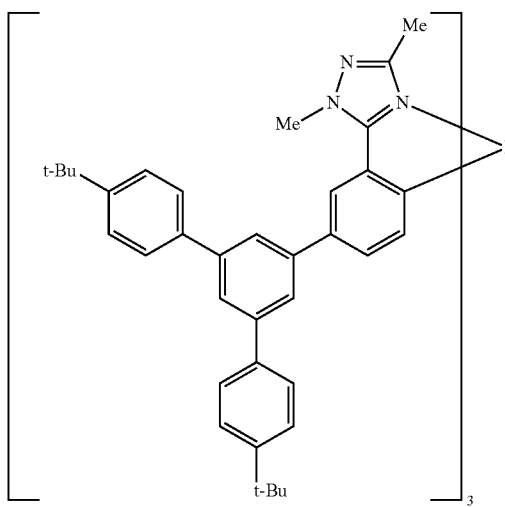
COM-10
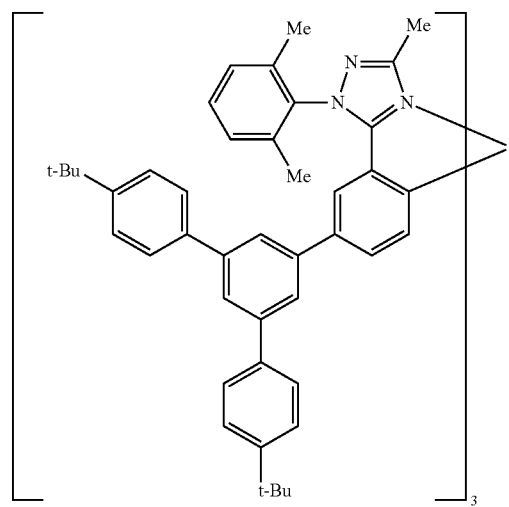

-continued
COM-11
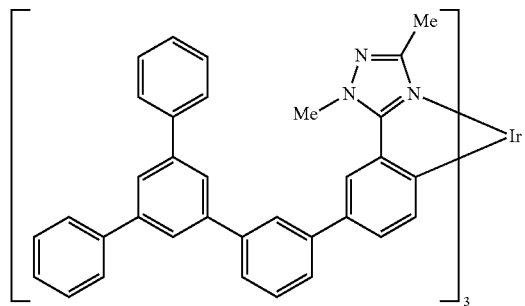
COM-12
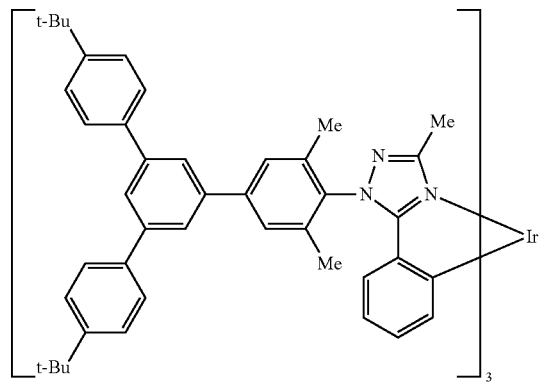
COM-13
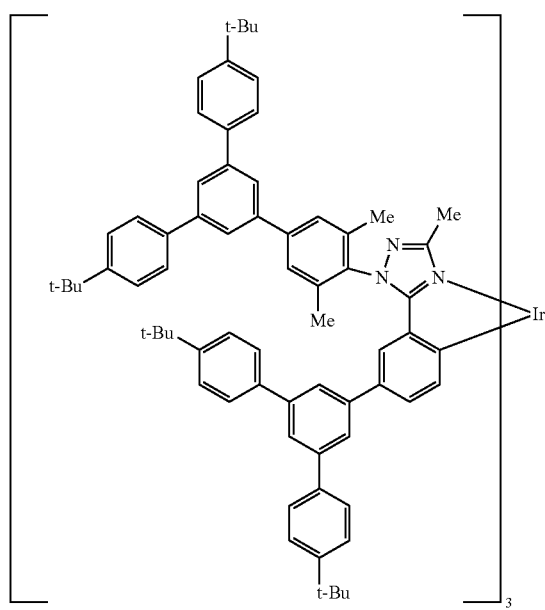
[Chemical formula 43]
COM-14
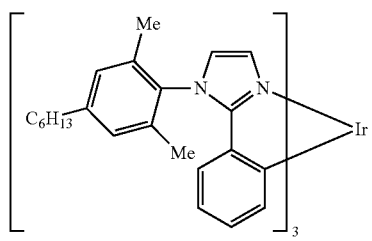
COM-15
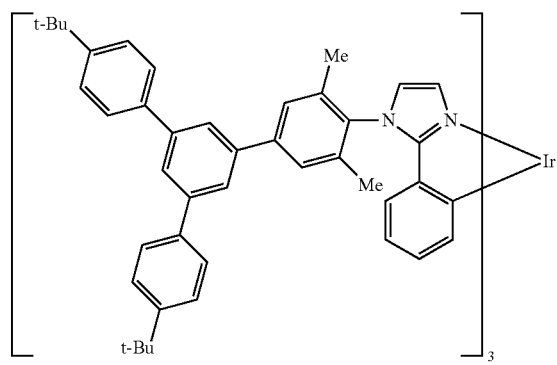

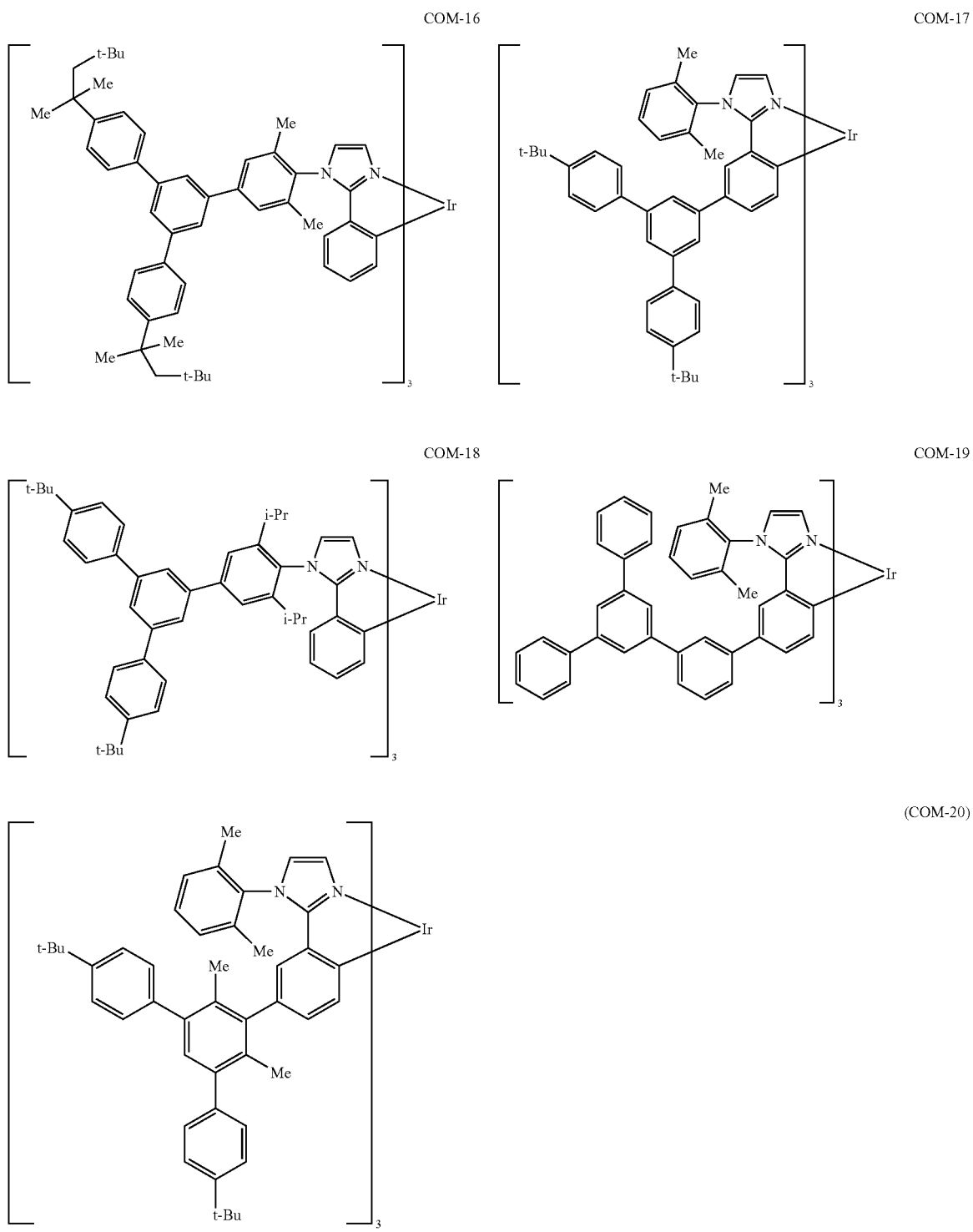

As described above, at least one phosphorescent compound used for formation of the first organic layer is a phosphorescent compound represented by the formula (1) (the same phosphorescent compound as at least one phosphorescent compound used for formation of the second organic layer), and first organic layer may be a layer formed by using a phosphorescent compound represented by the formula (1) and other phosphorescent compound together or may be a layer comprising a phosphorescent compound represented by the formula (1) and other phosphorescent compound. The other phosphorescent compound includes, for example, phosphorescent compounds represented by the following formulae.

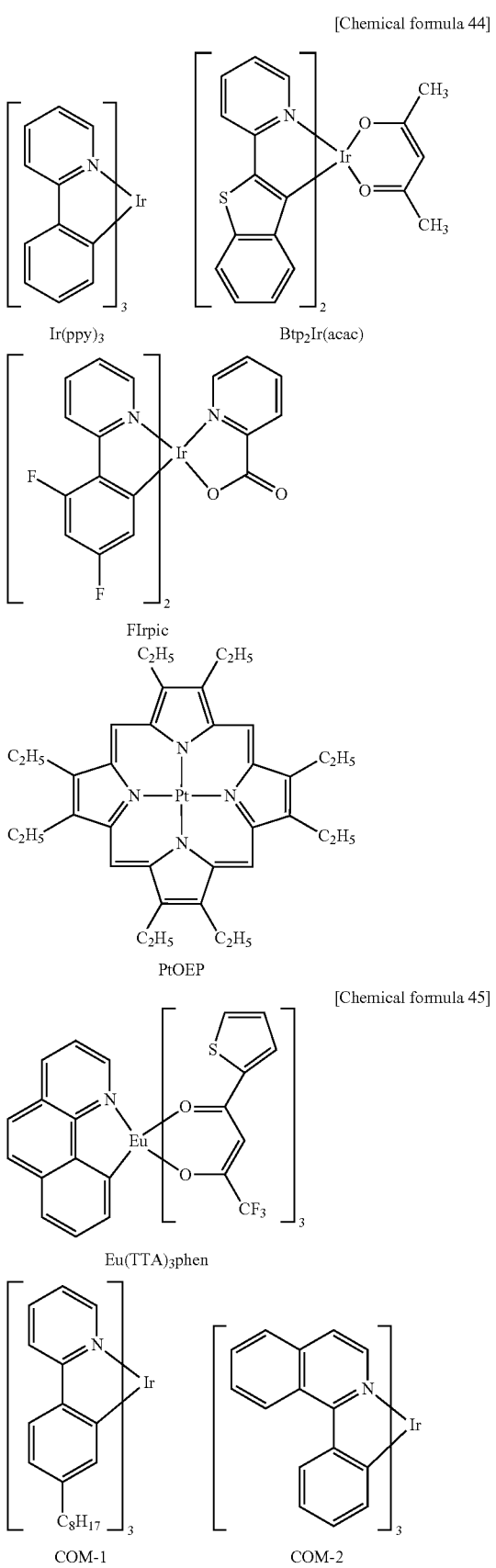

[Chemical formula 44]

Ir(ppy)₃   Btp₂Ir(acac)

FIrpic

PtOEP

[Chemical formula 45]

Eu(TTA)₃phen

COM-1   COM-2

The phosphorescent compound used for formation of the first organic layer can be synthesized according to methods described, for example, in Japanese Patent Application National Publication No. 2004-530254, JP-A No. 2008-179617, JP-A No. 2011-105701, Japanese Patent Application National Publication No. 2007-504272, JP-A No. 2013-147449 and JP-A No. 2013-147450.

[Host Material]

The first organic layer is preferably a layer formed by using a composition comprising one or more phosphorescent compounds and a host material having at least one function selected from the group consisting of hole injectability, hole transportability, electron injectability and electron transportability, more preferably a layer comprising one or more phosphorescent compounds and a host material having at least one function selected from the group consisting of hole injectability, hole transportability, electron injectability and electron transportability, because the light emitting device of the present invention is excellent in light emission efficiency. In the composition, the host material may be contained singly, or two or more of the host materials may be contained.

In the composition comprising the phosphorescent compound and the host material, the content of the phosphorescent compound is usually 0.1 to 50 parts by weight, preferably 1 to 45 parts by weight, more preferably 5 to 40 parts by weight, when the total amount of the phosphorescent compound and the host material is 100 parts by weight.

It is preferable that the lowest excited triplet state ($T_1$) of the host material has energy level equal to or higher than that of $T_1$ of the phosphorescent compound used for formation of the first organic layer, because the light emitting device of the present invention is excellent in light emission efficiency.

It is preferable that the host material is one showing solubility in a solvent which is capable of dissolving a phosphorescent compound used for formation of the first organic layer, because the light emitting device of the present invention can be fabricated by a solution application process.

The host material is classified into low molecular weight compounds and polymer compounds.

[Low Molecular Weight Host]

The low molecular weight compound which is preferable as a host compound (hereinafter, referred to as "low molecular weight host") will be explained.

The low molecular weight host is preferably a compound represented by the formula (H-1).

[Chemical formula 46]

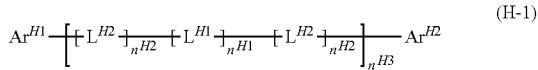

(H-1)

$Ar^{H1}$ and $Ar^{H2}$ are preferably a phenyl group, a fluorenyl group, a spirobifluorenyl group, a pyridyl group, a pyrimidinyl group, a triazinyl group, a quinolinyl group, an isoquinolinyl group, a thienyl group, a benzothienyl group, a dibenzothienyl group, a furyl group, a benzofuryl group, a dibenzofuryl group, a pyrrolyl group, an indolyl group, an azaindolyl group, a carbazolyl group, an azacarbazolyl group, a diazacarbazolyl group, a phenoxazinyl group or a phenothiazinyl group, more preferably a phenyl group, a spirobifluorenyl group, a pyridyl group, a pyrimidinyl group, a triazinyl group, a dibenzothienyl group, a dibenzofuryl group, a carbazolyl group or an azacarbazolyl group, further preferably a phenyl group, a pyridyl group, a carbazolyl group or an azacarbazolyl group, particularly preferably a group represented by the formula (TDA-1) or (TDA-3) described above, especially preferably a group represented by the formula (TDA-3) described above, and these groups each optionally have a substituent.

The substituent which $Ar^{H1}$ and $Ar^{H2}$ optionally have is preferably a halogen atom, an alkyl group, a cycloalkyl group, an alkoxy group, a cycloalkoxy group, an aryl group or a monovalent heterocyclic group, more preferably an alkyl group, a cycloalkoxy group, an alkoxy group or cycloalkoxy group, further preferably an alkyl group or cycloalkoxy group, and these groups each optionally further have a substituent.

$n^{H1}$ is preferably 1. $n^{H2}$ is preferably 0.

$n^{H3}$ is usually an integer of 0 to 10, preferably an integer of 0 to 5, further preferably an integer of 1 to 3, particularly preferably 1.

$n^{H11}$ is preferably an integer of 1 to 5, more preferably an integer of 1 to 3, further preferably 1.

$R^{H11}$ is preferably a hydrogen atom, an alkyl group, a cycloalkyl group, an aryl group or a monovalent heterocyclic group, more preferably a hydrogen atom, an alkyl group or a cycloalkyl group, further preferably a hydrogen atom or an alkyl group, and these groups each optionally have a substituent.

$L^{H1}$ is preferably an arylene group or a divalent heterocyclic group.

$L^{H1}$ is preferably a group represented by the formula (A-1) to (A-3), the formula (A-8) to (A-10), the formula (AA-1) to (AA-6), the formula (AA-10) to (AA-21) or the formula (AA-24) to (AA-34), more preferably a group represented by the formula (A-1), the formula (A-2), the formula (A-8), the formula (A-9), the formula (AA-1) to (AA-4), the formula (AA-10) to (AA-15) or the formula (AA-29) to (AA-34), further preferably a group represented by the formula (A-1), the formula (A-2), the formula (A-8), the formula (A-9), the formula (AA-2), the formula (AA-4) or the formula (AA-10) to (AA-15), particularly preferably a group represented by the formula (A-1), the formula (A-2), the formula (A-8), the formula (AA-2), the formula (AA-4), the formula (AA-10), the formula (AA-12) or the formula (AA-14), especially preferably a group represented by the formula (A-1), the formula (A-2), the formula (AA-2), the formula (AA-4) or the formula (AA-14).

The substituent which $L^{H1}$ optionally has is preferably a halogen atom, an alkyl group, a cycloalkyl group, an alkoxy group, a cycloalkoxy group, an aryl group or a monovalent heterocyclic group, more preferably an alkyl group, an alkoxy group, an aryl group or a monovalent heterocyclic group, further preferably an alkyl group, an aryl group or a monovalent heterocyclic group, and these groups each optionally further have a substituent.

$L^{H21}$ is preferably a single bond or an arylene group, more preferably a single bond, and this arylene group optionally has a substituent.

The definition and examples of the arylene group or the divalent heterocyclic group represented by $L^{H21}$ are the same as the definition and examples of the arylene group or the divalent heterocyclic group represented by $L^{H1}$.

$R^{H21}$ is preferably an aryl group or a monovalent heterocyclic group, and these groups each optionally have a substituent.

The definition and examples of the aryl group and the monovalent heterocyclic group represented by $R^{H21}$ are the same as the definition and examples of the aryl group and the monovalent heterocyclic group represented by $Ar^{H1}$ and $Ar^{H2}$.

The definition and examples of the substituent which $R^{H21}$ may optionally has are the same as the definition and examples of the substituent which $Ar^{H1}$ and $Ar^{H2}$ optionally have.

The compound represented by the formula (H-1) is preferably a compound represented by the formula (H-2).

[Chemical formula 47]

[wherein, $Ar^{H1}$, $Ar^{H2}$, $n^{H3}$ and $L^{H1}$ represent the same meaning as described above.]

As the compound represented by the formula (H-1), compounds represented by the following formulae (H-101) to (H-118) are exemplified.

[Chemical formula 48]

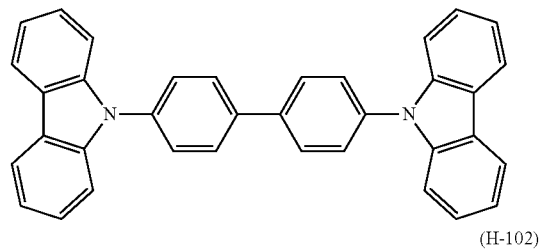

(H-101)

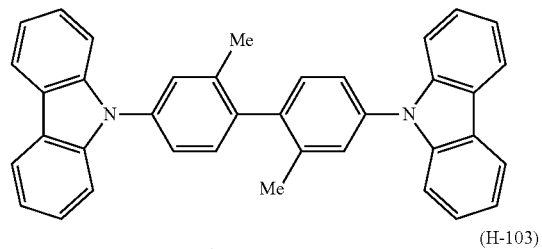

(H-102)

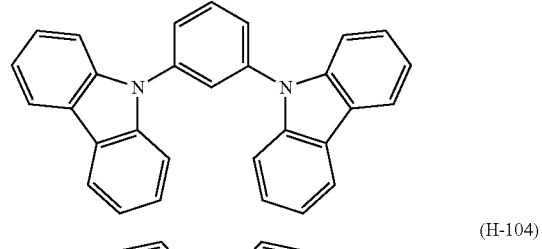

(H-103)

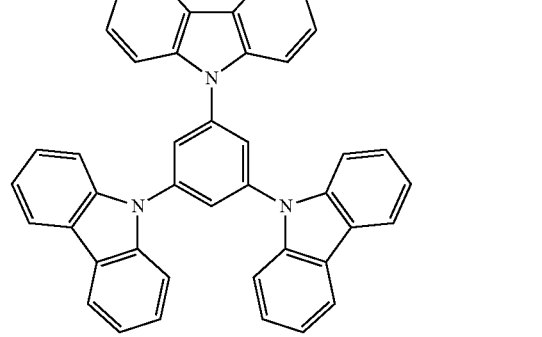

(H-104)

-continued
(H-105)
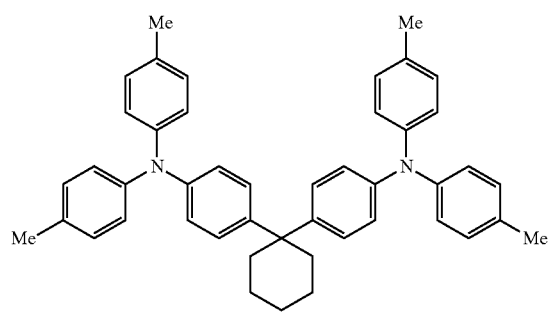
(H-106)
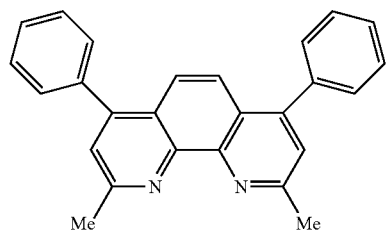
[Chemical formula 49]
(H-107)
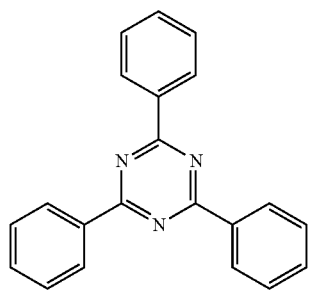
(H-108)
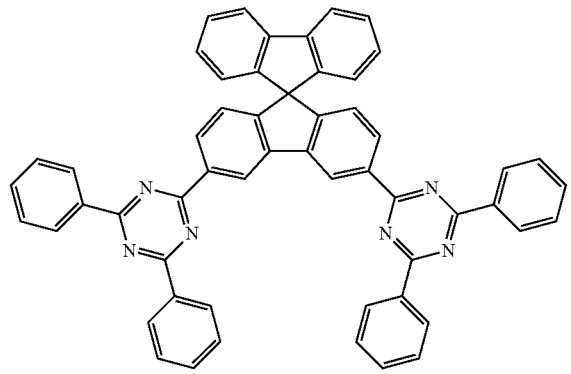
(H-109)
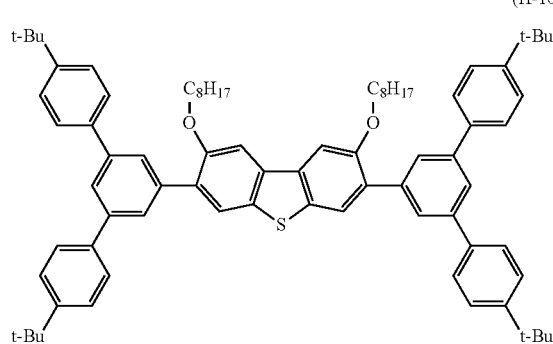
-continued
(H-110)
(H-111)
[Chemical formula 50]
(H-112)
(H-113)
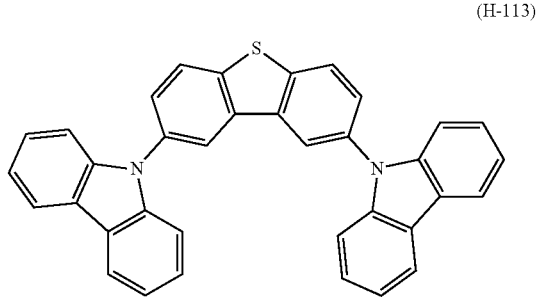

(H-114)

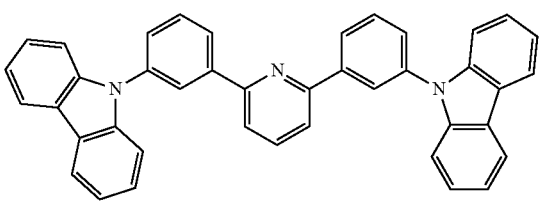

[Chemical formula 51]

(H-115)

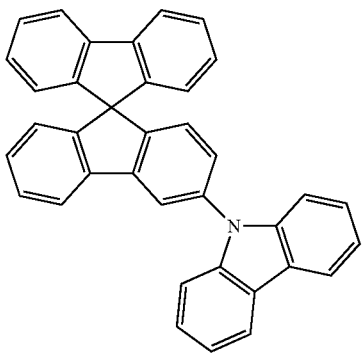

(H-116)

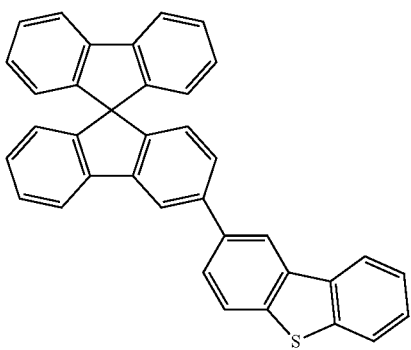

(H-117)

(H-118)

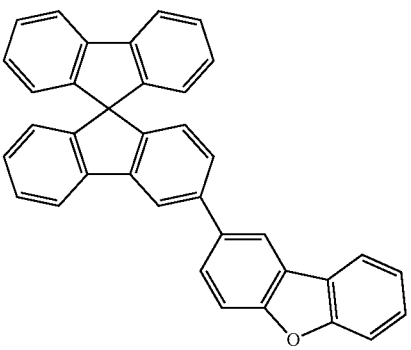

The polymer compound used as a host material includes, for example, polymer compounds as a hole transporting material described later and polymer compounds as an electron transporting material described later.

[Polymer Host]

The polymer compound which is preferable as a host compound (hereinafter, referred to as "polymer host") will be explained.

The polymer host is preferably a polymer compound comprising a constitutional unit represented by the formula (Y).

[Chemical formula 52]

$$-\!\!\!-\!\!\!\!\left[\!\!\!-Ar^{Y1}\!\!\!-\!\!\!\right]\!\!\!-\!\!\!-$$  (Y)

The arylene group represented by $Ar^{Y1}$ is more preferably a group represented by the formula (A-1), the formula (A-2), the formula (A-6) to (A-10), the formula (A-19) or the formula (A-20), further preferably a group represented by the formula (A-1), the formula (A-2), the formula (A-7), the formula (A-9) or the formula (A-19), and these groups each optionally have a substituent.

The divalent heterocyclic group represented by $Ar^{Y1}$ is more preferably a group represented by the formula (AA-1) to (AA-4), the formula (AA-10) to (AA-15), the formula (AA-18) to (AA-21), the formula (AA-33) or the formula (AA-34), further preferably a group represented by the formula (AA-4), the formula (AA-10), the formula (AA-12), the formula (AA-14) or the formula (AA-33), and these groups each optionally have a substituent.

The more preferable range and the further preferable range of the arylene group and the divalent heterocyclic group in the divalent group in which at least one arylene group and at least one divalent heterocyclic group are bonded directly to each other represented by $Ar^{Y1}$ are the same as the more preferable range and the further preferable range of the arylene group and the divalent heterocyclic group represented by $Ar^{Y1}$ described above, respectively.

"The divalent group in which at least one arylene group and at least one divalent heterocyclic group are bonded directly to each other" includes, for example, groups represented by the following formulae, and each of them optionally has a substituent.

[Chemical formula 53]

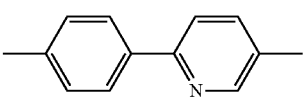

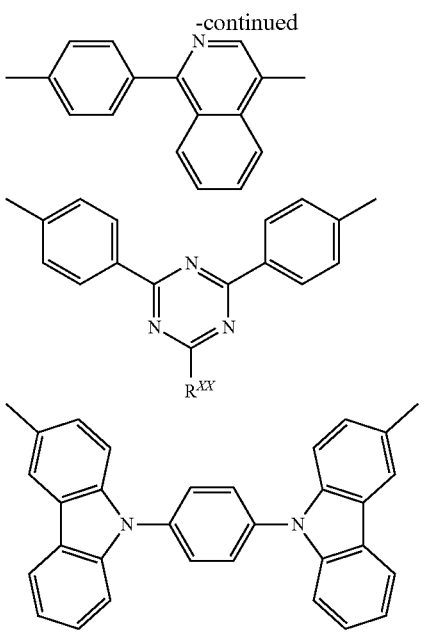

[wherein, $R^{XX}$ represents a hydrogen atom, an alkyl group, a cycloalkyl group, an aryl group or a monovalent heterocyclic group and these groups each optionally have a substituent.]

$R^{XX}$ is preferably an alkyl group, a cycloalkyl group or an aryl group, and these groups each optionally have a substituent.

The substituent which the group represented by $Ar^{Y1}$ optionally has is preferably an alkyl group, a cycloalkyl group or an aryl group, and these groups each optionally further have a substituent.

The constitutional unit represented by the formula (Y) includes, for example, constitutional units represented by the formulae (Y-1) to (Y-10), and from the standpoint of the luminance life of the light emitting device of the present invention preferable are constitutional units represented by the formulae (Y-1) to (Y-3), from the standpoint of electron transportability of the light emitting device of the present invention preferable are constitutional units represented by the formulae (Y-4) to (Y-7), and from the standpoint of hole transportability of the light emitting device of the present invention preferable are constitutional units represented by the formulae (Y-8) to (Y-10).

[Chemical formula 54]

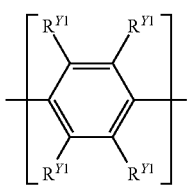

(Y-1)

[wherein, $R^{Y1}$ represents a hydrogen atom, an alkyl group, a cycloalkyl group, an alkoxy group, a cycloalkoxy group, an aryl group or a monovalent heterocyclic group, and these groups each optionally have a substituent. The plurality of $R^{Y1}$ may be the same or different, and adjacent $R^{Y1}$s may be combined together to form a ring together with the carbon atoms to which they are attached.]

$R^{Y1}$ is preferably a hydrogen atom, an alkyl group, a cycloalkyl group or an aryl group, and these groups each optionally have a substituent.

It is preferable that the constitutional unit represented by the formula (Y-1) is a constitutional unit represented by the formula (Y-1').

[Chemical formula 55]

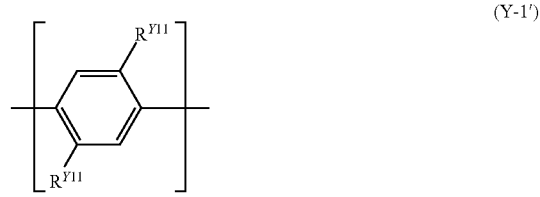

(Y-1')

[wherein, $R^{Y11}$ represents an alkyl group, a cycloalkyl group, an alkoxy group, a cycloalkoxy group, an aryl group or a monovalent heterocyclic group, and these groups each optionally have a substituent. The plurality of $R^{Y11}$ may be the same or different.]

$R^{Y11}$ is preferably an alkyl group, a cycloalkyl group or an aryl group, more preferably an alkyl group or a cycloalkyl group, and these groups each optionally have a substituent.

[Chemical formula 56]

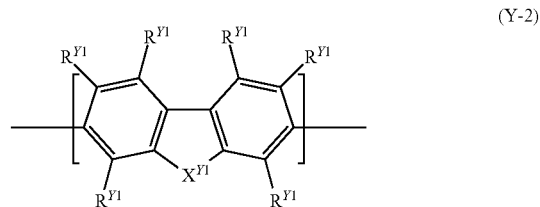

(Y-2)

[wherein, $R^{Y1}$ represents the same meaning as described above. $X^{Y1}$ represents a group represented by —C($R^{Y2}$)$_2$—, —C($R^{Y2}$)=C($R^{Y2}$)— or —C($R^{Y2}$)$_2$—C($R^{Y2}$)$_2$—. $R^{Y2}$ represents a hydrogen atom, an alkyl group, a cycloalkyl group, an alkoxy group, a cycloalkoxy group, an aryl group or a monovalent heterocyclic group and these groups each optionally have a substituent. The plurality of $R^{Y2}$ may be the same or different, and these $R^{Y2}$s may be combined together to form a ring together with the carbon atoms to which they are attached.]

$R^{Y2}$ is preferably an alkyl group, a cycloalkyl group, an aryl group or a monovalent heterocyclic group, more preferably an alkyl group a cycloalkyl group or an aryl group, and these groups each optionally have a substituent.

Regarding the combination of two $R^{Y2}$s in the group represented by —C($R^{Y2}$)$_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, and these groups each optionally have a substituent. The two groups $R^{Y2}$ may be combined together to form a ring together with the atoms to which they are attached, and when the groups $R^{Y2}$ form a ring, the group represented by —C(R$^{Y2}$)$_2$— is preferably a group represented by the formula (Y-A1) to (Y-A5), more preferably a group represented by the formula (Y-A4), and these groups each optionally have a substituent.

[Chemical formula 57]

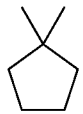
(Y-A1)

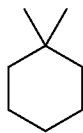
(Y-A2)

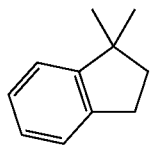
(Y-A3)

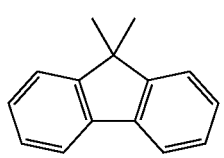
(Y-A4)

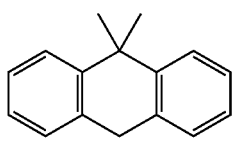
(Y-A5)

Regarding the combination of two R$^{Y2}$s in the group represented by —C(R$^{Y2}$)=C(R$^{Y2}$)— in X$^{Y1}$, it is preferable that the both are an alkyl group or cycloalkyl group, or one is an alkyl group or a cycloalkyl group and the other is an aryl group, and these groups each optionally have a substituent.

Four R$^{Y2}$s in the group represented by —C(R$^{Y2}$)$_2$—C(R$^{Y2}$)$_2$— in X$^{Y1}$ are preferably an alkyl group or a cycloalkyl group each optionally having a substituent. The plurality of R$^{Y2}$ may be combined together to form a ring together with the atoms to which they are attached, and when the groups R$^{Y2}$ form a ring, the group represented by —C(R$^{Y2}$)$_2$—C(R$^{Y2}$)$_2$— is preferably a group represented by the formula (Y-B1) to (Y-B5), more preferably a group represented by the formula (Y-B3), and these groups each optionally have a substituent.

[Chemical formula 58]

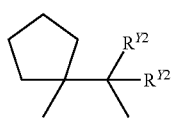
(Y-B1)

-continued

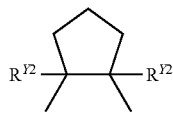
(Y-B2)

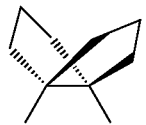
(Y-B3)

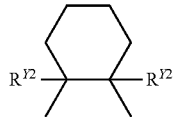
(Y-B4)

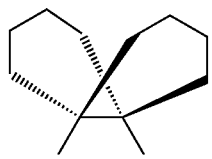
(Y-B5)

[wherein, R$^{Y2}$ represents the same meaning as described above.]

It is preferable that the constitutional unit represented by the formula (Y-2) is a constitutional unit represented by the formula (Y-2').

[Chemical formula 59]

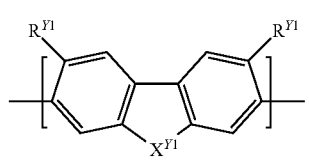
(Y-2')

[wherein, R$^{Y1}$ and X$^{Y1}$ represent the same meaning as described above.]

[Chemical formula 60]

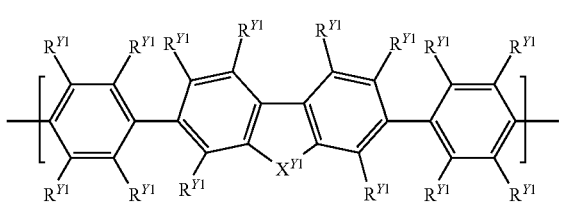
(Y-3)

[wherein, R$^{Y1}$ and X$^{Y1}$ represent the same meaning as described above.]

It is preferable that the constitutional unit represented by the formula (Y-3) is a constitutional unit represented by the formula (Y-3').

[Chemical formula 61]

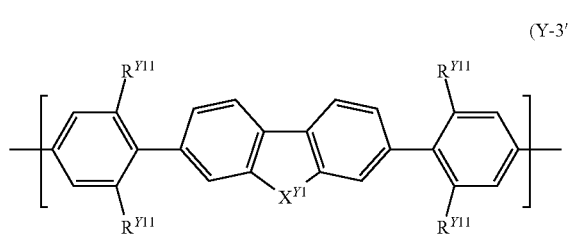
(Y-3')

[wherein, $R^{Y11}$ and $X^{Y1}$ represent the same meaning as described above.]

[Chemical formula 62]

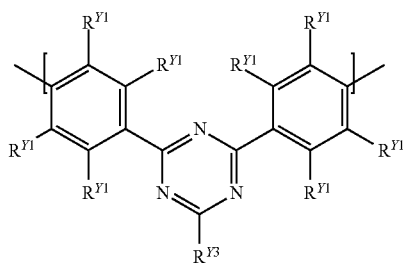
(Y-4)

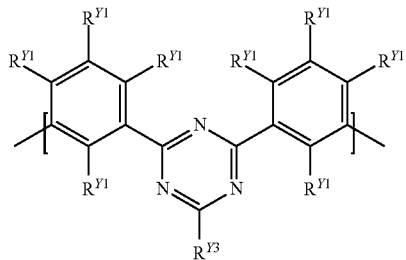
(Y-5)

[Chemical formula 63]

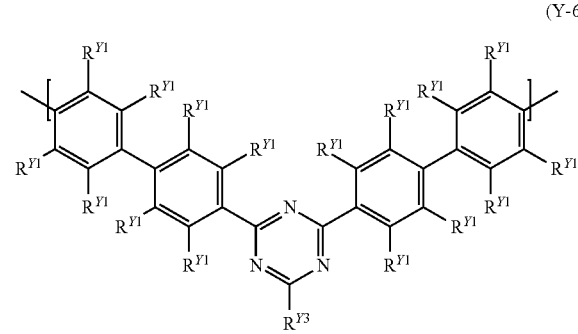
(Y-6)

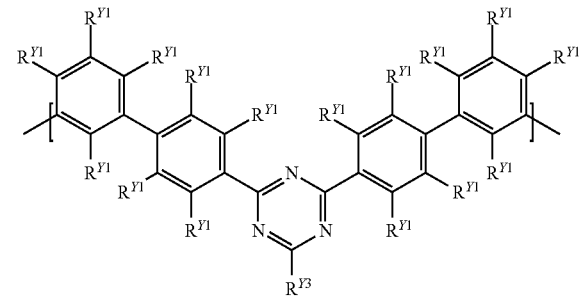
(Y-7)

[wherein, $R^{Y1}$ represents the same meaning as described above. $R^{Y3}$ represents a hydrogen atom, an alkyl group, a cycloalkyl group, an alkoxy group, a cycloalkoxy group, an aryl group or a monovalent heterocyclic group and these groups each optionally have a substituent.]

$R^{Y3}$ is preferably an alkyl group, a cycloalkyl group, an alkoxy group, a cycloalkoxy group, an aryl group or a monovalent heterocyclic group, more preferably an aryl group, and these groups each optionally have a substituent.

It is preferable that the constitutional unit represented by the formula (Y-4) is a constitutional unit represented by the formula (Y-4'), and it is preferable that the constitutional unit represented by the formula (Y-6) is a constitutional unit represented by the formula (Y-6').

[Chemical formula 64]

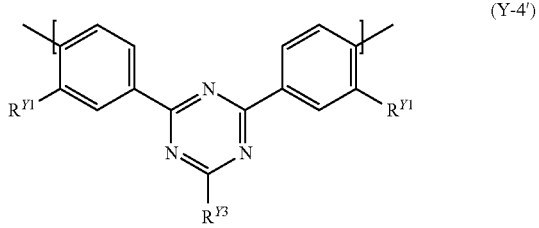
(Y-4')

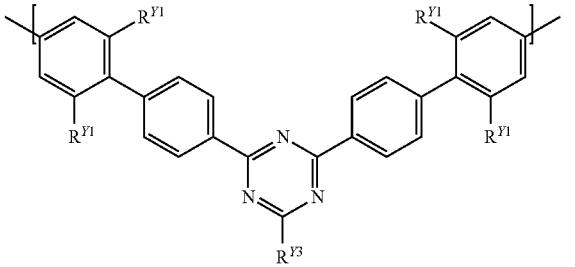
(Y-6')

[wherein, $R^{Y1}$ and $R^{Y3}$ represent the same meaning as described above.]

[Chemical formula 65]

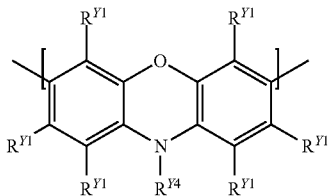
(Y-8)

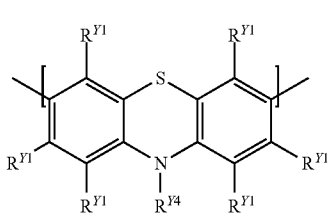
(Y-9)

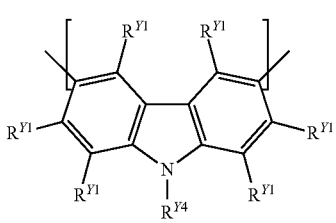
(Y-10)

[wherein, $R^{Y1}$ represents the same meaning as described above. $R^{Y4}$ represents a hydrogen atom, an alkyl group, a cycloalkyl group, an alkoxy group, a cycloalkoxy group, an aryl group or a monovalent heterocyclic group, and these groups each optionally have a substituent.]

$R^{Y4}$ is preferably an alkyl group, a cycloalkyl group, an alkoxy group, a cycloalkoxy group, an aryl group or a monovalent heterocyclic group, more preferably an aryl group, and these groups each optionally have a substituent.

The constitutional unit represented by the formula (Y) includes, for example, a constitutional unit composed of an arylene group represented by the formula (Y-101) to (Y-121), a constitutional unit composed of a divalent heterocyclic group represented by the formula (Y-201) to (Y-206), and a constitutional unit composed of a divalent group in which at least one arylene group and at least one divalent heterocyclic group are bonded directly to each other represented by the formula (Y-301) to (Y-304).

[Chemical formula 66]

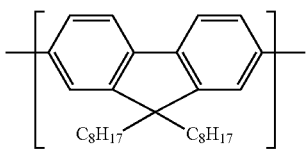
(Y-101)

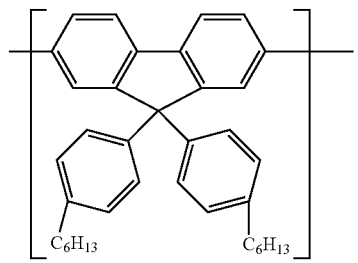
(Y-102)

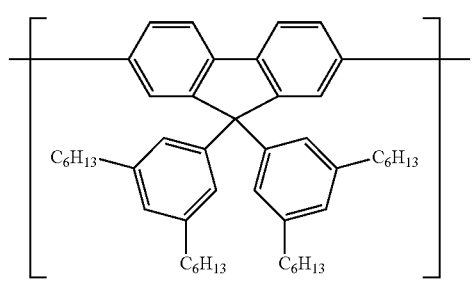
(Y-103)

[Chemical formula 67]

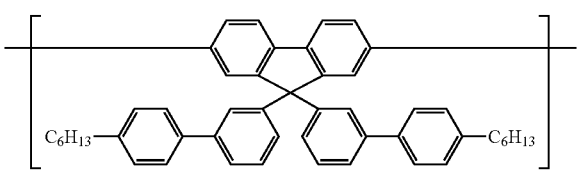
(Y-104)

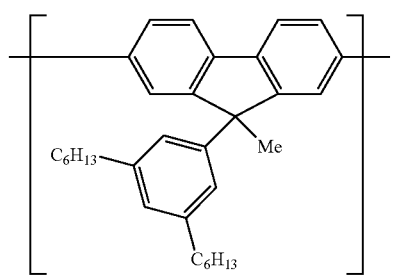
(Y-105)

[Chemical formula 68]

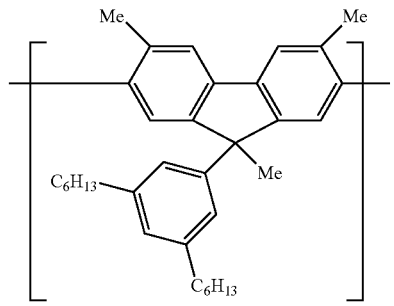
(Y-106)

-continued
(Y-107)
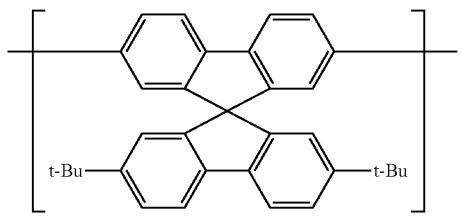
(Y-108)
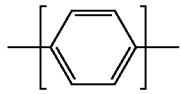
(Y-109)
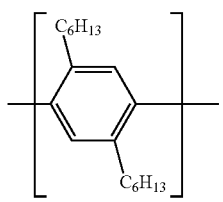
[Chemical formula 69]
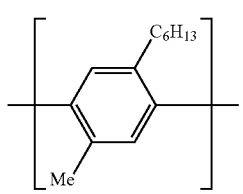
(Y-110)
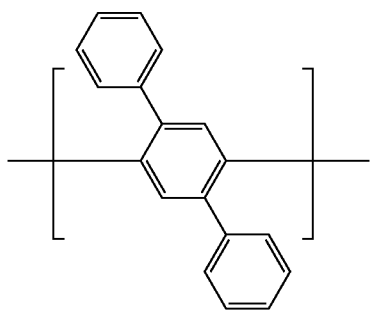
(Y-111)
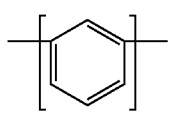
(Y-112)
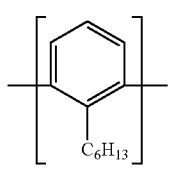
(Y-113)
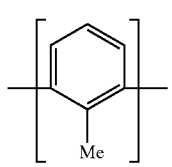
[Chemical formula 70]
(Y-114)
(Y-115)
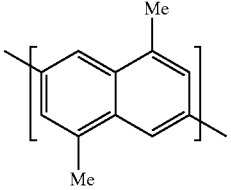
(Y-116)
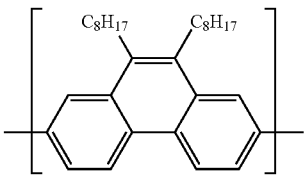
(Y-117)
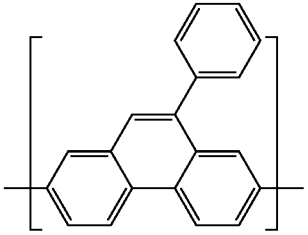
(Y-118)
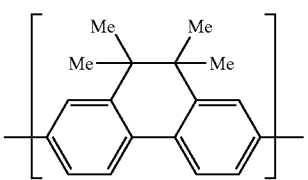
[Chemical formula 71]
(Y-119)
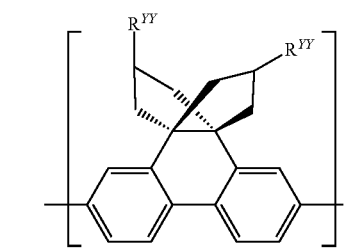
$R^{YY}=$ 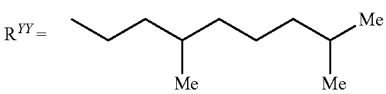
(Y-120)
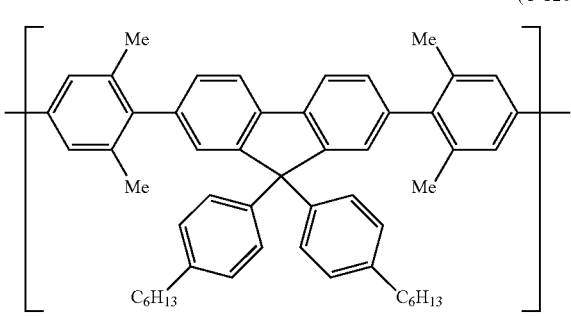

(Y-121)
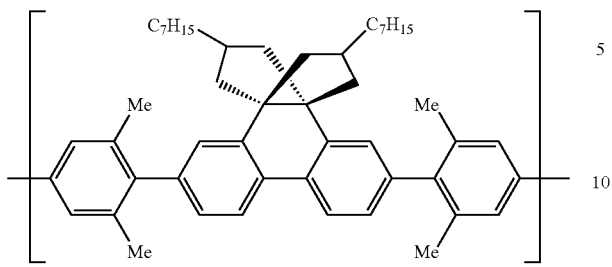
[Chemical formula 72]
(Y-201)
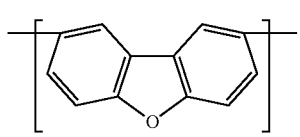
(Y-202)
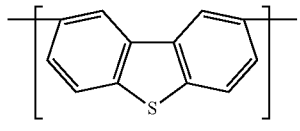
(Y-203)
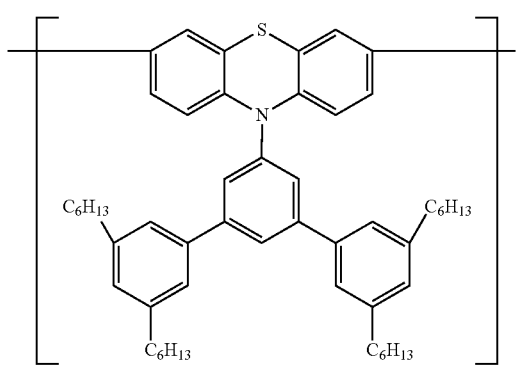
(Y-204)
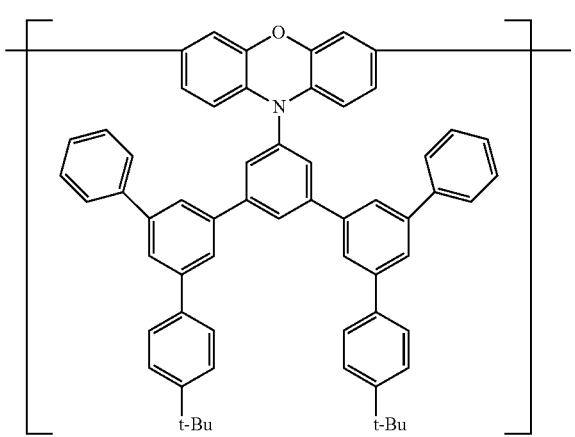
[Chemical formula 73]
(Y-205)
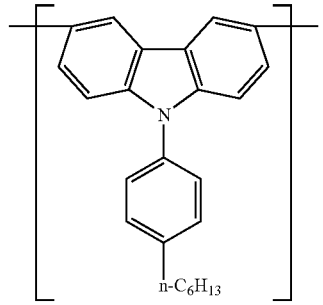
(Y-206)
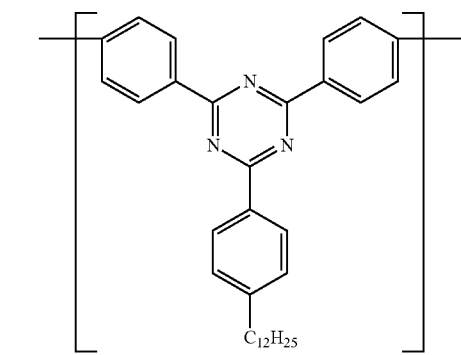
(Y-301)
(Y-302)
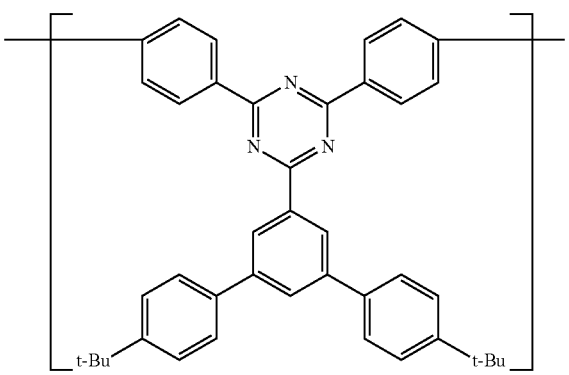
[Chemical formula 74]

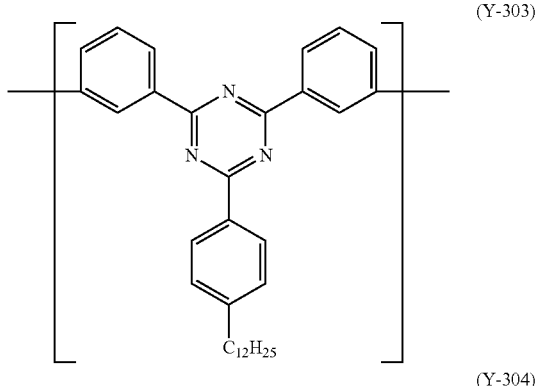

(Y-303)

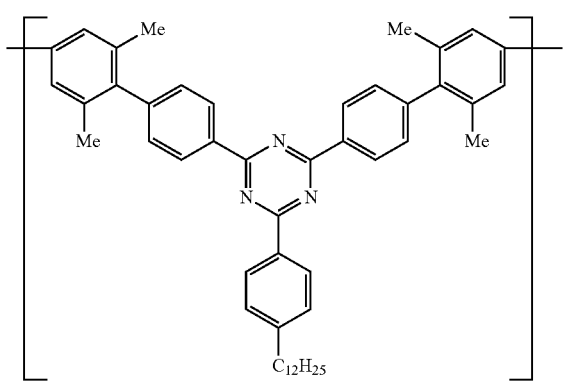

(Y-304)

The amount of the constitutional unit represented by the formula (Y) in which $Ar^{Y1}$ is an arylene group is preferably 0.5 to 80 mol %, more preferably 30 to 60 mol % with respect to the total amount of constitutional units contained in a polymer compound, because the luminance life of the light emitting device of the present invention is excellent.

The amount of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 30 mol %, more preferably 3 to 20 mol % with respect to the total amount of constitutional units contained in a polymer compound, because the charge transportability of the light emitting device of the present invention is excellent.

The constitutional unit represented by the formula (Y) may be contained only singly or two or more units thereof may be contained in the polymer host.

It is preferable that the polymer host further comprises a constitutional unit represented by the following formula (X), because hole transportability is excellent.

[Chemical formula 75]

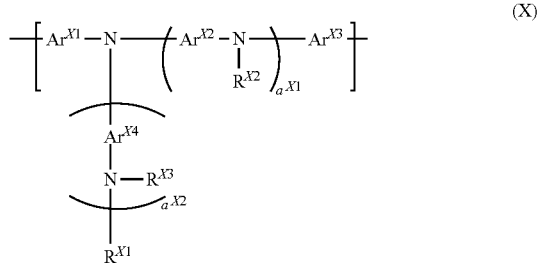

(X)

[wherein, $a^{X1}$ and $a^{X2}$ each independently represent an integer of 0 or more.

$Ar^{X1}$ and $Ar^{X3}$ each independently represent an arylene group or a divalent heterocyclic group, and these groups each optionally have a substituent.

$Ar^{X2}$ and $Ar^{X4}$ each independently represent an arylene group, a divalent heterocyclic group or a divalent group in which at least one arylene group and at least one divalent heterocyclic group are bonded directly to each other, and these groups each optionally have a substituent.

$R^{X1}$, $R^{X2}$ and $R^{X3}$ each independently represent a hydrogen atom, an alkyl group, a cycloalkyl group, an aryl group or a monovalent heterocyclic group, and these groups each optionally have a substituent.]

$a^{X1}$ is preferably 2 or less, more preferably 1, because the luminance life of the light emitting device of the present invention is excellent.

$a^{X2}$ is preferably 2 or less, more preferably 0, because the luminance life of the light emitting device of the present invention is excellent.

$R^{X1}$, $R^{X2}$ and $R^{X3}$ are preferably an alkyl group, a cycloalkyl group, an aryl group or a monovalent heterocyclic group, more preferably an aryl group, and these groups each optionally have a substituent.

The arylene group represented by $Ar^{X1}$ and $Ar^{X3}$ is more preferably a group represented by the formula (A-1) or the formula (A-9), further preferably a group represented by the formula (A-1), and these groups each optionally have a substituent.

The divalent heterocyclic group represented by $Ar^{X1}$ and $Ar^{X3}$ is more preferably a group represented by the formula (AA-1), the formula (AA-2) or the formula (AA-7) to (AA-26), and these groups each optionally have a substituent.

$Ar^{X1}$ and $Ar^{X3}$ are preferably an arylene group optionally having a substituent.

The arylene group represented by $Ar^{X2}$ and $Ar^{X4}$ is more preferably a group represented by the formula (A-1), the formula (A-6), the formula (A-7), the formula (A-9) to (A-11) or the formula (A-19), and these groups each optionally have a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by $Ar^{X1}$ and $Ar^{X3}$, respectively.

The divalent group in which at least one arylene group and at least one divalent heterocyclic group are bonded directly to each other represented by $Ar^{X2}$ and $Ar^{X4}$ includes the same groups as the divalent group in which at least one arylene group and at least one divalent heterocyclic group are bonded directly to each other represented by $Ar^{Y1}$ in the formula (Y).

$Ar^{X2}$ and $Ar^{X4}$ are preferably an arylene group optionally having a substituent.

The substituent which the group represented by $Ar^{X1}$ to $Ar^{X4}$ and $R^{X1}$ to $R^{X3}$ optionally has is preferably an alkyl group, a cycloalkyl group or an aryl group, and these groups each optionally further have a substituent.

The constitutional unit represented by the formula (X) is preferably a constitutional unit represented by the formula (X-1) to (X-7), more preferably a constitutional unit represented by the formula (X-1) to (X-6), further preferably a constitutional unit represented by the formula (X-3) to (X-6).

[Chemical formula 76]

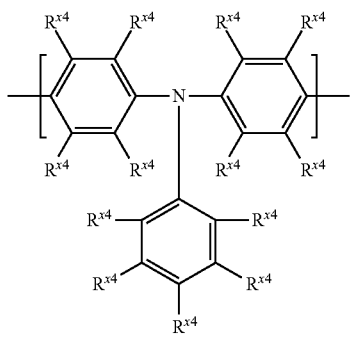
(X-1)

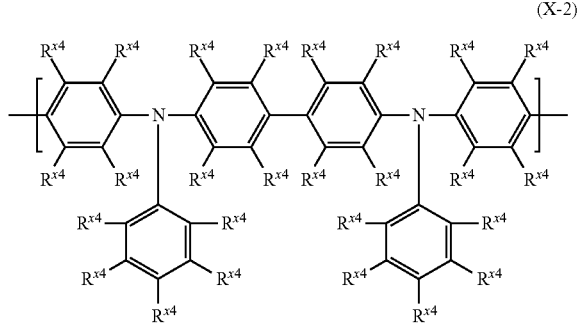
(X-2)

[Chemical formula 77]

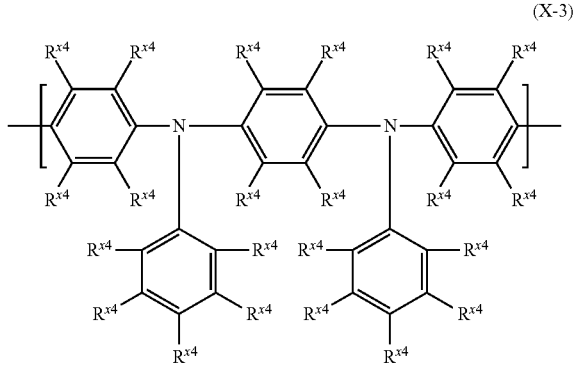
(X-3)

[Chemical formula 78]

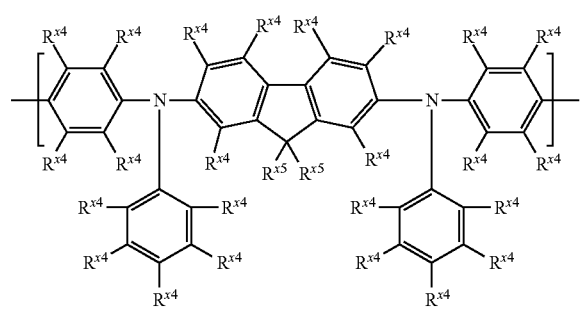
(X-4)

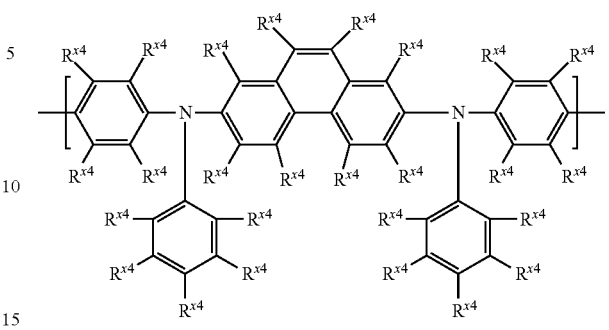
(X-5)

[Chemical formula 79]

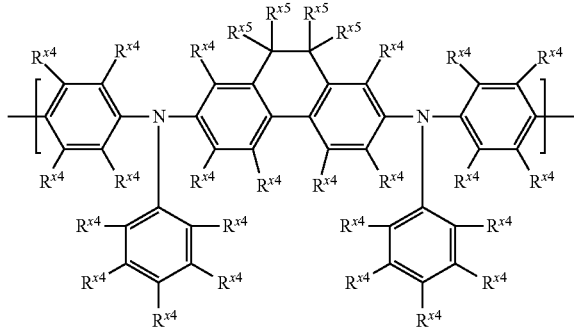
(X-6)

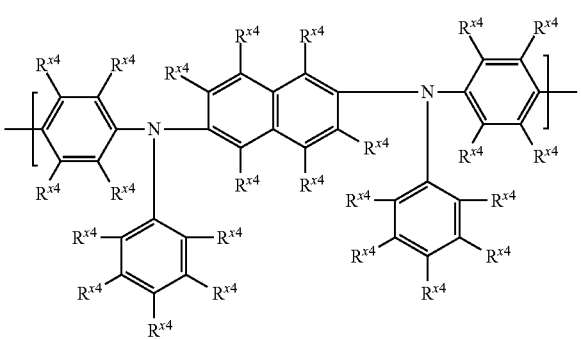
(X-7)

[wherein, $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, and these groups each optionally have a substituent. The plurality of $R^{X4}$ may be the same or different. The plurality of $R^{X5}$ may be the same or different, and adjacent groups $R^{X5}$ may be combined together to form a ring together with the carbon atoms to which they are attached.]

The amount of the constitutional unit represented by the formula (X) is preferably 0.1 to 50 mol %, more preferably 1 to 40 mol %, further preferably 5 to 30 mol % with respect to the total amount of constitutional units contained in a polymer host, because hole transportability is excellent.

The constitutional unit represented by the formula (X) includes, for example, constitutional units represented by the formulae (X1-1) to (X1-11), preferably constitutional units represented by the formulae (X1-3) to (X1-10).

[Chemical formula 80]
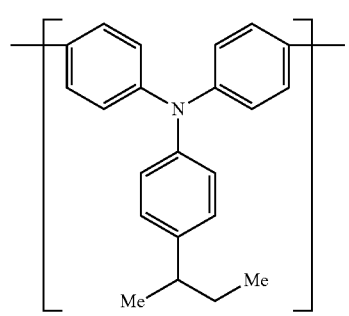
(X1-1)
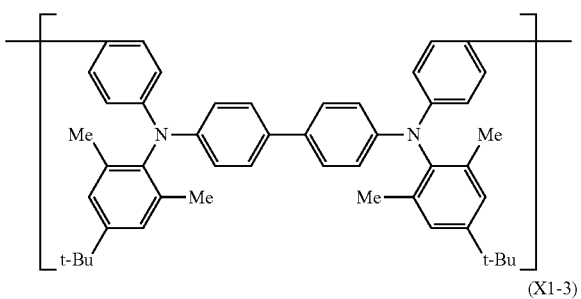
(X1-2)
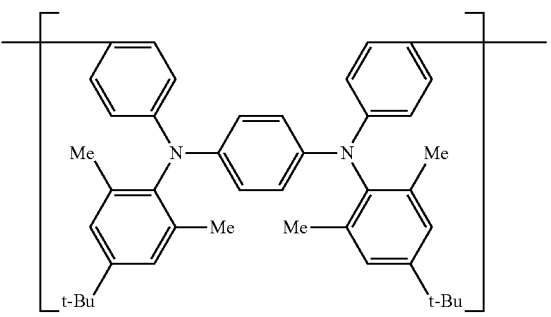
(X1-3)
[Chemical formula 81]
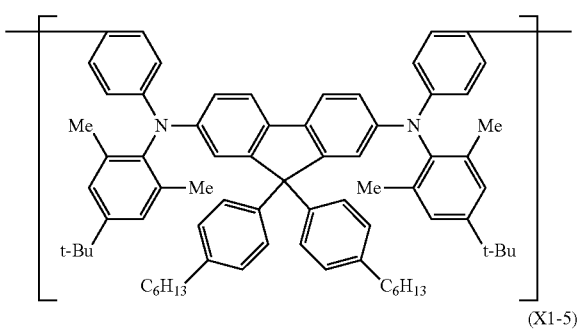
(X1-4)
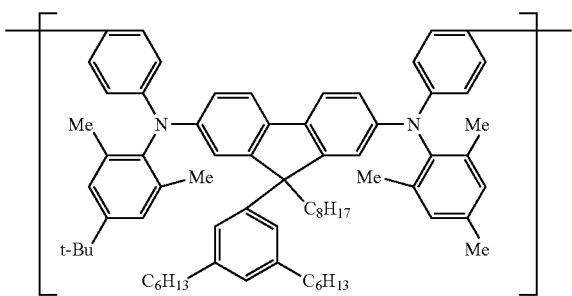
(X1-5)
[Chemical formula 82]
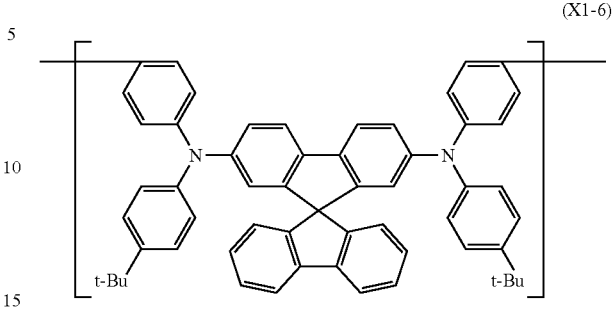
(X1-6)
(X1-7)
[Chemical formula 83]
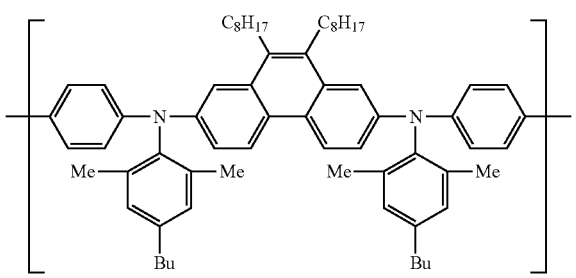
(X1-8)
(X1-9)
[Chemical formula 84]
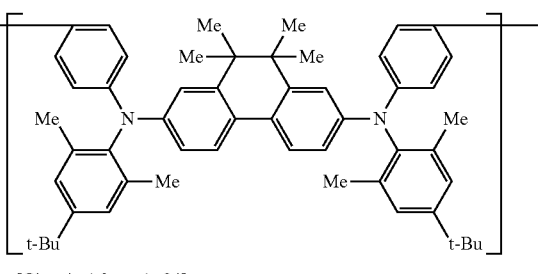
(X1-10)

-continued (X1-11)

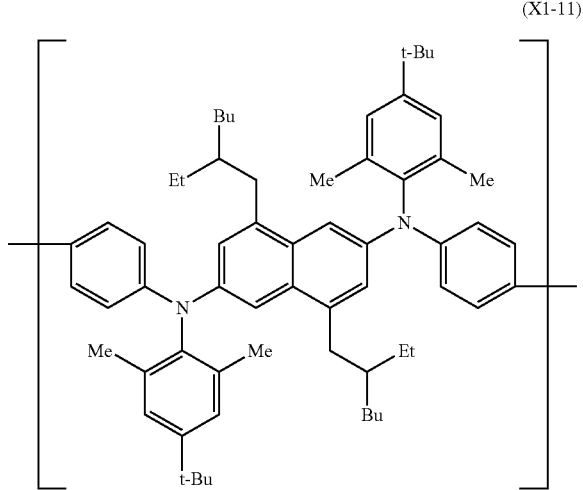

The constitutional unit represented by the formula (X) may be contained only singly or two or more units thereof may be contained in the polymer host.

Examples of the polymer host include polymer compounds (P-1) to (P-6) in the Table 1.

TABLE 1

| | constitutional unit and mole fraction thereof | | | | |
|---|---|---|---|---|---|
| | formula (Y) | | | formula (X) | |
| polymer compound | formulae (Y-1) to (Y-3) p | formulae (Y-4) to (Y-7) q | formulae (Y-8) to (Y-10) r | formulae (X-1) to (X-7) s | other t |
| (P-1) | 0.1 to 99.9 | 0.1 to 99.9 | 0 | 0 | 0 to 30 |
| (P-2) | 0.1 to 99.9 | 0 | 0.1 to 99.9 | 0 | 0 to 30 |
| (P-3) | 0.1 to 99.8 | 0.1 to 99.8 | 0 | 0.1 to 99.8 | 0 to 30 |
| (P-4) | 0.1 to 99.8 | 0.1 to 99.8 | 0.1 to 99.8 | 0 | 0 to 30 |
| (P-5) | 0.1 to 99.8 | 0 | 0.1 to 99.8 | 0.1 to 99.8 | 0 to 30 |
| (P-6) | 0.1 to 99.7 | 0.1 to 99.7 | 0.1 to 99.7 | 0.1 to 99.7 | 0 to 30 |

[In the table, p, q, r, s and t represent the mole fraction of each constitutional unit. p+q+r+s+t=100, and 100≥p+q+r+s≥70. Other constitutional unit denotes a constitutional unit other than the constitutional unit represented by the formula (Y) and the constitutional unit represented by the formula (X).]

The polymer host may be any of a block copolymer, a random copolymer, an alternating copolymer or a graft copolymer, and may also be another embodiment, and is preferably a copolymer produced by copolymerizing a plurality of raw material monomers.

<Production Method of Polymer Host>

The polymer host can be produced by using a known polymerization method described in Chem. Rev., vol. 109, p p. 897-1091 (2009) and the like, exemplified are methods of causing polymerization by a coupling reaction using a transition metal catalyst such as the Suzuki reaction, the Yamamoto reaction, the Buchwald reaction, the Stille reaction, the Negishi reaction and the Kumada reaction.

In the above-described polymerization method, the method of charging monomers includes, for example, a method in which the total amount of monomers is charged in a lump into the reaction system, a method in which monomers are partially charged and reacted, then, the remaining monomers are charged in a lump, continuously or in divided doses, and a method in which monomers are charged continuously or in divided doses.

The transition metal catalyst includes a palladium catalyst, a nicked catalyst and the like.

For the post treatment of the polymerization reaction, known methods, for example, a method of removing water-soluble impurities by liquid-separation, a method in which the reaction solution after the polymerization reaction is added to a lower alcohol such as methanol to cause deposition of a precipitate which is then filtrated before drying, and other methods, are used each singly or combined. When the purity of the polymer host is low, the polymer host can be purified by usual methods such as, for example, recrystallization, reprecipitation, continuous extraction with a Soxhlet extractor and column chromatography.

[Composition of First Organic Layer]

The first organic layer may be a layer formed by using a composition comprising one or more phosphorescent compounds and at least one material selected from the group consisting of a host material, a hole transporting material, a hole injection material, an electron transporting material, an electron injection material, a light emitting material (different from a phosphorescent compound), an antioxidant and a solvent described above (hereinafter, referred to also as "composition of first organic layer"). That is, the first organic layer may be a layer comprising one or more phosphorescent compounds and at least one material selected from the group consisting of a host material, a hole transporting material, a hole injection material, an electron transporting material, an electron injection material, a light emitting material (different from a phosphorescent compound) and an antioxidant described above.

[Hole Transporting Material]

The hole transporting material is classified into low molecular weight compounds and polymer compounds, and polymer compounds are preferable. The hole transporting material optionally has a crosslinkable group.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetracyanoquinodimethane, tetracyanoethylene, trinitrofluorenone and the like, preferably fullerene.

In the composition of the first organic layer, the compounding amount of the hole transporting material is usually 1 to 400 parts by weight, preferably 5 to 150 parts by weight when the content of the phosphorescent compound is 100 parts by weight.

The hole transporting material may be used singly, or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, diphenoquinone and derivatives thereof.

The polymer compound includes, for example, polyphenylene, polyfluorene and derivatives thereof. These polymer compounds may be doped with a metal.

In the composition of the first organic layer, the compounding amount of the electron transporting material is usually 1 to 400 parts by weight, preferably 5 to 150 parts by weight when the content of the phosphorescent compound is 100 parts by weight.

The electron transporting material may be used singly, or two or more electron transporting materials may be used in combination.

[Hole Injection Material and Electron Injection Material]

The hole injection material and the electron injection material are each classified into low molecular weight compounds and polymer compounds. The hole injection material and the electron injection material each optionally have a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising an aromatic amine structure in the main chain or side chain.

In the composition of the first organic layer, the compounding amounts of the hole injection material and the electron injection material are each usually 1 to 400 parts by weight, preferably 5 to 150 parts by weight when the content of the phosphorescent compound is 100 parts by weight.

The hole injection material and the electron injection material may each be used singly, or two or more of them may be used in combination.

[Ion Dope]

When the hole injection material or the electron injection material comprises an electrically conductive polymer, the electric conductivity of the electrically conductive polymer is preferably $1 \times 10^{-5}$ S/cm to $1 \times 10^3$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly, or two or more ions to be doped may be used.

[Light Emitting Material]

The light emitting material (different from a phosphorescent compound) is classified into low molecular weight compounds and polymer compounds. The light emitting material optionally has a crosslinkable group.

The low molecular weight compound includes, for example, naphthalene and derivatives thereof, anthracene and derivatives thereof, and perylene and derivatives thereof.

The polymer compound includes, for example, polymer compounds comprising a phenylene group, a naphthalenediyl group, an anthracenediyl group, a fluorenediyl group, a phenanthrenediyl group, dihydrophenanthrenediyl group, a group represented by the formula (X), a carbazolediyl group, a phenoxazinediyl group, a phenothiazinediyl group, a pyrenediyl group and the like.

In the composition of the first organic layer, the compounding amount of the light emitting material is usually 1 to 400 parts by weight, preferably 5 to 150 parts by weight when the content of the phosphorescent compound is 100 parts by weight.

The light emitting material may be used singly, or two or more light emitting materials may be used in combination.

[Antioxidant]

The antioxidant may advantageously be one which is soluble in the same solvent as for a phosphorescent compound and does not disturb light emission and charge transportation, and the examples thereof include phenol-based antioxidants and phosphorus-based antioxidants.

In the composition of the first organic layer, the compounding amount of the antioxidant is usually 0.001 to 10 parts by weight when the content of the phosphorescent compound is 100 parts by weight.

The antioxidant may be used singly, or two or more antioxidants may be used in combination.

[Ink of First Organic Layer]

The composition of the first organic layer comprising a solvent (hereinafter, referred to also as "ink of first organic layer".) can be suitably used in application methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet printing method, a capillary coat method and a nozzle coat method.

The viscosity of the ink of the first organic layer may be adjusted depending on the kind of the application method, and when a solution goes through a discharge apparatus such as in an inkjet printing method, the viscosity is preferably in the range of 1 to 20 mPa·s at 25° C. because curved aviation and clogging in discharging are unlikely.

As the solvent contained in the ink of the first organic layer, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as THF, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; poly-hydric alcohol solvents such as ethylene glycol, glycerin and 1,2-hexanediol and derivatives thereof; alcohol solvents such as isopropylalcohol and cyclohexanol; sulfoxide solvents such as dimethyl sulfoxide; and amide solvents such as N-methyl-2-pyrrolidone and N,N-dimethylformamide. These solvents may be used singly, or two or more of them may be used in combination.

In the ink of the first organic layer, the compounding amount of the solvent is usually 1000 to 100000 parts by weight, preferably 2000 to 20000 parts by weight when the content of the phosphorescent compound is 100 parts by weight.

<Second Organic Layer>

The second organic layer is a layer formed by using a composition comprising one or more phosphorescent compounds and a crosslinkable material. As described above, the second organic layer is preferably a layer comprising one or more phosphorescent compounds and a crosslinked body of a crosslinkable material.

[Phosphorescent Compound]

The phosphorescent compound used for formation of the second organic layer is preferably a phosphorescent compound represented by the formula (1). Also the phosphorescent compound used for formation of the first organic layer described above is preferably a phosphorescent compound represented by the formula (1). At least one phosphorescent compound used for formation of the second organic layer and at least one phosphorescent compound used for formation of the first organic layer are the same phosphorescent compound represented by the formula (1)

The definition and the examples of the phosphorescent compound represented by the formula (1) used for formation of the second organic layer are the same as the definition and the examples of the phosphorescent compound represented by the formula (1) used for formation of the first organic layer.

At least one phosphorescent compound used for formation of the second organic layer is a phosphorescent compound represented by the formula (1) (the same phosphorescent compound as at least one phosphorescent compound used for formation of the first organic layer), and the second organic layer may be a layer formed by using a phosphorescent compound represented by the formula (1) and other phosphorescent compound together, or may be a layer comprising a phosphorescent compound represented by the formula (1) and other phosphorescent compound. Examples of the other phosphorescent compound used for formation of the second organic layer are the same as examples of the other phosphorescent compound used for formation of the first organic layer.

[Crosslinkable Material]

The crosslinkable material may be a low molecular weight compound or a polymer compound, and is preferably a material having at least one crosslinkable group selected from Group A of crosslinkable group, and preferably a polymer compound comprising a crosslinkable constitutional unit having at least one crosslinkable group selected from Group A of crosslinkable group (hereinafter, referred to also as "polymer compound of second organic layer"), because the light emitting device of the present invention is excellent in light emission efficiency.

The crosslinkable group selected from Group A of crosslinkable group is preferably a crosslinkable group represented by the formula (XL-1), (XL-3), (XL-9), (XL-16) or (XL-17), more preferably a crosslinkable group represented by the formula (XL-1), (XL-16) or (XL-17), further preferably a crosslinkable group represented by the formula (XL-1) or (XL-17), because the light emitting device of the present invention is more excellent in luminance life.

The low molecular weight compound having at least one crosslinkable group selected from Group A of crosslinkable group includes, for example, low molecular weight compounds shown below.

[Chemical formula 85]

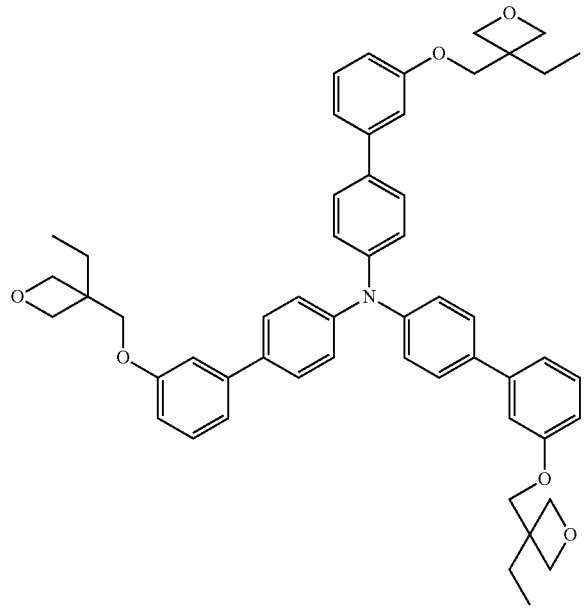

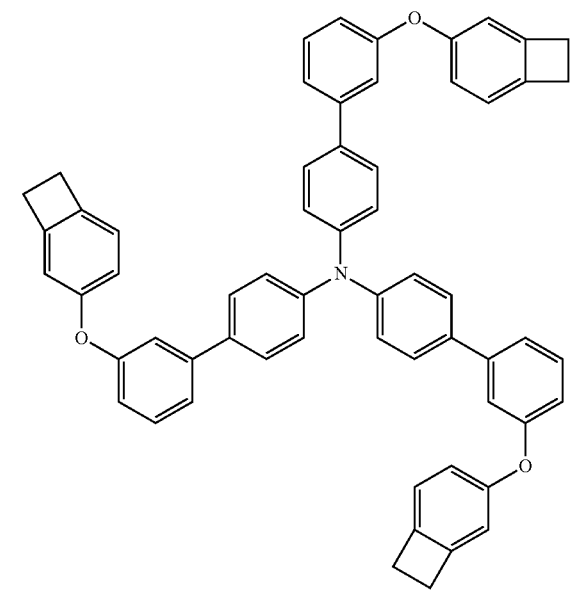

-continued

[Chemical formula 85]

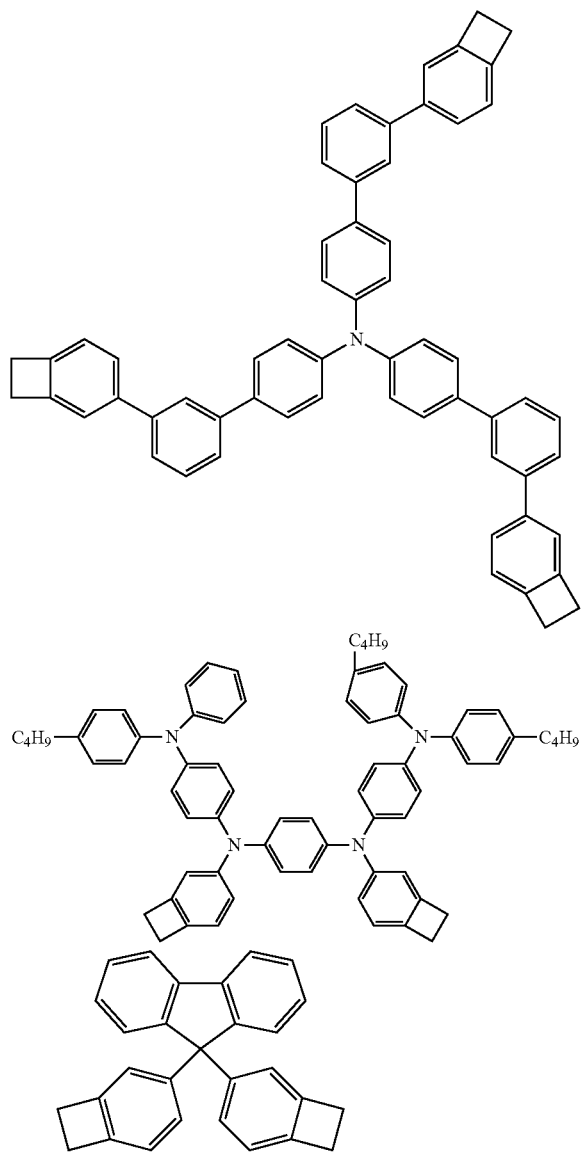

The crosslinkable constitutional unit having at least one crosslinkable group selected from Group A of crosslinkable group contained in the polymer compound of the second organic layer is preferably a constitutional unit represented by the formula (3) or a constitutional unit represented by the formula (4) described later, and may also be a constitutional unit represented by the following formula.

[Chemical formula 86]

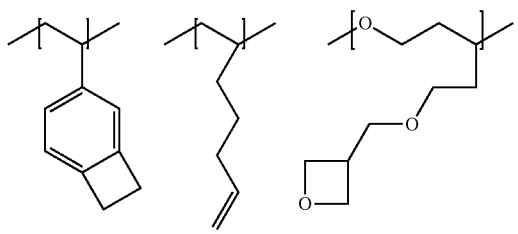

-continued

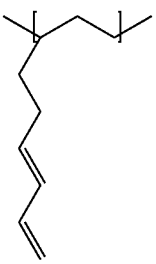

The crosslinkable constitutional unit having at least one crosslinkable group selected from Group A of crosslinkable group contained in the polymer compound of the second organic layer is preferably a constitutional unit represented by the formula (3) or a constitutional unit represented by the formula (4).

[Chemical formula 87]

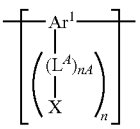

(3)

nA is preferably 0 to 1, more preferably 0, because the light emitting device of the present invention is excellent in light emission efficiency.

n is preferably 2, because the light emitting device of the present invention is excellent in light emission efficiency.

$Ar^1$ is preferably an aromatic hydrocarbon group optionally having a substituent, because the light emitting device of the present invention is excellent in light emission efficiency.

The number of carbon atoms of the aromatic hydrocarbon group represented by $Ar^1$, not including the number of carbon atoms of a substituent, is usually 6 to 60, preferably 6 to 30, more preferably 6 to 18.

The arylene group portion obtained by removing n substituents of the aromatic hydrocarbon group represented by $Ar^1$ is preferably a group represented by the formula (A-1) to the formula (A-20), more preferably a group represented by the formula (A-1), the formula (A-2), the formula (A-6) to the formula (A-10), the formula (A-19) or the formula (A-20), further preferably a group represented by the formula (A-1), the formula (A-2), the formula (A-7), the formula (A-9) or the formula (A-19), and these groups each optionally have a substituent.

The number of carbon atoms of the heterocyclic group represented by $Ar^1$, not including the number of carbon atoms of a substituent, is usually 6 to 60, preferably 6 to 30, more preferably 6 to 18.

The divalent heterocyclic group portion obtained by removing n substituents of the heterocyclic group represented by $Ar^1$ is preferably a group represented by the formula (AA-1) to the formula (AA-34).

The aromatic hydrocarbon group and the heterocyclic group represented by $Ar^1$ each optionally have a substituent, and the substituent which the aromatic hydrocarbon group and the heterocyclic group optionally have includes, for example, an alkyl group, a cycloalkyl group, an alkoxy group, a cycloalkoxy group, an aryl group, an aryloxy group, a halogen atom, a monovalent heterocyclic group and a cyano group.

The number of carbon atoms of the alkylene group represented by $L^A$, not including the number of carbon atoms of a substituent, is usually 1 to 10, preferably 1 to 5, more preferably 1 to 3. The number of carbon atoms of the cycloalkylene group represented by $L^A$, not including the number of carbon atoms of a substituent, is usually 3 to 10.

The alkylene group and the cycloalkylene group each optionally have a substituent, and the substituent includes, for example, a methylene group, an ethylene group, a propylene group, a butylene group, a hexylene group, a cyclohexylene group and an octylene group.

The alkylene group and the cycloalkylene group represented by $L^A$ each optionally have a substituent. The substituent which the alkylene group and the cycloalkylene group optionally have includes, for example, an alkyl group, a cycloalkyl group, an alkoxy group, a cycloalkoxy group, a halogen atom and a cyano group.

The aryl group represented by $L^A$ optionally has a substituent. The aryl group includes, for example, an o-phenylene group, a m-phenylene group and a p-phenylene group. The substituent which the aryl group optionally has includes, for example, an alkyl group, a cycloalkyl group, an alkoxy group, a cycloalkoxy group, an aryl group, an aryloxy group, a monovalent heterocyclic group, a halogen atom, a cyano group and a crosslinkable group selected from Group A of crosslinkable group.

$L^A$ is preferably a phenylene group or a methylene group, because production of the polymer compound of the second organic layer is easy, and these groups each optionally have a substituent.

The preferable range, the more preferable range and the further preferable range of the crosslinkable group represented by X are the same as the preferable range, the more preferable range and the further preferable range of the crosslinkable group selected from the above-described Group A of crosslinkable group.

The amount of the constitutional unit represented by the formula (3) is preferably 0.5 to 25 mol %, more preferably 3 to 25 mol %, further preferably 3 to 20 mol %, with respect to the total amount of constitutional units contained in the polymer compound of the second organic layer, because the polymer compound of the second organic layer is excellent in crosslinkability.

The constitutional unit represented by the formula (3) may be contained singly or two or more of the constitutional units may be contained in the polymer compound of the second organic layer.

[Chemical formula 88]

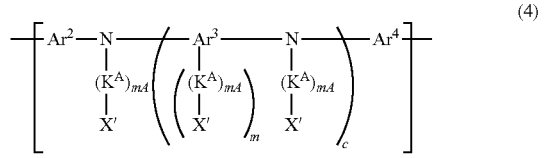

(4)

mA is preferably 0 or 1, more preferably 0, because the light emitting device of the present invention is excellent in light emission efficiency.

m is preferably 2, because the light emitting device of the present invention is excellent in light emission efficiency.

c is preferably 0, because production of the polymer compound of the second organic layer is easy and because the light emitting device of the present invention is excellent in light emission efficiency.

$Ar^3$ is preferably an aromatic hydrocarbon group optionally having a substituent, because the light emitting device of the present invention is excellent in light emission efficiency.

The definition and examples of the arylene group portion obtained by removing m substituents of the aromatic hydrocarbon group represented by $Ar^3$ are the same as the definition and examples of the arylene group represented by $Ar^{X2}$ in the formula (X) described above.

The definition and examples of the divalent heterocyclic group portion obtained by removing m substituents of the heterocyclic group represented by $Ar^3$ are the same as the definition and examples of the divalent heterocyclic group portion represented by $Ar^{X2}$ in the formula (X) described above.

The definition and examples of the divalent group obtained by removing m substituents of the group in which at least one aromatic hydrocarbon ring and at least one heterocyclic ring are bonded directly to each other represented by $Ar^3$ are the same as the definition and examples of the divalent group in which at least one arylene group and at least one divalent heterocyclic group are bonded directly to each other represented by $Ar^{X2}$ in the formula (X) described above.

$Ar^2$ and $Ar^4$ are preferably an arylene group optionally having a substituent, because the light emitting device of the present invention is more excellent in luminance life.

The definition and examples of the arylene group represented by $Ar^2$ and $Ar^4$ are the same as the definition and examples of the arylene group represented by $Ar^{X1}$ and $Ar^{X3}$ in the formula (X) described above.

The definition and examples of the divalent heterocyclic group represented by $Ar^2$ and $Ar^4$ are the same as the definition and examples of the divalent heterocyclic group represented by $Ar^{X1}$ and $Ar^{X3}$ in the formula (X) described above.

The group represented by $Ar^2$, $Ar^3$ and $Ar^4$ optionally has a substituent, and the substituent includes an alkyl group, a cycloalkyl group, an alkoxy group, a cycloalkoxy group, an aryl group, an aryloxy group, a halogen atom, a monovalent heterocyclic group and a cyano group.

The definitions and examples of the alkylene group, the cycloalkylene group, the arylene group and the divalent heterocyclic group represented by $K^A$ are the same as the definitions and examples of the alkylene group, the cycloalkylene group, the arylene group and the divalent heterocyclic group represented by $L^A$, respectively.

$K^A$ is preferably a phenylene group or a methylene group, because production of the polymer compound of the second organic layer is easy, and these groups each optionally have a substituent.

The preferable range, the more preferable range and the further preferable range of the crosslinkable group represented by X' are the same as the preferable range, the more preferable range and the further preferable range of the crosslinkable group selected from the above-described Group A of crosslinkable group.

The amount of the constitutional unit represented by the formula (4) is preferably 0.5 to 25 mol %, more preferably 3 to 25 mol %, further preferably 3 to 20 mol %, with respect to the total amount of constitutional units contained in the polymer compound of the second organic layer, because the polymer compound of the second organic layer is excellent in crosslinkability.

The constitutional unit represented by the formula (4) may be contained singly or two or more of the constitutional units may be contained in the polymer compound of the second organic layer.

The constitutional unit represented by the formula (3) includes, for example, constitutional units represented by the formula (3-1) to the formula (3-30), and the constitutional unit represented by the formula (4) includes, for example, constitutional units represented by the formula (4-1) to the formula (4-13). Of them, preferable are constitutional units represented by the formula (3-1) to the formula (3-30), more preferable are constitutional units represented by the formula (3-1) to the formula (3-15), the formula (3-19), the formula (3-20), the formula (3-23), the formula (3-25) or the formula (3-30), further preferable are constitutional units represented by the formula (3-1) to the formula (3-13) or the formula (3-30), particularly preferable are constitutional units represented by the formula (3-1) to the formula (3-9) or the formula (3-30), because the polymer compound of the second organic layer is excellent in crosslinkability.

[Chemical Formula 89]

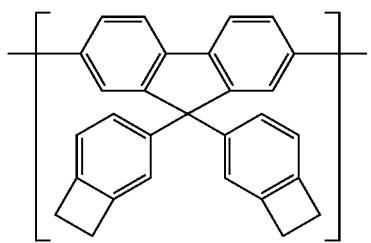
(3-1)

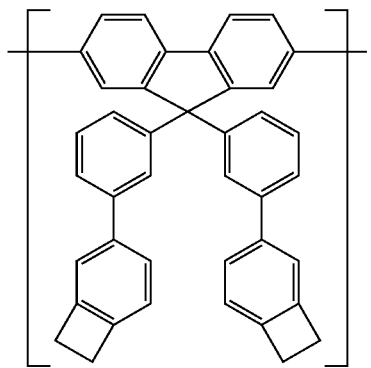
(3-2)

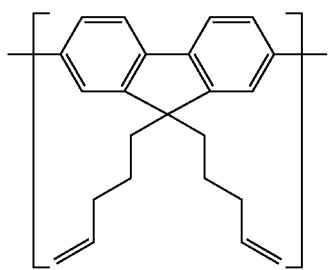
(3-3)

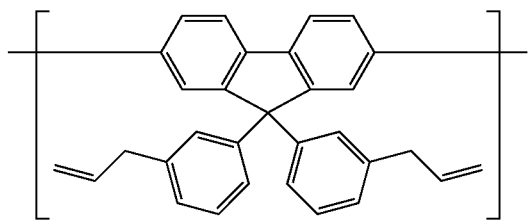
(3-4)

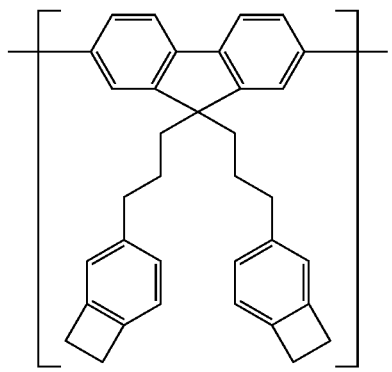
(3-5)

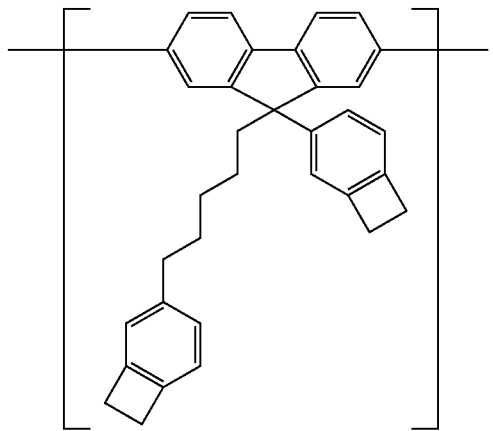
(3-6)

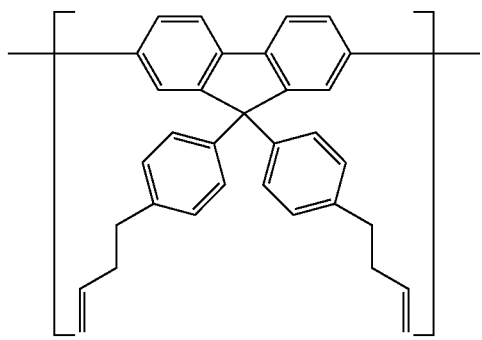
(3-7)

(3-8)
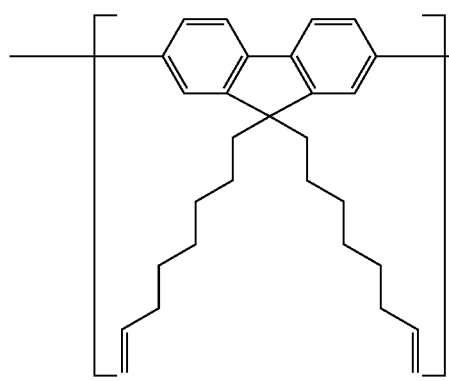
(3-9)
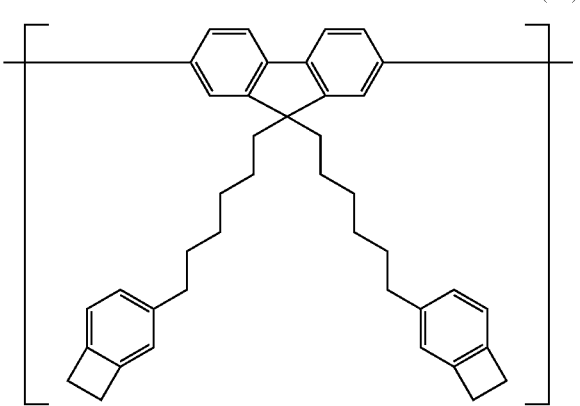
(3-10)
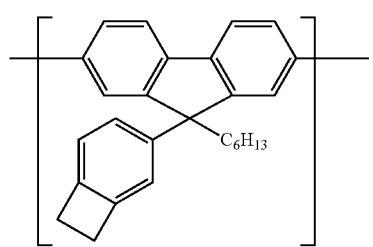
(3-11)
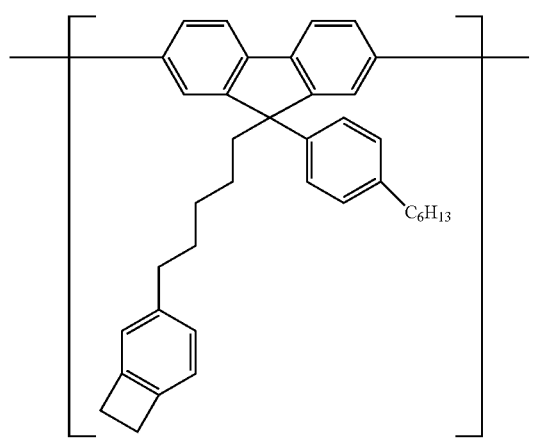
(3-12)
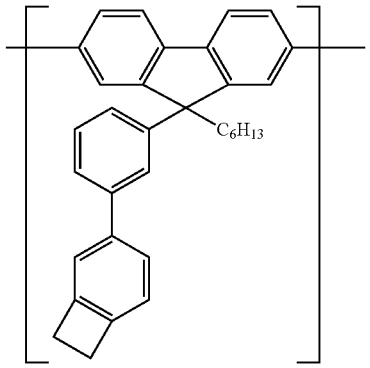
(3-13)
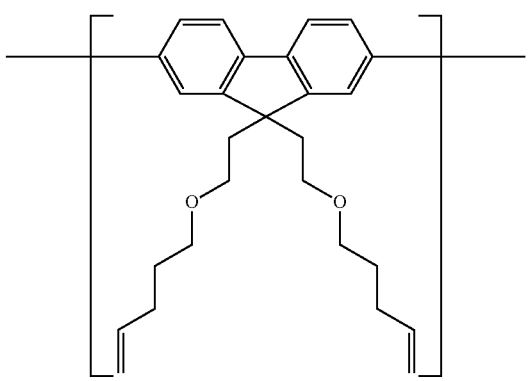
(3-14)
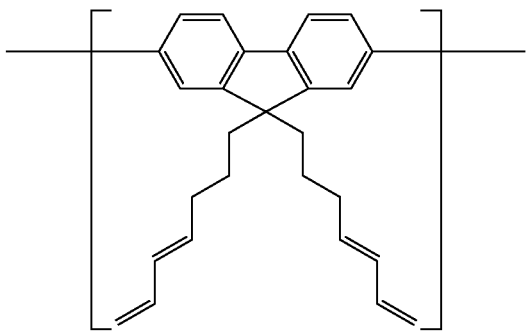
(3-15)
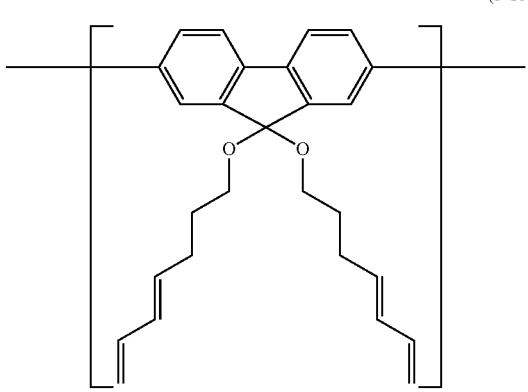

(3-16)
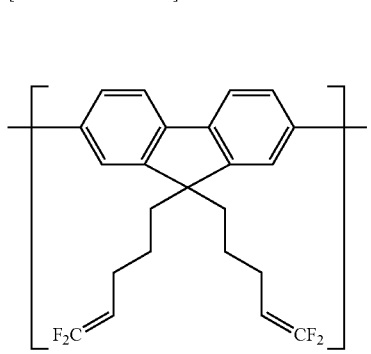
(3-20)
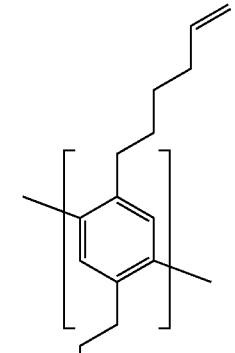
(3-17)
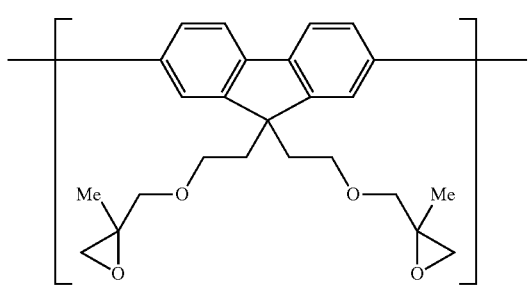
(3-21)
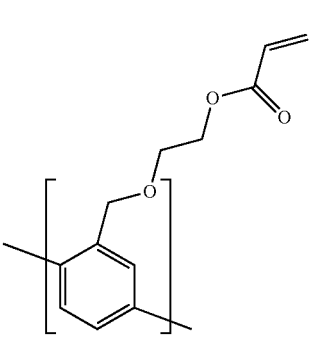
(3-18)
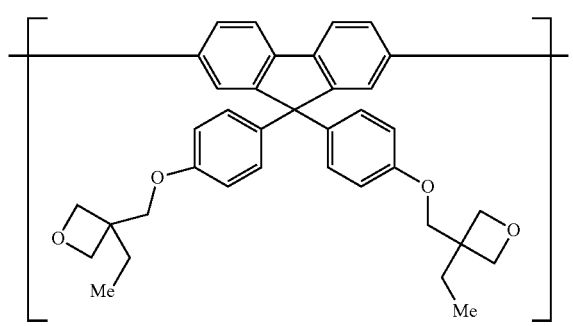
(3-22)
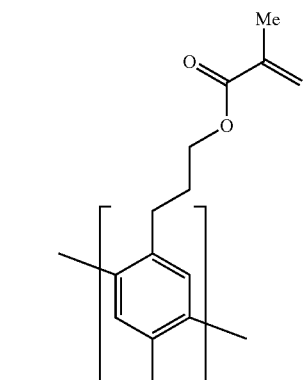
(3-19)
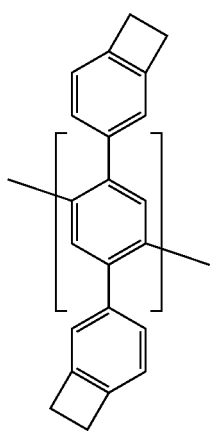

(3-23)
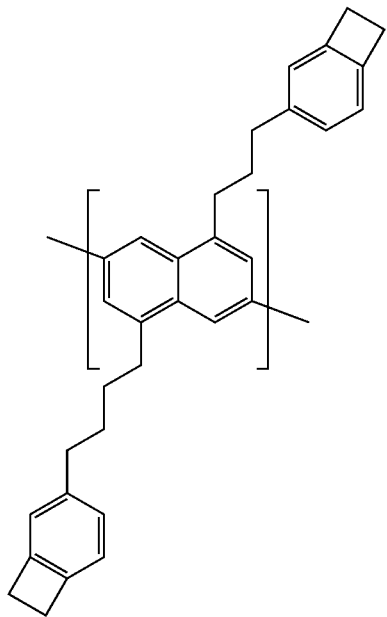
(3-24)
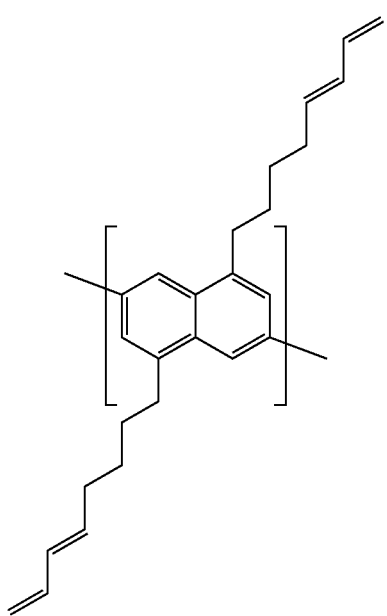
(3-25)
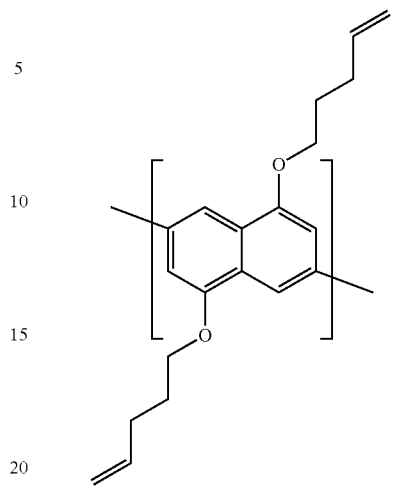
(3-26)
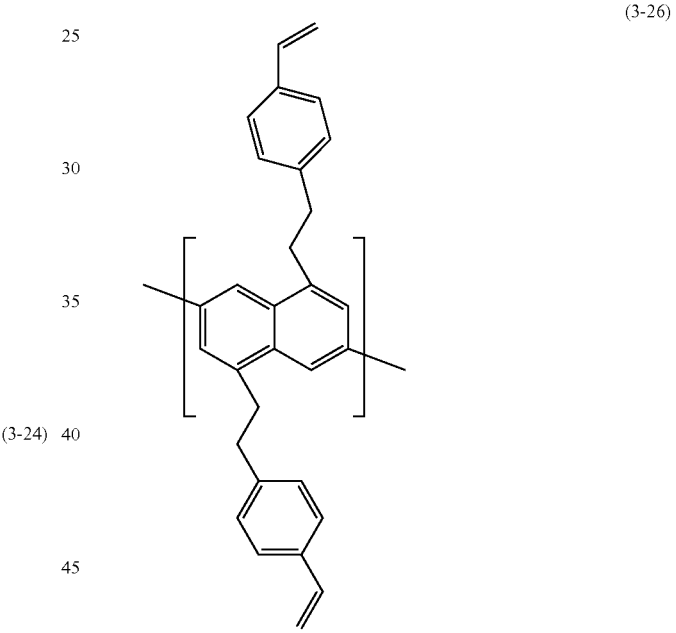
(3-27)
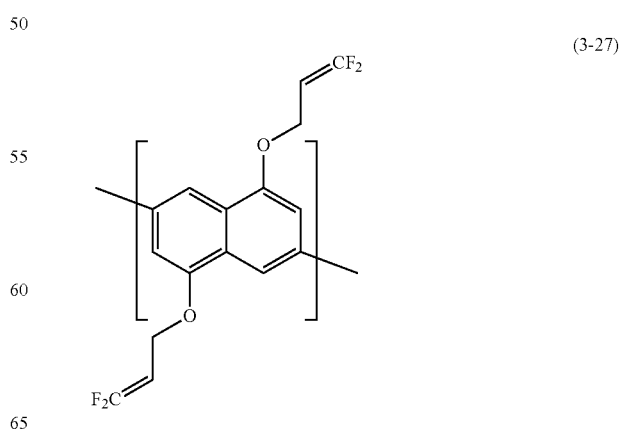

(3-28)
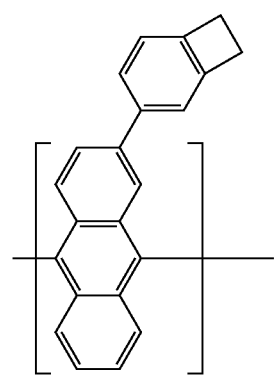
(3-29)
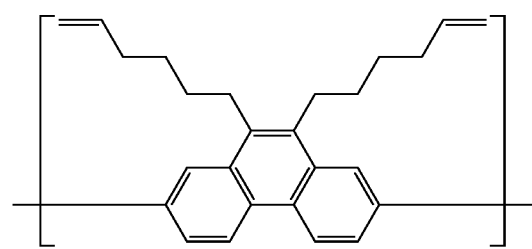
(3-30)
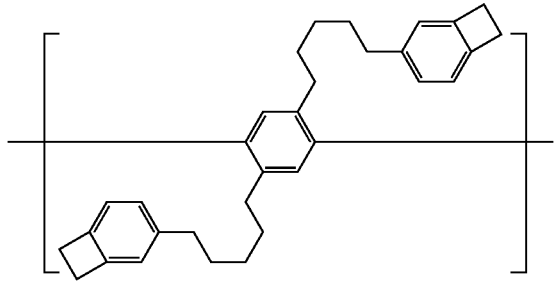
[Chemical formula 91]
(4-1)
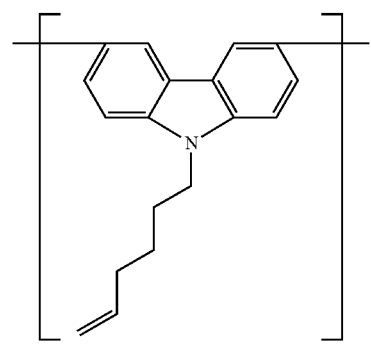
(4-2)
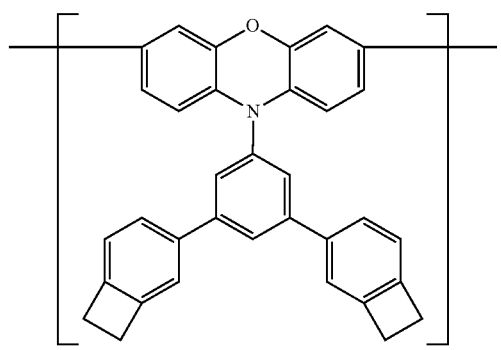
(4-3)
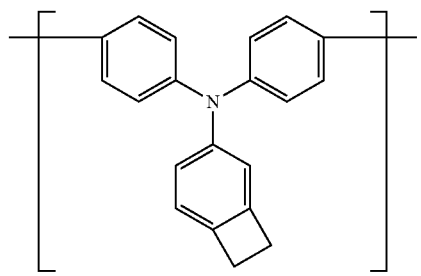
(4-4)
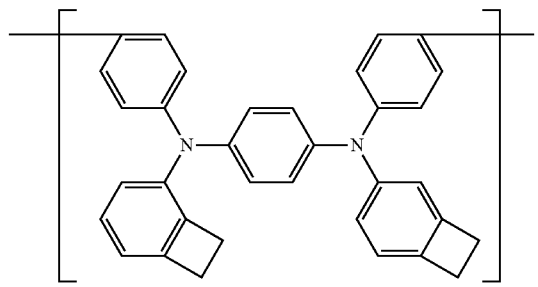
(4-5)
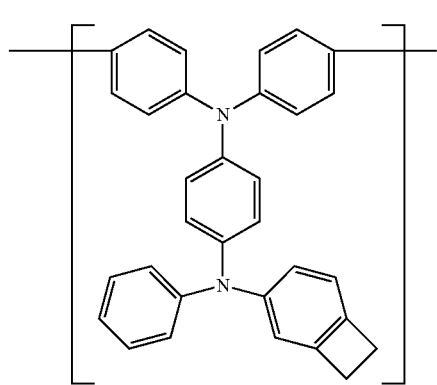
(4-6)
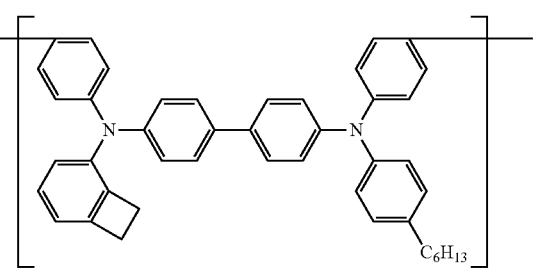

-continued (4-7)

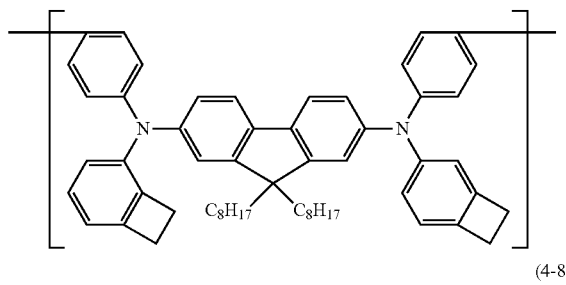

(4-8)

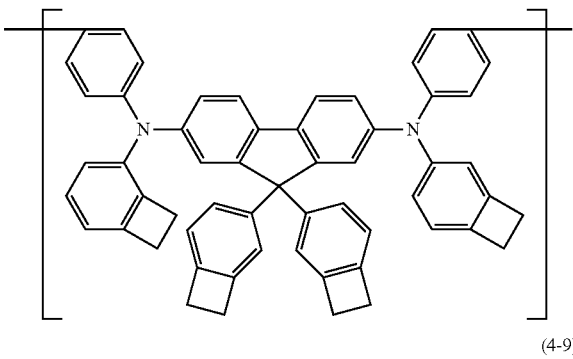

[Chemical formula 92]

(4-9)

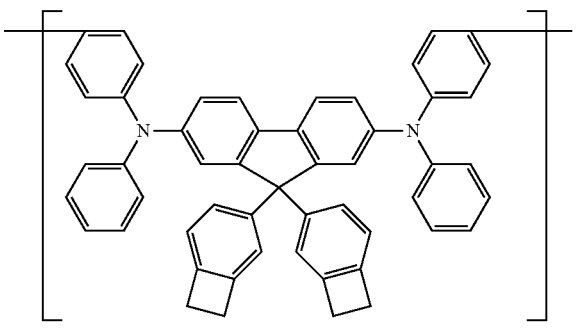

(4-10)

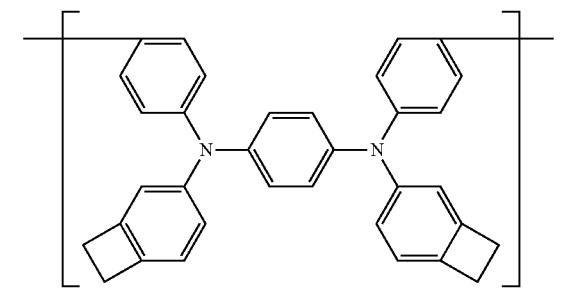

(4-11)

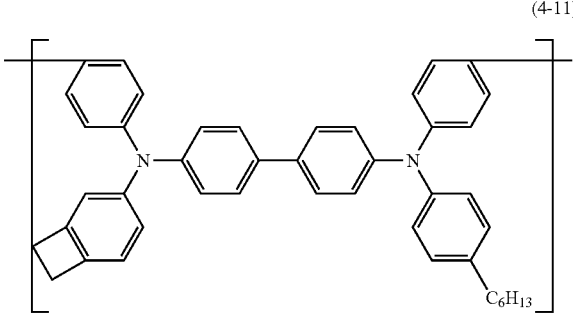

-continued (4-12)

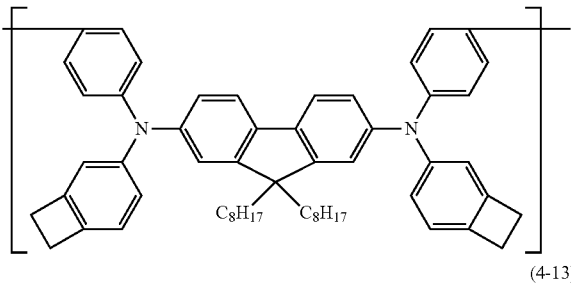

(4-13)

It is preferable that the polymer compound of the second organic layer further comprises a constitutional unit represented by the formula (X), because hole transportability is excellent.

The definition and examples of the constitutional unit represented by the formula (X) which the polymer compound of the second organic layer may comprise are the same as the definition and examples of the constitutional unit represented by the formula (X) which the above-described polymer host may comprise.

The constitutional unit represented by the formula (X) may be contained singly or two or more of the constitutional units may be contained in the polymer compound of the second organic layer.

It is preferable that the polymer compound of the second organic layer further comprises a constitutional unit represented by the formula (Y), because the light emitting device of the present invention is excellent in light emission efficiency.

The definition and examples of the constitutional unit represented by the formula (Y) which the polymer compound of the second organic layer may comprise are the same as the definition and examples of the constitutional unit represented by the formula (Y) which the above-described polymer host may comprise.

The constitutional unit represented by the formula (Y) may be contained singly or two or more of the constitutional units may be contained in the polymer compound of the second organic layer.

It is preferable that the polymer compound of the second organic layer further comprises both of a constitutional unit represented by the formula (X) and a constitutional unit represented by the formula (Y), because the light emitting device of the present invention is excellent in light emission efficiency.

Examples of the polymer compound of the second organic layer include polymer compounds (P-11) to (P-25) in the Table 2.

TABLE 2

| | constitutional unit and mole fraction thereof | | | | | | |
|---|---|---|---|---|---|---|---|
| | | | formula (X) | formula (Y) | | | |
| polymer compound | formula (3) p' | formula (4) q' | formulae (X-1) to (X-7) r' | formulae (Y-1) to (Y-3) s' | formulae (Y-4) to (Y-7) t' | formulae (Y-8) to (Y-10) u' | other v' |
| P-11 | 0.1 to 99.9 | 0 | 0.1 to 99.9 | 0 | 0 | 0 | 0 to 30 |
| P-12 | 0 | 0.1 to 99.9 | 0.1 to 99.9 | 0 | 0 | 0 | 0 to 30 |
| P-13 | 0.1 to 99.9 | 0 | 0 | 0 | 0 | 0.1 to 99.9 | 0 to 30 |
| P-14 | 0 | 0.1 to 99.9 | 0 | 0 | 0 | 0.1 to 99.9 | 0 to 30 |
| P-15 | 0.1 to 99.8 | 0 | 0.1 to 99.8 | 0 | 0 | 0.1 to 99.8 | 0 to 30 |
| P-16 | 0 | 0.1 to 99.8 | 0.1 to 99.8 | 0 | 0 | 0.1 to 99.8 | 0 to 30 |
| P-17 | 0.1 to 99.8 | 0.1 to 99.8 | 0.1 to 99.8 | 0 | 0 | 0 | 0 to 30 |
| P-18 | 0.1 to 99.8 | 0 | 0.1 to 99.8 | 0.1 to 99.8 | 0 | 0 | 0 to 30 |
| P-19 | 0 | 0.1 to 99.8 | 0.1 to 99.8 | 0.1 to 99.8 | 0 | 0 | 0 to 30 |
| P-20 | 0.1 to 99.7 | 0.1 to 99.7 | 0.1 to 99.7 | 0.1 to 99.7 | 0 | 0 | 0 to 30 |
| P-21 | 0.1 to 99.7 | 0.1 to 99.7 | 0 | 0.1 to 99.7 | 0 | 0.1 to 99.7 | 0 to 30 |
| P-22 | 0.1 to 99.7 | 0.1 to 99.7 | 0.1 to 99.7 | 0 | 0.1 to 99.7 | 0 | 0 to 30 |
| P-23 | 0.1 to 99.7 | 0.1 to 99.7 | 0.1 to 99.7 | 0 | 0 | 0.1 to 99.7 | 0 to 30 |
| P-24 | 0.1 to 99.6 | 0.1 to 99.6 | 0.1 to 99.6 | 0.1 to 99.6 | 0 | 0.1 to 99.6 | 0 to 30 |
| P-25 | 0.1 to 99.5 | 0.1 to 99.5 | 0.1 to 99.5 | 0.1 to 99.5 | 0.1 to 99.5 | 0.1 to 99.5 | 0 to 30 |

[In the table, p', q', r', s', u' and v' represent the mole fraction of each constitutional unit. p'+q'+r'+s'+u'+v'=100, and 70≤p'+q'+r'+s'+u'≤100. Other constitutional unit denotes a constitutional unit other than the constitutional unit represented by the formula (3), the constitutional unit represented by the formula (4), the constitutional unit represented by the formula (Y) and the constitutional unit represented by the formula (X).]

The polymer compound of the second organic layer may be any of a block copolymer, a random copolymer, an alternating copolymer or a graft copolymer, and may also be another embodiment, and is preferably a copolymer produced by copolymerizing a plurality of raw material monomers.

<Production Method of Polymer Compound of Second Organic Layer>

The polymer compound of the second organic layer can be produced by using the same method as the above-described production method of polymer host.

[Composition Ratio and the Like]

In the composition used for formation of the second organic layer, the content of the phosphorescent compound is usually 0.1 to 50, preferably 0.2 to 45, more preferably 0.3 to 40, when the total amount of the phosphorescent compound and the crosslinkable material is 100 parts by weight.

[Composition of Second Organic Layer]

The second organic layer may be a layer formed by using a composition comprising one or more phosphorescent compounds, a crosslinkable material, and at least one material selected from the group consisting of a hole transporting material, a hole injection material, an electron transporting material, an electron injection material, a light emitting material (different from a phosphorescent compound), an antioxidant and a solvent (hereinafter, referred to also as "composition of second organic layer"). That is, the second organic layer may be a layer comprising one or more phosphorescent compounds, a crosslinkable material, and at least one material selected from the group consisting of a hole transporting material, a hole injection material, an electron transporting material, an electron injection material, a light emitting material (different from a phosphorescent compound) and an antioxidant, and is preferably a layer comprising one or more phosphorescent compounds, a crosslinked body of a crosslinkable material, and at least one material selected from the group consisting of a hole transporting material, a hole injection material, an electron transporting material, an electron injection material, a light emitting material (different from a phosphorescent compound) and an antioxidant.

The examples and the preferable ranges of a hole transporting material, an electron transporting material, a hole injection material, an electron injection material and a light emitting material contained in the composition of second organic layer are the same as the examples and the preferable ranges of a hole transporting material, an electron transporting material, a hole injection material, an electron injection material and a light emitting material contained in the composition of first organic layer. In the composition of second organic layer, the compounding amounts of a hole transporting material, an electron transporting material, a hole injection material, an electron injection material and a light emitting material are each usually 1 to 400 parts by weight, preferably 5 to 150 parts by weight, when the total amount of the phosphorescent compound and the crosslinkable material is 100 parts by weight.

The examples and the preferable range of an antioxidant contained in the composition of second organic layer are the same as the examples and the preferable range of an antioxidant contained in the first organic layer. In the composition of second organic layer, the compounding amount of an antioxidant is usually 0.001 to 10 parts by weight, when the total amount of the phosphorescent compound and the crosslinkable material is 100 parts by weight.

[Ink of Second Organic Layer]

The composition of second organic layer comprising a solvent (hereinafter, referred to also as "ink of second organic layer") can be suitably used in application methods such as a spin coat method and an inkjet printing method like the ink of first organic layer.

The preferable range of the viscosity of the ink of second organic layer is the same as the preferable range of the viscosity of the ink of first organic layer.

The examples and the preferable range of a solvent contained in the ink of second organic layer are the same as the examples and the preferable range of a solvent contained in the ink of first organic layer.

In the ink of second organic layer, the compounding amount of a solvent is usually 1000 to 100000 parts by weight, preferably 2000 to 20000 parts by weight, when the total amount of the phosphorescent compound and the crosslinkable material is 100 parts by weight.

<Layer Constitution of Light Emitting Device>

The light emitting device of the present invention comprises an anode, a cathode, a first organic layer disposed between the anode and the cathode and a second organic layer disposed between the anode and the first organic layer. The light emitting device of the present invention may comprise layers other than the anode, the cathode, the first organic layer and the second organic layer.

In the light emitting device of the present invention, the first organic layer is usually a light emitting layer.

In the light emitting device of the present invention, it is preferable that the first organic layer and the second organic layer are adjacent, because the light emitting device of the present invention is more excellent in luminance life.

It is preferable for the light emitting device of the present invention to further comprise at least one layer selected from the group consisting of a hole transporting layer and a hole injection layer between the anode and the second organic layer, because the light emitting device of the present invention is more excellent in power efficiency. Further, it is preferable for the light emitting device of the present invention to further comprise at least one layer selected from the group consisting of an electron transporting layer and an electron injection layer between the cathode and the first organic layer, because the light emitting device of the present invention is excellent in power efficiency.

The specific layer constitution of the light emitting device of the present invention includes layer constitutions represented by (D1) to (D19) described below. The light emitting device of the present invention usually comprises a substrate, and the anode may be first laminated on the substrate or the cathode may be first laminated on the substrate.

(D1) anode/second organic layer/first organic layer/cathode
(D2) anode/second organic layer/first organic layer/electron transporting layer/cathode
(D3) anode/second organic layer/first organic layer/electron injection layer/cathode
(D4) anode/second organic layer/first organic layer/electron transporting layer/electron injection layer/cathode
(D5) anode/hole injection layer/second organic layer/first organic layer/cathode
(D6) anode/hole injection layer/second organic layer/first organic layer/electron transporting layer/cathode
(D7) anode/hole injection layer/second organic layer/first organic layer/electron injection layer/cathode
(D8) anode/hole injection layer/second organic layer/first organic layer/electron transporting layer/electron injection layer/cathode
(D9) anode/hole transporting layer/second organic layer/first organic layer/cathode
(D10) anode/hole transporting layer/second organic layer/first organic layer/electron transporting layer/cathode
(D11) anode/hole transporting layer/second organic layer/first organic layer/electron injection layer/cathode
(D12) anode/hole transporting layer/second organic layer/first organic layer/electron transporting layer/electron injection layer/cathode
(D13) anode/hole injection layer/hole transporting layer/second organic layer/first organic layer/cathode
(D14) anode/hole injection layer/hole transporting layer/second organic layer/first organic layer/electron transporting layer/cathode
(D15) anode/hole injection layer/hole transporting layer/second organic layer/first organic layer/electron injection layer/cathode
(D16) anode/hole injection layer/hole transporting layer/second organic layer/first organic layer/electron transporting layer/electron injection layer/cathode In (D1) to (D16) described above, "/" denotes adjacent lamination of anterior and posterior layers. Specifically, "second organic layer/first organic layer" means that the second organic layer and the first organic layer are laminated adjacently.

In the light emitting device of the present invention, if necessary, two or more of each of a hole injection layer, a hole transporting layer, an electron transporting layer and an electron injection layer may be provided.

The thickness of an anode, a cathode, a first organic layer, a second organic layer, a hole injection layer, a hole transporting layer, an electron injection layer and an electron transporting layer is usually 1 nm to 1 µm, preferably 2 nm to 500 nm, further preferably 5 nm to 150 nm.

In the light emitting device of the present invention, the order, the number and the thickness of layers to be laminated may be advantageously adjusted in views of the light emission efficiency and the device lifetime of the light emitting device.

[Hole Transporting Layer]

The hole transporting layer is usually a layer formed by using a hole transporting material, and is a layer comprising a hole transporting material. The hole transporting material used for formation of the hole transporting layer includes, for example, hole transporting materials which the above-described composition of the first organic layer may comprise. The hole transporting material may be used singly, or two or more hole transporting materials may be used in combination.

[Electron Transporting Layer]

The electron transporting layer is usually a layer formed by using an electron transporting material, and is a layer comprising an electron transporting material. The electron transporting material used for formation of the electron transporting layer includes, for example, electron transporting materials which the above-described composition of the first organic layer may comprise and a polymer compound comprising at least one constitutional unit selected from the group consisting of a constitutional unit represented by the formula (ET-1) and a constitutional unit represented by the formula (ET-2), preferably, a polymer compound comprising at least one constitutional unit selected from the group consisting of a constitutional unit represented by the formula (ET-1) and a constitutional unit represented by the formula (ET-2). The electron transporting material may be used singly, or two or more electron transporting materials may be used in combination.

[Chemical formula 93]

(ET-1)

[wherein, nE1 represents an integer of 1 or more.

$Ar^{E1}$ represents an aromatic hydrocarbon group or a heterocyclic group, and these groups each optionally have a substituent other than $R^{E1}$.

$R^{E1}$ represents a group represented by the formula (ES-1). When a plurality of $R^{E1}$ are present, they may be the same or different.]

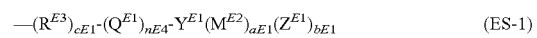

(ES-1)

[wherein, cE1 represents 0 or 1, nE4 represents an integer of 0 or more, aE1 represents an integer of 1 or more, and bE1 represents an integer of 0 or more.

$R^{E3}$ represents an arylene group or a divalent heterocyclic group, and these groups each optionally have a substituent.

$Q^{E1}$ represents an alkylene group, an arylene group, an oxygen atom or a sulfur atom, and these groups each optionally have a substituent. When a plurality of $Q^{E1}$ are present, they may be the same or different.

$Y^{E1}$ represents $-CO_2^-$, $-SO_3^-$, $-SO_2^-$ or $PO_3^{2-}$.

$M^{E2}$ represents a metal cation or an ammonium cation, and this ammonium cation optionally has a substituent. When a plurality of $M^{E2}$ are present, they may be the same or different.

$Z^{E1}$ represents $F^-$, $Cl^-$, $Br^-$, $I^-$, $OH^-$, $R^{E4}SO_3^-$, $R^{E4}COO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$. $R^{E4}$ represents an alkyl group, a cycloalkyl group or an aryl group, and these groups each optionally have a substituent. When a plurality of $Z^{E1}$ are present, they may be the same or different.

aE1 and bE1 are selected so that the charge of the group represented by the formula (ES-1) is 0.]

nE1 is preferably an integer of 1 to 4, more preferably 1 or 2.

The aromatic hydrocarbon group or the heterocyclic group represented by $Ar^{E1}$ is preferably an atomic group remaining after removing from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, a 2,7-phenanthrenediyl group or a 2,7-carbazoledilyl group nE1 hydrogen atoms bonding directly to atoms constituting the ring, and optionally has a substituent other than $R^{E1}$.

The substituent other than $R^{E1}$ which $Ar^{E1}$ optionally has includes a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group, a cycloalkynyl group, a carboxyl group, and a group represented by the formula (ES-3).

$$-O(C_{n'}H_{2n'}O)_{nx}C_mH_{2m'+1} \quad (ES-3)$$

[wherein, n', m' and nx represent an integer of 1 or more.]

cE1 is preferably 0 or 1, and nE4 is preferably an integer of 0 to 6.

$R^{E3}$ is preferably an arylene group.

$Q^{E1}$ is preferably an alkylene group, an arylene group or an oxygen atom.

$Y^{E1}$ is preferably $-CO_2^-$ or $SO_3^-$.

$M^{E2}$ is preferably $Li^+$, $Na^+$, $K^+$, $Cs^+$, $N(CH_3)_4^+$, $NH(CH_3)_3^+$, $NH_2(CH_3)_2^+$ or $N(C_2H_5)_4^+$.

$Z^{E1}$ is preferably $F^-$, $Cl^-$, $Br^-$, $I^-$, $OH^-$, $R^{E4}SO_3^-$ or $R^{E4}COO^-$.

The substituent which $R^{E3}$ optionally has includes an alkyl group, a cycloalkyl group, an aryl group, a monovalent heterocyclic group and a group represented by the formula (ES-3). It is preferable that $R^{E3}$ has a group represented by the formula (ES-3) as a substituent, because the light emitting device of the present invention is excellent in light emission efficiency.

The group represented by the formula (ES-1) includes, for example, groups represented by the following formulae.

[Chemical formula 94]

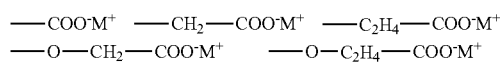

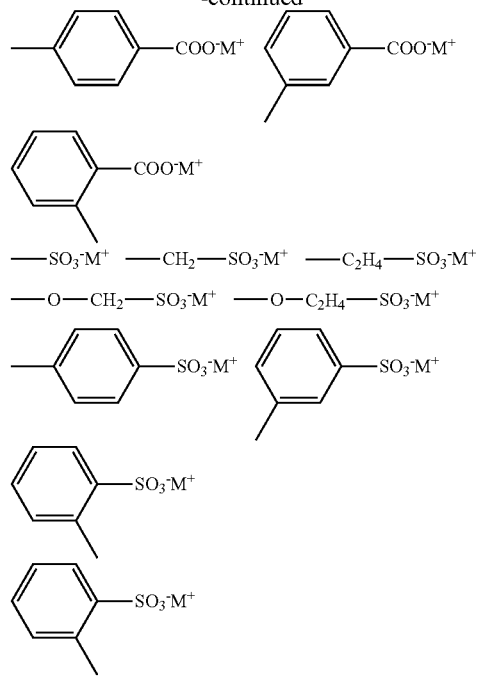

[wherein, $M^+$ represents $Li^+$, $Na^+$, $K^+$, $Cs^+$, $N(CH_3)_4^+$, $NH(CH_3)_3^+$, $NH_2(CH_3)_2^+$ or $N(C_2H_5)_4^+$.]

[Chemical formula 95]

$$-\!\!\!\!+\!Ar^{E2}\!+\!\!\!\!- \overset{(R^{E2})_{nE2}}{|} \quad (ET\text{-}2)$$

[wherein, nE2 represents an integer of 1 or more.

$Ar^{E2}$ represents an aromatic hydrocarbon group or a heterocyclic group, and these groups each optionally have a substituent other than $R^{E2}$.

$R^{E2}$ represents a group represented by the formula (ES-2). When a plurality of $R^{E2}$ are present, they may be the same or different.]

$$-(R^{E6})_{cE2}(Q^{E2})_{nE6}\text{-}Y^{E2}(M^{E3})_{bE2}(Z^{E2})_{aE1} \quad (ES\text{-}2)$$

[wherein, cE2 represents 0 or 1, nE6 represents an integer of 0 or more, bE2 represents an integer of 1 or more, and aE2 represents an integer of 0 or more.

$R^{E6}$ represents an arylene group or a divalent heterocyclic group, and these groups each optionally have a substituent.

$Q^{E2}$ represents an alkylene group, an arylene group, an oxygen atom or a sulfur atom, and these groups each optionally have a substituent. When a plurality of $Q^{E2}$ are present, they may be the same or different.

$Y^{E2}$ represents a carbocation, an ammonium cation, a phosphonyl cation or a sulfonyl cation.

$M^{E3}$ represents $F^-$, $Cl^-$, $Br^-$, $I^-$, $OH^-$, $R^{E7}SO_3^-$, $R^{E7}COO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, tetraphenyl borate, $BF_4^-$ or $PF_6^-$. $R^{E7}$ represents an alkyl group, a perfluoroalkyl group or an aryl group, and these groups each optionally have a substituent. When a plurality of $M^{E3}$ are present, they may be the same or different.

$Z^{E2}$ represents a metal ion or an ammonium ion, and this ammonium ion optionally has a substituent. When a plurality of $Z^{E2}$ are present, they may be the same or different.

aE2 and bE2 are selected so that the charge of the group represented by the formula (ES-2) is 0.]

nE2 is preferably an integer of 1 to 4, more preferably 1 or 2.

The aromatic hydrocarbon group or the heterocyclic group represented by $Ar^{E2}$ is preferably an atomic group remaining after removing from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, a 2,7-phenanthrenediyl group or a 2,7-carbazolediyl group nE2 hydrogen atoms bonding directly to atoms constituting the ring, and optionally has a substituent other than $R^{E2}$.

The substituent other than $R^{E2}$ which $Ar^{E2}$ optionally has is the same as the substituent other than $R^{E1}$ which $Ar^{E1}$ optionally has.

cE2 is preferably 0 or 1, and nE6 is preferably an integer of 0 to 6.

$R^{E6}$ is preferably an arylene group.

$Q^{E2}$ is preferably an alkylene group, an arylene group or an oxygen atom.

$Y^{E2}$ is preferably a carbocation or an ammonium cation.

$M^{E3}$ is preferably $F^-$, $Cl^-$, $Br^-$, $I^-$, tetraphenyl borate, $CF_3SO_3^-$ or $CH_3COO^-$.

$Z^{E2}$ is preferably $Li^+$, $Na^+$, $K^+$, $Cs^+$, $N(CH_3)_4^+$, $NH(CH_3)_3^+$, $NH_2(CH_3)_2^+$ or $N(C_2H_5)_4^+$.

The substituent which $R^{E6}$ optionally has includes an alkyl group, a cycloalkyl group, an aryl group, a monovalent heterocyclic group and a group represented by the formula (ES-3). It is preferable that $R^{E6}$ has a group represented by the formula (ES-3) as a substituent, because the light emitting device of the present invention is excellent in light emission efficiency.

The group represented by the formula (ES-2) includes, for example, groups represented by the following formulae.

[Chemical formula 96]

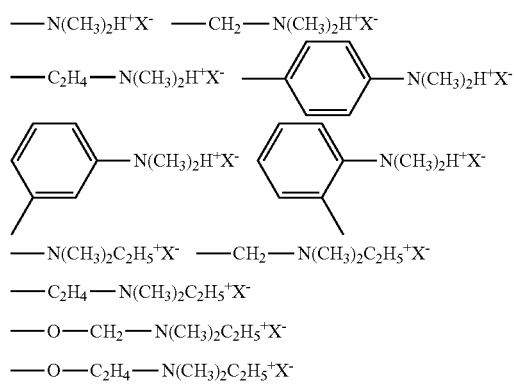

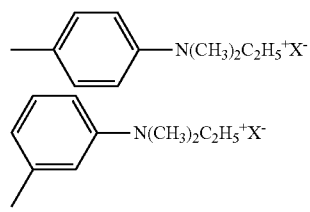

-continued

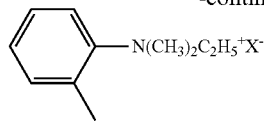

[wherein, $X^-$ represents $F^-$, $Cl^-$, $Br^-$, $I^-$, tetraphenyl borate, $CF_3SO_3^-$ or $CH_3COO^-$.]

The constitutional unit represented by the formula (ET-1) and the formula (ET-2) includes, for example, constitutional units represented by the formula (ET-31) to the formula (ET-34) described below.

[Chemical formula 97]

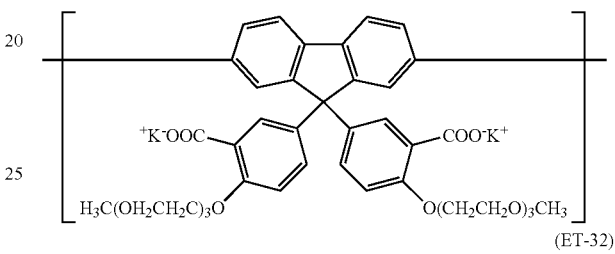

(ET-31)

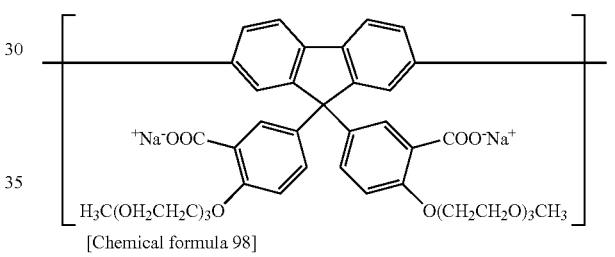

(ET-32)

[Chemical formula 98]

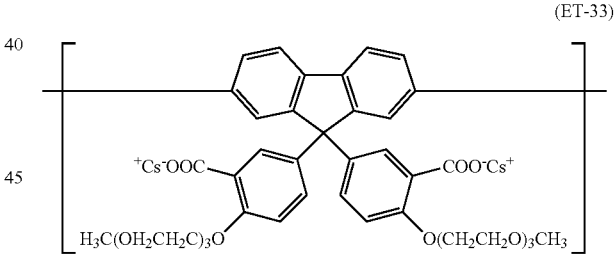

(ET-33)

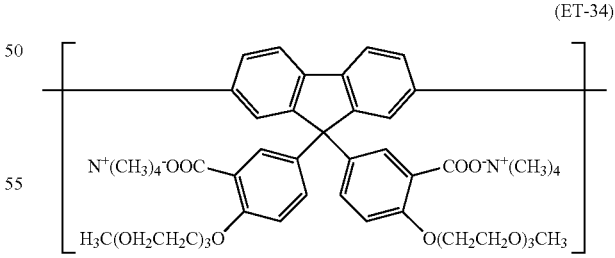

(ET-34)

When a material used for formation of the hole injection layer described later, a material used for formation of the hole transporting layer, a material used for formation of the second organic layer, a material used for formation of the first organic layer, a material used for formation of the electron transporting layer, and a material used for formation of the electron injection layer described later are each soluble in a solvent used in forming a layer adjacent to the hole injection layer, the hole transporting layer, the second organic layer, the first organic layer, the electron transporting layer and the electron injection layer in fabrication of a light emitting device, it is preferable that dissolution of the material in the solvent is avoided. As the method for avoiding dissolution of the material, i) a method of using a material having a crosslinkable group or ii) a method of providing a difference of solubility between adjacent layers is preferable. In the above-described method i), a layer is formed using a material having a crosslinkable group, then, the crosslinkable group is crosslinked, thus, the layer can be insolubilized.

When an electron transporting layer is laminated on the first organic layer by utilizing a difference of solubility, the electron transporting layer can be laminated by using a solution manifesting low solubility for the first organic layer.

As the solvent used in laminating an electron transporting layer on the first organic layer by utilizing a difference of solubility, preferable are water, alcohols, ethers, esters, nitrile compounds, nitro compounds, fluorinated alcohols, thiols, sulfides, sulfoxides, thioketones, amides, carboxylic acids and the like. Specific examples of the solvent include methanol, ethanol, 2-propanol, 1-butanol, tert-butyl alcohol, acetonitrile, 1,2-ethanediol, N,N-dimethylformamide, dimethyl sulfoxide, acetic acid, nitromethane, propylene carbonate, pyridine, carbon disulfide and a mixed solvent of these solvents. When the mixed solvent is used, mixed solvents composed of one or more solvents selected from water, alcohols, ethers, esters, nitrile compounds, nitro compounds, fluorinated alcohols, thiols, sulfides, sulfoxides, thioketones, amides, carboxylic acids and the like and one or more solvents selected from chlorine-based solvents, aromatic hydrocarbon solvents, aliphatic hydrocarbon solvents and ketone solvents may be permissible.

[Hole Injection Layer and Electron Injection Layer]

The hole injection layer is usually a layer formed by using a hole injection material and comprises a hole injection material. The hole injection material used for formation of the hole injection layer includes, for example, hole injection materials which the above-described composition of the first organic layer may comprise. The hole injection material may be used singly, or two or more hole injection materials may be used in combination.

The electron injection layer is usually a layer formed by using an electron injection material and comprises an electron injection material. The electron injection material used for formation of the electron injection layer includes, for example, electron injection materials which the above-described composition of the first organic layer may comprise. The electron injection material may be used singly, or two or more electron injection materials may be used in combination.

[Substrate/Electrode]

The substrate in the light emitting device may advantageously be a substrate on which an electrode can be formed and which does not chemically change in forming an organic layer, and is a substrate made of a material such as, for example, glass, plastic and silicon. In the case of using an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium.tin.oxide (ITO) and indium.zinc.oxide; a composite of silver, palladium and copper (APC); NESA, gold, platinum, silver and copper.

The material of the cathode includes, for example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode each may be a laminated structure composed of two or more layers.

In the light emitting device of the present invention, at least one of the anode and the cathode is usually transparent or semi-transparent, and it is preferable that the anode is transparent or semi-transparent.

Methods for forming the anode and the cathode include, for example, vacuum vapor deposition method, sputtering method, ion plating method, plating method, lamination method and the like.

[Production Method of Light Emitting Device]

The method of forming each layer such as the first organic layer, the second organic layer, a hole transporting layer, an electron transporting layer, a hole injection layer and an electron injection layer in the light emitting device of the present invention includes, for example, a vacuum vapor deposition method from a powder and a method of film formation from a solution or melted state when a low molecular weight compound is used, and includes, for example, a method of film formation from a solution or melted state when a polymer compound is used.

The first organic layer, the second organic layer, the hole transporting layer, the electron transporting layer, the hole injection layer and the electron injection layer can be formed by application methods typified by a spin coat method and an inkjet printing method using the ink of the first organic layer, the ink of the second organic layer, inks containing the hole transporting material, the electron transporting material, the hole injection material and the electron injection material described above, respectively.

[Use of Light Emitting Device]

For obtaining planar light emission by using a light emitting device, a planar anode and a planar cathode are disposed so as to overlap with each other. Patterned light emission can be produced by a method of placing a mask with a patterned window on the surface of a planer light emitting device, a method of forming an extremely thick layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

In the present examples, the polystyrene-equivalent number average molecular weight (Mn) and the polystyrene-equivalent weight average molecular weight (Mw) of a polymer compound were measured by size exclusion chromatography (SEC) (manufactured by Shimadzu Corp., trade name: LC-10Avp). SEC measurement conditions are as described below.

[Measurement Condition]

The polymer compound to be measured was dissolved in THF at a concentration of about 0.05 wt %, and 10 μL of the solution was injected into SEC. As the mobile phase of SEC, THF was used and allowed to flow at a flow rate of 2.0 mL/min. As the column, PLgel MIXED-B (manufactured by Polymer Laboratories) was used. As the detector, UV-VIS detector (manufactured by Shimadzu Corp., trade name: SPD-10Avp) was used.

Measurement of NMR was carried out according to the following method.

5 to 10 mg of a measurement sample was dissolved in about 0.5 mL of deuterated chloroform ($CDCl_3$), deuterated tetrahydrofuran (THF-$d_8$) or deuterated methylene chloride ($CD_2Cl_2$), and measurement was performed using an NMR apparatus (manufactured by Agilent, trade name: INOVA 300 or MERCURY 400VX).

<Synthesis Example 1> Synthesis of Compound G1

A compound G1 was synthesized according to a method described in International Publication WO2009/131255.

[Chemical formula 99]

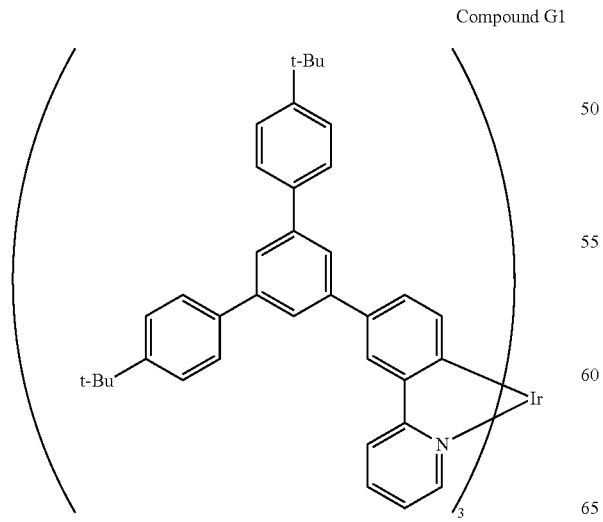

<Synthesis Example 2> Synthesis of Compound G2

A compound G2 was synthesized according to a method described in International Publication WO2008/090795.

[Chemical formula 100]

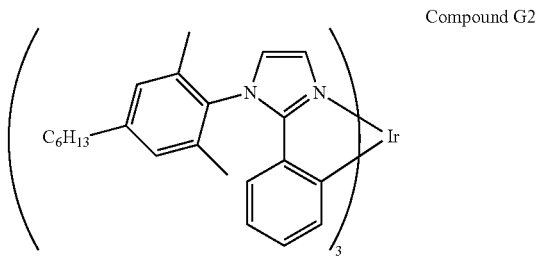

<Synthesis Example 3> Synthesis of Compound G3

A compound G3 was synthesized according to a method described in JP-A No. 2006-188673.

[Chemical formula 101]

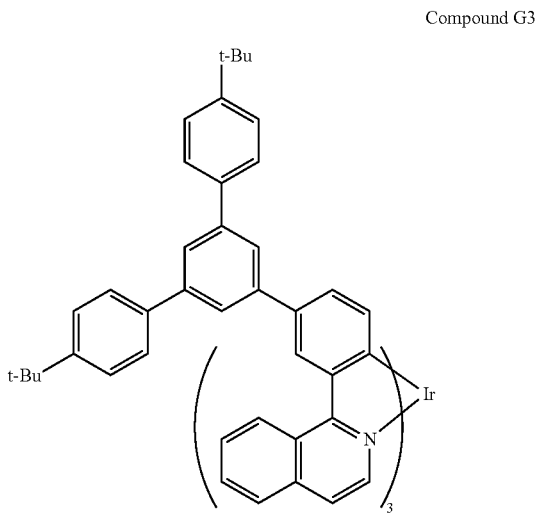

<Synthesis Example 4> Synthesis of Polymer Compound P1

[Chemical formula 102]

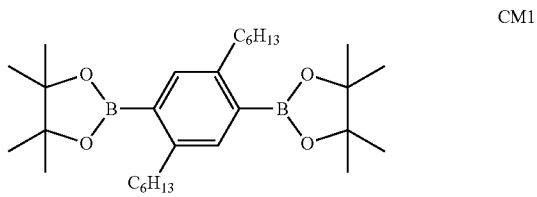

CM2
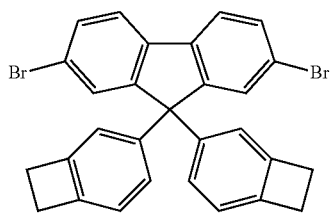

CM3
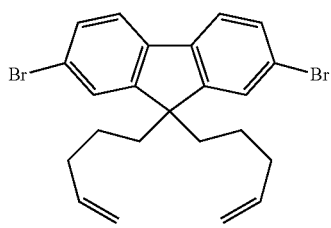

CM4
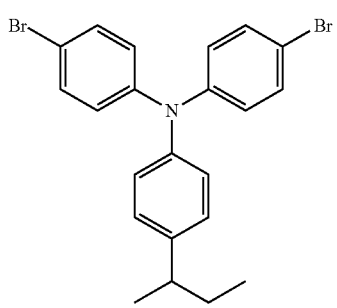

(Step 1) An inert gas atmosphere was prepared in a reaction vessel, then, a monomer CM1 (0.9950 g) synthesized according to a method described in JP-A No. 2010-189630, a monomer CM2 (0.1064 g) synthesized according to a method described in JP-A No. 2008-106241, a monomer CM3 (0.0924 g) synthesized according to a method described in JP-A No. 2010-215886, a monomer CM4 (0.7364 g) synthesized according to a method described in Japanese Patent Application National Publication No. 2002-539292, dichlorobis[tris(2-methoxyphenyl)phosphine]palladium (1.8 mg) and toluene (47 ml) were added, and heated at 105° C.

(Step 2) Into the reaction liquid, a 20 wt % tetraethylammonium hydroxide aqueous solution (6.6 ml) was dropped, and the mixture was refluxed for 5.5 hours.

(Step 3) Thereafter, to this were added phenylboronic acid (24.4 mg), a 20 wt % tetraethylammonium hydroxide aqueous solution (6.6 ml) and dichlorobis[tris(2-methoxyphenyl)phosphine]palladium (1.8 mg), and the mixture was refluxed for 14 hours.

(Step 4) Thereafter, to this was added a sodium diethyldithiacarbamate aqueous solution, and the mixture was stirred at 80° C. for 2 hours. After cooling, the reaction liquid washed with water twice, with a 3 wt % acetic acid aqueous solution twice and with water twice, and the resultant solution was dropped into methanol, to observe generation of a precipitate. The precipitate was dissolved in toluene, and purified by passing the solution through an alumina column and a silica gel column in this order. The resultant solution was dropped into methanol, and the mixture was stirred, then, the resultant precipitate was isolated by filtration, and dried, thereby obtaining 0.91 g of a polymer compound P1. The polymer compound P1 had a Mn of $5.2 \times 10^4$ and a Mw of $2.5 \times 10^5$.

The polymer compound P1 is a copolymer constituted of a constitutional unit derived from the monomer CM1, a constitutional unit derived from the monomer CM2, a constitutional unit derived from the monomer CM3 and a constitutional unit derived from the monomer CM4 at a molar ratio of 50:5:5:40 according to the theoretical values calculated from the amounts of the charged raw materials.

<Synthesis Example 5> Synthesis of Polymer Compound P2

[Chemical formula 103]

CM1
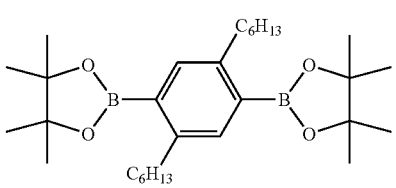

CM5
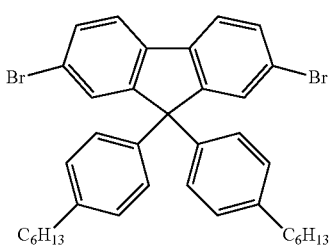

CM6
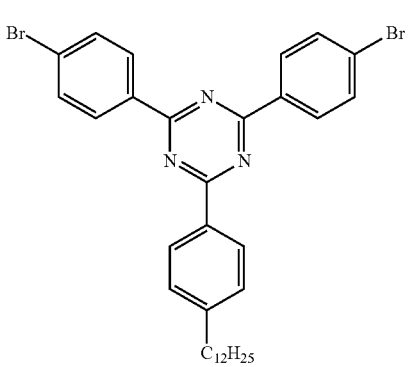

A polymer compound P2 was synthesized according to a method described in JP-A No. 2012-036388, using the monomer CM1, a monomer CM5 synthesized according to a method described in International Publication WO2012/86671 and a monomer CM6 synthesized according to a method described in JP-A No. 2010-189630. The polymer compound P2 had a Mn of $9.1 \times 10^4$ and a Mw of $2.3 \times 10^5$.

The polymer compound P2 is a copolymer constituted of a constitutional unit derived from the monomer CM1, a constitutional unit derived from the monomer CM5 and a constitutional unit derived from the monomer CM6 at a molar ratio of 50:40:10 according to the theoretical values calculated from the amounts of the charged raw materials.

<Synthesis Example 6> Synthesis of Polymer Compound P3

[Chemical formula 104]

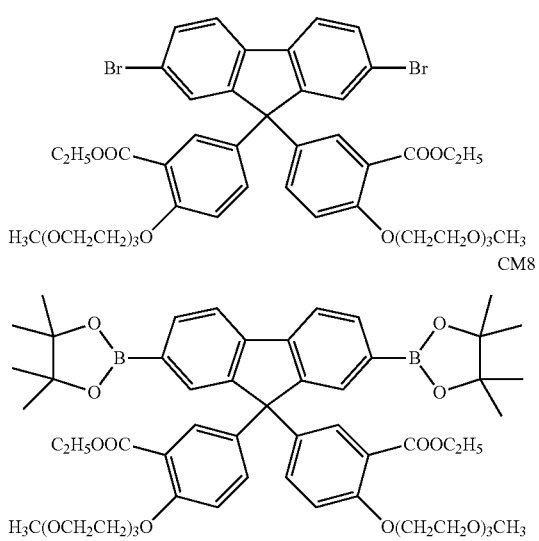

(Step 1) An inert gas atmosphere was prepared in a reaction vessel, then, a monomer CM7 (0.55 g) synthesized according to a method described in JP-A No. 2012-33845, a monomer CM8 (0.61 g) synthesized according to a method described in JP-A No. 2012-33845, triphenylphosphinepalladium (0.01 g), methyltrioctylammonium chloride (manufactured by Aldrich, trade name: Aliquat336 (registered trademark)) (0.20 g) and toluene (10 ml) were added, and heated at 105° C.

(Step 2) Into the reaction liquid, a 2M sodium carbonate aqueous solution (6 ml) was dropped, and the mixture was refluxed for 8 hours.

(Step 3) Thereafter, to this was added 4-tert-butylphenylboronic acid (0.01 g), and the mixture was refluxed for 6 hours.

(Step 4) Thereafter, to this was added a sodium diethyldithiocarbamate aqueous solution (10 mL, concentration: 0.05 g/mL), and the mixture was stirred for 2 hours. The resultant reaction solution was dropped into methanol (300 ml), and the mixture was stirred for 1 hour. Thereafter, the deposited precipitate was filtrated, dried under reduced pressure for 2 hours, and dissolved in tetrahydrofuran (20 ml). The resultant solution was dropped into a mixed solvent composed of methanol (120 ml) and a 3 wt % acetic acid aqueous solution (50 ml), and the mixture was stirred for 1 hour. Thereafter, the deposited precipitate was filtrated, and dissolved in tetrahydrofuran (20 ml).

(Step 5) The resultant solution was dropped into methanol (200 ml), and the mixture was stirred for 30 minutes. Thereafter, the deposited precipitate was filtrated. The resultant solid was dissolved in tetrahydrofuran, then, purified by passing the solution through an alumina column and a silica gel column in this order. The resultant solution was dropped into methanol, and the mixture was stirred, then, the deposited precipitate was filtrated. The resultant solid was dried, thereby obtaining 520 mg of a polymer compound P3. The polymer compound P3 had a Mn of $5.2 \times 10^4$ and a Mw of $1.5 \times 10^5$.

The polymer compound P3 is a copolymer constituted of a constitutional unit derived from the monomer CM7 and a constitutional unit derived from the monomer CM8 at a molar ratio of 50:50 according to the theoretical values calculated from the amounts of the charged raw materials.

<Synthesis Example 7> Synthesis of Polymer Compound P4

The polymer compound P3 (200 mg) was added into a reaction vessel, then, a nitrogen gas atmosphere was prepared in the reaction vessel. Thereafter, to this were added tetrahydrofuran (20 ml) and ethanol (20 ml), and the mixture was heated up to 55° C. Thereafter, to this was added a cesium hydroxide aqueous solution prepared by dissolving cesium hydroxide (200 mg) in water (2 ml), and the mixture was stirred at 55° C. for 6 hours. The resultant reaction mixture was cooled down to room temperature, then, the solvent was distilled off under reduced pressure. The resultant solid was washed with water, then, dried under reduced pressure, thereby obtaining a polymer compound P4 (150 mg). In $^1$H-NMR analysis of the polymer compound P4, a signal of an ethyl ester portion in the polymer compound P4 disappeared, and completion of the reaction was confirmed.

The polymer compound P4 is a copolymer composed a constitutional unit shown below according to the theoretical values calculated from the amounts of the charged raw materials of the polymer compound P3.

[Chemical formula 105]

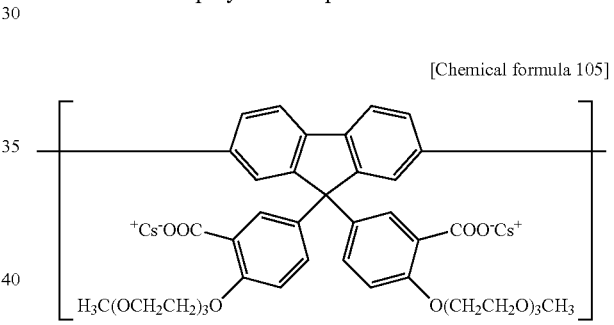

<Example 1> Fabrication and Evaluation of Light Emitting Device 1

(Formation of Anode and Hole Injection Layer)

A glass substrate was attached with an ITO film with a thickness of 45 nm by a sputtering method, to form an anode. On the anode, a polythiophene*sulfonic acid type hole injection agent AQ-1200 (manufactured by Plextronics) was spin-coated to form a film with a thickness of 35 nm, and the film was heated on a hot plate at 170° C. for 15 minutes under an air atmosphere, thereby forming a hole injection layer.

(Formation of Hole Transporting Layer)

The polymer compound P1 and the compound G1 (polymer compound P1/compound G1=80 wt %/20 wt %) were dissolved at a concentration of 0.6 wt % in xylene. The resultant xylene solution was spin-coated on the hole injection layer to form a film with a thickness of 20 nm, and the film was heated on a hot plate at 180° C. for 60 minutes under a nitrogen gas atmosphere, thereby forming a hole transporting layer. By heating on a hot plate at 180° C. for 60 minutes, the polymer compound P1 becomes a cross-linked body of the polymer compound P1.

(Formation of Light Emitting Layer)

The polymer compound P2 and the compound G1 (polymer compound P2/compound G1=70 wt %/30 wt %) were dissolved at a concentration of 2.5 wt % in xylene. The resultant xylene solution was spin-coated on the hole transporting layer to form a film with a thickness of 80 nm, and the film was heated at 130° C. for 10 minutes under a nitrogen gas atmosphere, thereby forming a light emitting layer.

(Formation of Cathode)

The substrate carrying the light emitting layer formed thereon was placed in a vapor deposition machine and the pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing with a glass substrate was performed, thereby fabricating a light emitting device 1.

(Evaluation of Light Emitting Device)

Voltage was applied to the light emitting device 1, to observe EL emission. At 1000 cd/m$^2$, the driving voltage was 6.1 [V], the light emission efficiency was 76.5 [cd/A], and the chromaticity coordinate (x, y) was (0.30, 0.64). The current value was set so that the initial luminance was 28000 cd/m$^2$, then, the device was driven at constant current, and the luminance half life was measured, to find a time of 7.3 hours.

<Example 2> Fabrication and Evaluation of Light Emitting Device 2

A light emitting device 2 was fabricated in the same manner as in Example 1, excepting that a xylene solution containing the polymer compound P1 and the compound G1 dissolved (0.6 wt %, polymer compound P1/compound G1=70 wt %/30 wt %) was used instead of the xylene solution containing the polymer compound P1 and the compound G1 dissolved (0.6 wt %, polymer compound P1/compound G1=80 wt %/20 wt %), in Example 1.

(Evaluation of Light Emitting Device)

Voltage was applied to the light emitting device 2, to observe EL emission. At 1000 cd/m$^e$, the driving voltage was 5.7 [V], the light emission efficiency was 74.0 [cd/A], and the chromaticity coordinate (x, y) was (0.30, 0.64). The current value was set so that the initial luminance was 28000 cd/m$^2$, then, the device was driven at constant current, and the luminance half life was measured, to find a time of 8.5 hours.

<Example 3> Fabrication and Evaluation of Light Emitting Device 3

A light emitting device 3 was fabricated in the same manner as in Example 1, excepting that a xylene solution containing the polymer compound P1 and the compound G1 dissolved (0.6 wt %, polymer compound P1/compound G1=60 wt %/40 wt %) was used instead of the xylene solution containing the polymer compound P1 and the compound G1 dissolved (0.6 wt %, polymer compound P1/compound G1=80 wt %/20 wt %), in Example 1.

(Evaluation of Light Emitting Device)

Voltage was applied to the light emitting device 3, to observe EL emission. At 1000 cd/m$^2$, the driving voltage was 5.7 [V], the light emission efficiency was 70.2 [cd/A], and the chromaticity coordinate (x, y) was (0.30, 0.64). The current value was set so that the initial luminance was 28000 cd/m$^2$, then, the device was driven at constant current, and the luminance half life was measured, to find a time of 9.6 hours.

<Comparative Example 1> Fabrication and Evaluation of Light Emitting Device C1

A light emitting device C1 was fabricated in the same manner as in Example 1, excepting that a xylene solution containing only the polymer compound P1 dissolved (0.6 wt %) was used instead of the xylene solution containing the polymer compound P1 and the compound G1 dissolved (0.6 wt %, polymer compound P1/compound G1=80 wt %/20 wt %), in Example 1.

(Evaluation of Light Emitting Device)

Voltage was applied to the light emitting device C1, to observe EL emission. At 1000 cd/m$^2$, the driving voltage was 6.1 [V], the light emission efficiency was 82.7 [cd/A], and the chromaticity coordinate (x, y) was (0.30, 0.64). The current value was set so that the initial luminance was 28000 cd/m, then, the device was driven at constant current, and the luminance half life was measured, to find a time of 5.2 hours.

TABLE 3

| | formation of hole transporting layer | formation of light emitting layer | luminance half life (hr) |
|---|---|---|---|
| light emitting device 1 | polymer compound P1 (80 wt %)/ compound G1 (20 wt %) | polymer compound P2 (70 wt %)/ compound G1 (30 wt %) | 7.3 |
| light emitting device 2 | polymer compound P1 (70 wt %)/ compound G1 (30 wt %) | polymer compound P2 (70 wt %)/ compound G1 (30 wt %) | 8.5 |
| light emitting device 3 | polymer compound P1 (60 wt %)/ compound G1 (40 wt %) | polymer compound P2 (70 wt %)/ compound G1 (30 wt %) | 9.6 |
| light emitting device C1 | polymer compound P1 (100 wt %) | polymer compound P2 (70 wt %)/ compound G1 (30 wt %) | 5.2 |

<Example 4> Fabrication and Evaluation of Light Emitting Device 4

(Formation of Anode and Hole Injection Layer)

A glass substrate was attached with an ITO film with a thickness of 45 nm by a sputtering method, to form an anode. On the anode, a polythiophene-sulfonic acid type hole injection agent AQ-1200 (manufactured by Plextronics) was spin-coated to form a film with a thickness of 35 nm, and the film was heated on a hot plate at 170° C. for 15 minutes under an air atmosphere, thereby forming a hole injection layer.

(Formation of Hole Transporting Layer)

The polymer compound P1 and the compound G2 (polymer compound P1/compound G2=85 wt %/15 wt %) were dissolved at a concentration of 0.5 wt % in chlorobenzene. The resultant chlorobenzene solution was spin-coated on the hole injection layer to form a film with a thickness of 20 nm, and the film was heated on a hot plate at 180° C. for 60 minutes under a nitrogen gas atmosphere, thereby forming a hole transporting layer. By heating on a hot plate at 180° C. for 60 minutes, the polymer compound P1 becomes a crosslinked body of the polymer compound P1.
(Formation of Light Emitting Layer)

2,8-di(9H-carbazol-9-yl)dibenzo[b,d]thiophene (DCzDBT) (manufactured by Luminescence Technology Corp) and the compound G2 (DCzDBT/compound G2=70 wt %/30 wt %) were dissolved at a concentration of 2.0 wt % in chlorobenzene. The resultant chlorobenzene solution was spin-coated on the hole transporting layer to form a film with a thickness of 60 nm, and the film was heated 130° C. for 10 minutes under a nitrogen gas atmosphere, thereby forming a light emitting layer.

[Chemical formula 106]

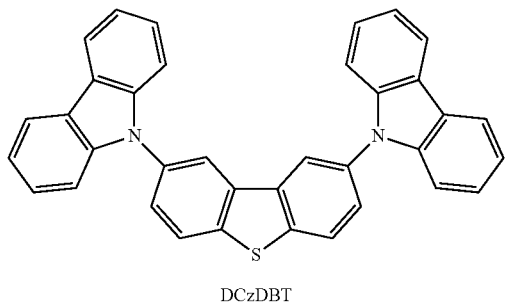

DCzDBT (Formation of Electron Transporting Layer)

The polymer compound P4 was dissolved at a concentration of 0.25 wt % in 2,2,3,3,4,4,5,5-octafluoro-1-pentanol. The resultant 2,2,3,3,4,4,5,5-octafluoro-1-pentanol solution was spin-coated on the light emitting layer to form a film with a thickness of 10 nm, and the film was heated at 130° C. for 10 minutes under a nitrogen gas atmosphere, thereby forming an electron transporting layer.
(Formation of Cathode)

The substrate carrying the electron transporting layer formed thereon was placed in a vapor deposition machine, and the pressured was reduced to $1.0\times10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing with a glass substrate was performed, thereby fabricating a light emitting device 4.
(Evaluation of Light Emitting Device)

Voltage was applied to the light emitting device 4, to observe EL emission. At 1000 cd/m, the driving voltage was 6.1 [V], the light emission efficiency was 3.5 [cd/A], and the chromaticity coordinate (x, y) was (0.19, 0.40). The current value was set so that the initial luminance was 400 cd/m, then, the device was driven at constant current, and the luminance half life was measured, to find a time of 94.1 hours.

<Example 5> Fabrication and Evaluation of Light Emitting Device 5

A light emitting device 5 was fabricated in the same manner as in Example 4, excepting that a chlorobenzene solution containing the polymer compound P1 and the compound G2 dissolved (0.5 wt %, polymer compound P1/compound G2=70 wt %/30 wt %) was used instead of the chlorobenzene solution containing the polymer compound P1 and the compound G2 dissolved (0.5 wt %, polymer compound P1/compound G2=85 wt %/15 wt %), in Example 4.
(Evaluation of Light Emitting Device)

Voltage was applied to the light emitting device 5, to observe EL emission. At 1000 cd/m$^2$, the driving voltage was 5.9 [V], the light emission efficiency was 3.5 [cd/A], and the chromaticity coordinate (x, y) was (0.19, 0.39). The current value was set so that the initial luminance was 400 cd/m$^2$, then, the device was driven at constant current, and the luminance half life was measured, to find a time of 45.4 hours.

<Comparative Example 2> Fabrication and Evaluation of Light Emitting Device C2

A light emitting device C2 was fabricated in the same manner as in Example 4, excepting that a chlorobenzene solution containing only the polymer compound P1 dissolved (0.5 wt %) was used instead of the chlorobenzene solution containing the polymer compound P1 and the compound G2 dissolved (0.5 wt %, polymer compound P1/compound G2=85 wt %/15 wt %), in Example 4.
(Evaluation of Light Emitting Device)

Voltage was applied to the light emitting device C2, to observe EL emission. At 1000 cd/m, the driving voltage was 7.6 [V], the light emission efficiency was 1.4 [cd/A], and the chromaticity coordinate (x, y) was (0.19, 0.40). The current value was set so that the initial luminance was 400 cd/m$^2$, then, the device was driven at constant current, and the luminance half life was measured, to find a time of 2.7 hours.

TABLE 4

| | formation of hole transporting layer | formation of light emitting layer | luminance half life (hr) |
|---|---|---|---|
| light emitting device 4 | polymer compound P1 (85 wt. %)/ compound G2 (15 wt %) | DCzDBT (70 wt %)/ compound G2 (30 wt %) | 94.1 |
| light emitting device 5 | polymer compound P1 (70 wt %)/ compound G2 (30 wt %) | DCzDBT (70 wt %)/ compound G2 (30 wt %) | 45.4 |
| light emitting device C2 | polymer compound P1 (100 wt %) | DCzDBT (70 wt %)/ compound G2 (30 wt %) | 2.7 |

<Example 6> Fabrication and Evaluation of Light Emitting Device 6

A light emitting device 6 was fabricated in the same manner as in Example 4, excepting that a chlorobenzene solution containing the polymer compound P1 and the compound G2 dissolved (0.5 wt %, polymer compound P1/compound G2=70 wt %/30 wt %) was used instead of the chlorobenzene solution containing the polymer compound P1 and the compound G2 dissolved (0.5 wt %, polymer compound P1/compound G2=85 wt %/15 wt %), and further, a chlorobenzene solution containing DCzDBT, the compound G2, the compound G1 and the compound G3 dissolved (2.0 wt %, DCzDBT/compound G2/compound G1/compound G3=69 wt %/30 wt %/0.6 wt %/0.4 wt %)

was used instead of the chlorobenzene solution containing DCzDBT and the compound G2 dissolved (2.0 wt %, DCzDBT/compound G2=70 wt %/30 wt %), in Example 4.
(Evaluation of Light Emitting Device)

Voltage was applied to the light emitting device 6, to observe EL emission. At 1000 cd/m², the driving voltage was 8.5 [V], the light emission efficiency was 4.5 [cd/A], and the chromaticity coordinate (x, y) was (0.26, 0.41). The current value was set so that the initial luminance was 1000 cd/m², then, the device was driven at constant current, and the luminance half life was measured, to find a time of 21.8 hours.

<Example 7> Fabrication and Evaluation of Light Emitting Device 7

A light emitting device 7 was fabricated in the same manner as in Example 4, excepting that a chlorobenzene solution containing the polymer compound P1, the compound G1 and the compound G3 dissolved (0.5 wt %, polymer compound P1/compound G1/compound G3=95 wt %/3 wt %/2 wt %) was used instead of the chlorobenzene solution containing the polymer compound P1 and the compound G2 dissolved (0.5 wt %, polymer compound P1/compound G2=85 wt %/15 wt %), and further, a chlorobenzene solution containing DCzDBT, the compound G2, the compound G1 and the compound G3 dissolved (2.0 wt %, DCzDBT/compound G2/compound G1/compound G3=69 wt %/30 wt %/0.6 wt %/0.4 wt %) was used instead of the chlorobenzene solution containing DCzDBT and the compound G2 dissolved (2.0 wt %, DCzDBT/compound G2=70 wt %/30 wt %), in Example 4.
(Evaluation of Light Emitting Device)

Voltage was applied to the light emitting device 7, to observe EL emission. At 1000 cd/m², the driving voltage was 9.3 [V], the light emission efficiency was 6.2 [cd/A], and the chromaticity coordinate (x, y) was (0.23, 0.40). The current value was set so that the initial luminance was 1000 cd/m¹, then, the device was driven at constant current, and the luminance half life was measured, to find a time of 11.2 hours.

<Example 8> Fabrication and Evaluation of Light Emitting Device 8

A light emitting device 8 was fabricated in the same manner as in Example 4, excepting that a chlorobenzene solution containing the polymer compound P1, the compound G1 and the compound G3 dissolved (0.5 wt %, polymer compound P1/compound G1/compound G3=90 wt %/6 wt %/4 wt %) was used instead of the chlorobenzene solution containing the polymer compound P1 and the compound G2 dissolved (0.5 wt %, polymer compound P1/compound G2=85 wt %/15 wt %), and further, a chlorobenzene solution containing DCzDBT, the compound G2, the compound G1 and the compound G3 dissolved (2.0 wt %, DCzDBT/compound G2/compound G1/compound G3=69 wt %/30 wt %/0.6 wt %/0.4 wt %) was used instead of the chlorobenzene solution containing DCzDBT and the compound G2 dissolved (2.0 wt %, DCzDBT/compound G2=70 wt %/30 wt %), in Example 4.
(Evaluation of Light Emitting Device)

Voltage was applied to the light emitting device 8, to observe EL emission. At 1000 cd/m², the driving voltage was 8.7 [V], the light emission efficiency was 7.1 [cd/A], and the chromaticity coordinate (x, y) was (0.24, 0.40). The current value was set so that the initial luminance was 1000 cd/m², then, the device was driven at constant current, and the luminance half life was measured, to find a time of 14.0 hours.

<Comparative Example 3> Fabrication and Evaluation of Light Emitting Device C3

A light emitting device C3 was fabricated in the same manner as in Example 4, excepting that a chlorobenzene solution containing only the polymer compound P1 dissolved (0.5 wt %) was used instead of the chlorobenzene solution containing the polymer compound P1 and the compound G2 dissolved (0.5 wt %, polymer compound P1/compound G2=85 wt %/15 wt %), and further, a chlorobenzene solution containing DCzDBT, the compound G2, the compound G1 and the compound G3 dissolved (2.0 wt %, DCzDBT/compound G2/compound G1/compound G3=69 wt %/30 wt %/0.6 wt %/0.4 wt %) was used instead of the chlorobenzene solution containing DCzDBT and the compound G2 dissolved (2.0 wt %, DCzDBT/compound G2=70 wt %/30 wt %), in Example 4.
(Evaluation of Light Emitting Device)

Voltage was applied to the light emitting device C3, to observe EL emission. At 1000 cd/m², the driving voltage was 10.4 [V], the light emission efficiency was 3.8 [cd/A], and the chromaticity coordinate (x, y) was (0.23, 0.40). The current value was set so that the initial luminance was 1000 cd/m², then, the device was driven at constant current, and the luminance half life was measured, to find a time of 2.6 hours.

TABLE 5

| | formation of hole transporting layer | formation of light emitting layer | luminance half life (hr) |
|---|---|---|---|
| light emitting device 6 | polymer compound P1 (70 wt %)/ compound G2 (30 wt %) | DCzDBT (69 wt %)/ compound G2 (30 wt %)/ compound G1 (0.6 wt %)/ compound G3 (0.4 wt %) | 21.8 |
| light emitting device 7 | polymer compound P1 (95 wt %)/ compound G1 (3 wt %)/ compound G3 (2 wt %) | DCzDBT (69 wt %)/ compound G2 (30 wt %)/ compound G1 (0.6 wt %)/ compound G3 (0.4 wt %) | 11.2 |
| light emitting device 8 | polymer compound P1 (90 wt %)/ compound G1 (6 wt %)/ compound G3 (4 wt %) | DCzDBT (69 wt %)/ compound G2 (30 wt %)/ compound G1 (0.6 wt %)/ compound G3 (0.4 wt %) | 14.0 |
| light emitting device C3 | polymer compound P1 (100 wt %) | DCzDBT (69 wt %)/ compound G2 (30 wt %)/ compound G1 (0.6 wt %)/ compound G3 (0.4 wt %) | 2.6 |

INDUSTRIAL APPLICABILITY

The present invention can provide a light emitting device excellent in luminance life.

The invention claimed is:

1. A light emitting device comprising
   an anode,
   a cathode,
   a first organic layer disposed between the anode and the cathode and
   a second organic layer disposed between the anode and the first organic layer, wherein
   the first organic layer is a layer comprising one or more phosphorescent compounds and a compound represented by the formula (H-1),
   the second organic layer is a layer comprising one or more phosphorescent compounds and a crosslinked body of a crosslinkable material, and
   at least one phosphorescent compound contained in the first organic layer and at least one phosphorescent compound contained in the second organic layer are the same phosphorescent compound represented by the formula (1-B),

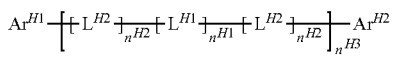
(H-1)

wherein
   $Ar^{H1}$ and $Ar^{H2}$ each independently represent an aryl group or a monovalent heterocyclic group and these groups each optionally have a substituent,
   $n^{H1}$ and $n^{H2}$ each independently represent 0 or 1, and when a plurality of $n^{H1}$ are present, they may be the same or different, and the plurality of $n^{H2}$ may be the same or different,
   $n^{H3}$ represents an integer of 0 or more,
   $L^{H1}$ represents an arylene group, a divalent heterocyclic group or a group represented by $—[C(R^{H11})_2]n^{H11}-$ and these groups each optionally have a substituent, and when a plurality of $L^{H1}$ are present, they may be the same or different, and $n^{H11}$ represents an integer of 1 to 10, and $R^{H11}$ represents a hydrogen atom, an alkyl group, a cycloalkyl group, an alkoxy group, a cycloalkoxy group, an aryl group or a monovalent heterocyclic group and these groups each optionally have a substituent, and the plurality of $R^{H11}$ may be the same or different and may be combined together to form a ring together with the carbon atoms to which they are attached, and
   $L^{H2}$ represents a group represented by $—N(-L^{H21}-R^{H21})—$ and when a plurality of $L^{H2}$ are present, they may be the same or different, and $L^{H21}$ represents a single bond, an arylene group or a divalent heterocyclic group and these groups each optionally have a substituent, and $R^{H21}$ represents a hydrogen atom, an alkyl group, a cycloalkyl group, an aryl group or a monovalent heterocyclic group and these groups each optionally have a substituent;

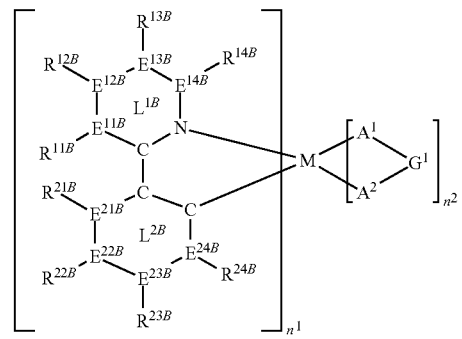
(1-B)

wherein
M represents a ruthenium atom, a rhodium atom, a palladium atom, an iridium atom or a platinum atom,
$n^1$ represents an integer of 1 or more, $n^2$ represents an integer of 0 or more, and $n^1+n^2$ is 2 or 3, and $n^1+n^2$ is 3 when M is a ruthenium atom, a rhodium atom or an iridium atom, while $n^1+n^2$ is 2 when M is a palladium atom or a platinum atom,
$E^{11B}$, $E^{12B}$, $E^{13B}$ and $E^{14B}$ represent a carbon atom, or either $E^{11B}$ or $E^{13B}$ represents a nitrogen atom and $E^{12B}$, $E^{14B}$ and the other of $E^{11B}$ or $E^{13B}$ represent a carbon atom, and when a plurality of $E^{11B}$ and $E^{13B}$ are present, they may be the same or different at each occurrence, and $R^{11B}$ is not present when $E^{11B}$ is a nitrogen atom, and $R^{13B}$ is not present when $E^{13B}$ is a nitrogen atom,
$E^{21B}$, $E^{22B}$, $E^{23B}$ and $E^{24B}$ represent a carbon atom, or one selected from among $E^{21B}$, $E^{22B}$, $E^{23B}$ and $E^{24B}$ represents a nitrogen atom and the other three represent a carbon atom, or $E^{21B}$ and $E^{23B}$ represent a nitrogen atom and $E^{22B}$ and $E^{24B}$ represent a carbon atom, or $E^{22B}$ and $E^{24B}$ represent a nitrogen atom and $E^{21B}$ and $E^{23B}$ represent a carbon atom, and when a plurality of $E^{21B}$, $E^{22B}$, $E^{23B}$ and $E^{24B}$ are present, they may be the same or different at each occurrence, and $R^{21B}$ is not present when $E^{21B}$ is a nitrogen atom, $R^{22B}$ is not present when $E^{22B}$ is a nitrogen atom, $R^{23B}$ is not present when $E^{23B}$ is a nitrogen atom, and $R^{24B}$ is not present when $E^{24B}$ is a nitrogen atom,
$R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group or a halogen atom and these groups each optionally have a substituent, and when a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence, and $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ each may be combined together to form a ring together with the atoms to which they are attached, and at least one selected from the group consisting of $R^{11B}$, $R^{12B}$, $R^{13B}$, $R^{14B}$, $R^{21B}$, $R^{22B}$, $R^{23B}$ and $R^{24B}$ is a group represented by the formula (2),
the ring $L^{1B}$ represents a pyridine ring or a pyrimidine ring,
the ring $L^{2B}$ represents a benzene ring, a pyridine ring or a pyrimidine ring, and
$A^1$-$G^1$-$A^2$ represents an anionic bidentate ligand, and $A^1$ and $A^2$ each independently represent a carbon atom, an oxygen atom or a nitrogen atom and these atoms each may be an atom constituting a ring, and $G^1$ represents a single bond or an atomic group constituting the bidentate ligand together with $A^1$ and $A^2$, and when a plurality of $A^1$-$G^1$-$A^2$ are present, they may be the same or different; and $$—R^2 \quad (2),$$

wherein $R^2$ represents an aryl group, a monovalent heterocyclic group or a substituted amino group and these groups each optionally have a substituent.

2. The light emitting device according to claim 1, wherein the group represented by the formula (2) is a group represented by the formula (D-A) or a group represented by the formula (D-B):

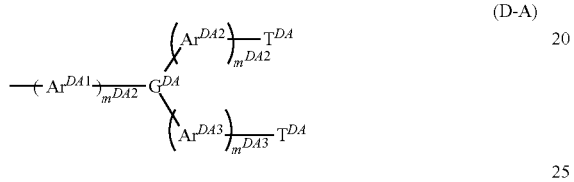
(D-A)

wherein
$m^{DA1}$, $m^{DA2}$ and $m^{DA3}$ each independently represent an integer of 0 or more,
$G^{DA}$ represents a nitrogen atom, an aromatic hydrocarbon group or a heterocyclic group and these groups each optionally have a substituent,
$Ar^{DA1}$, $Ar^{DA2}$ and $Ar^{DA3}$ each independently represent an arylene group or a divalent heterocyclic group and these groups each optionally have a substituent, and when a plurality of $Ar^{DA1}$, $Ar^{DA2}$ and $Ar^{DA3}$ are present, they may be the same or different at each occurrence,
$T^{DA}$ represents an aryl group or a monovalent heterocyclic group and these groups each optionally have a substituent, and the plurality of $T^{DA}$ may be the same or different:

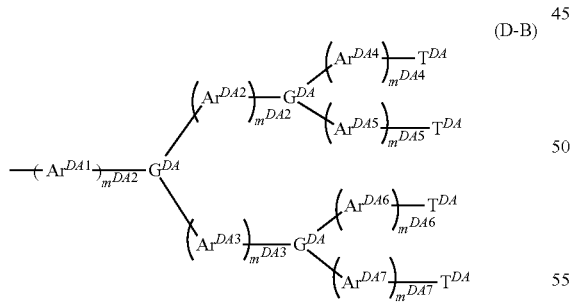
(D-B)

wherein
$m^{DA1}$, $m^{DA2}$, $m^{DA3}$, $m^{DA4}$, $m^{DA5}$, $m^{DA6}$ and $m^{DA7}$ each independently represent an integer of 0 or more,
$G^{DA1}$, $G^{DA2}$ and $G^{DA3}$ each independently represent a nitrogen atom, an aromatic hydrocarbon group or a heterocyclic group and these groups each optionally have a substituent, and $m^{DA2}$ is an integer of 1 or more when $G^{DA1}$ and $G^{DA2}$ are each a nitrogen atom, $m^{DA3}$ is an integer of 1 or more when $G^{DA1}$ and $G^{DA3}$ are each a nitrogen atom, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group and these groups each optionally have a substituent, and when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence, and $T^{DA}$ represents an aryl group or a monovalent heterocyclic group and these groups each optionally have a substituent, and the plurality of $T^{DA}$ may be the same or different.

3. The light emitting device according to claim 1, wherein the crosslinkable material is a polymer compound comprising a crosslinkable constitutional unit having at least one crosslinkable group selected from Group A of crosslinkable group:

(Group A of crosslinkable group)

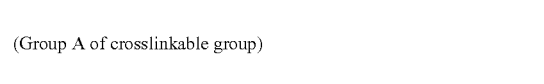
(XL-1)

(XL-2)

(XL-3)

(XL-4)

(XL-5)

(XL-6)

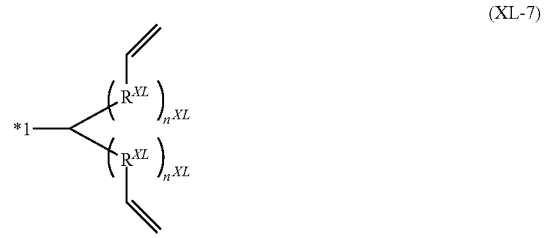
(XL-7)

-continued (XL-8)
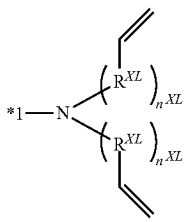

(XL-9)
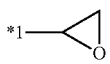

(XL-10)

(XL-11)

(XL-12)
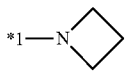

(XL-13)
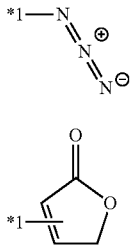

(XL-14)
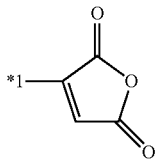

(XL-15)

(XL-16)
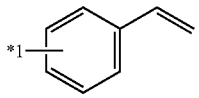

(XL-17)
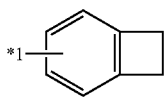

wherein $R^{XL}$ represents a methylene group, an oxygen atom or a sulfur group, and $n^{XL}$ represents an integer of 0 to 5, and when a plurality of $R^{XL}$ are present, they may be the same or different, and when a plurality of $n^{XL}$ are present, they may be the same or different, and *1 represents a binding site, and these crosslinkable groups each optionally have a substituent.

4. The light emitting device according to claim 3, wherein the crosslinkable constitutional unit is a constitutional unit represented by the formula (3) or a constitutional unit represented by the formula (4):

(3)
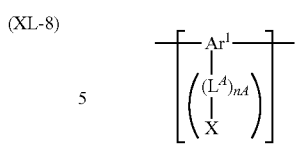

wherein
nA represents an integer of 0 to 5, and n represents 1 or 2,
$Ar^1$ represents an aromatic hydrocarbon group or a heterocyclic group and these groups each optionally have a substituent,
$L^A$ represents an alkylene group, a cycloalkylene group, an arylene group, a divalent heterocyclic group, a group represented by —NR'—, an oxygen atom or a sulfur atom and these groups each optionally have a substituent, and R' represents a hydrogen atom, an alkyl group, a cycloalkyl group, an aryl group or a monovalent heterocyclic group and these groups each optionally have a substituent, and when a plurality of $L^A$ are present, they may be the same or different, and
X represents a crosslinkable group selected from Group A of crosslinkable group, and when a plurality of X are present, they may be the same or different:

(4)
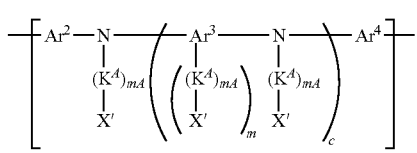

wherein
mA represents an integer of 0 to 5, m represents an integer of 1 to 4, and c represents 0 or 1, and when a plurality of mA are present, they may be the same or different,
$Ar^3$ represents an aromatic hydrocarbon group, a heterocyclic group or a group in which at least one aromatic hydrocarbon ring and at least one heterocyclic ring are bonded directly to each other, and these groups each optionally have a substituent,
$Ar^2$ and $Ar^4$ each independently represent an arylene group or a divalent heterocyclic group and these groups each optionally have a substituent,
each of $Ar^2$, $Ar^3$ and $Ar^4$ may be bonded directly or via an oxygen atom or a sulfur atom to a group that is different from that group and that is attached to the nitrogen atom to which that group is attached, thereby forming a ring,
$K^A$ represents an alkylene group, a cycloalkylene group, an arylene group, a divalent heterocyclic group, a group represented by —NR"—, an oxygen atom or a sulfur atom and these groups each optionally have a substituent, and R" represents a hydrogen atom, an alkyl group, a cycloalkyl group, an aryl group or a monovalent heterocyclic group and these groups each optionally have a substituent, and when a plurality of $K^A$ are present, they may be the same or different, and
X' represents a crosslinkable group selected from Group A of crosslinkable group, a hydrogen atom, an alkyl group, a cycloalkyl group, an aryl group or a monovalent heterocyclic group and these groups each optionally have a substituent, and at least one X' is a crosslinkable group selected from Group A of crosslinkable group.

5. The light emitting device according to claim 1, wherein the phosphorescent compound represented by the formula (1-B) is a phosphorescent compound represented by the formula (1-B1) or (1-B2):

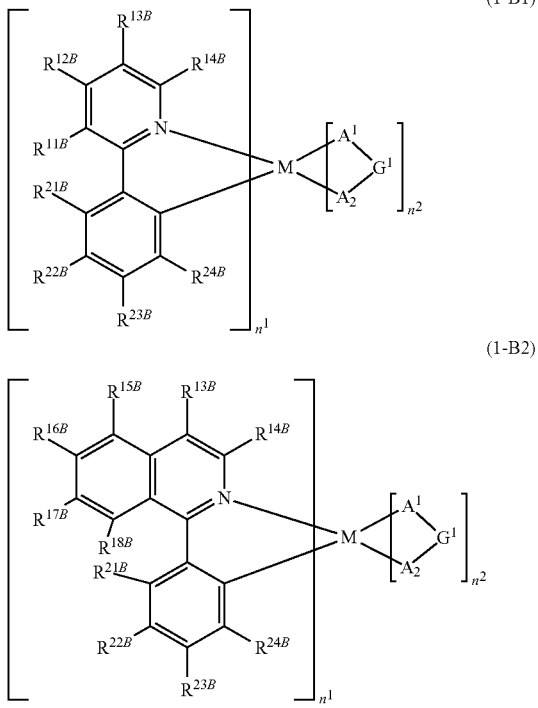

(1-B1)

(1-B2)

wherein

M, $n^1$, $n^2$ and $A^1$-$G^1$-$A^2$ represent the same meaning as described above, $R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group or a halogen atom and these groups each optionally have a substituent, and when a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence, and $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ each may be combined together to form a ring together with the atoms to which they are attached, and at least one selected from the group consisting of $R^{11B}$, $R^{12B}$, $R^{13B}$, $R^{14B}$, $R^{21B}$, $R^{22B}$, $R^{23B}$ and $R^{24B}$ is a group represented by the formula (2), $R^{15B}$, $R^{16B}$, $R^{17B}$ and $R^{18B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom and these groups each optionally have a substituent, and when a plurality of $R^{15B}$, $R^{16B}$, $R^{17B}$ and $R^{18B}$ are present, they may be the same or different at each occurrence, and $R^{13B}$ and $R^{15B}$, $R^{15B}$ and $R^{16B}$, $R^{16B}$ and $R^{17B}$, $R^{17B}$ and $R^{18B}$, and $R^{18B}$ and $R^{21B}$ each may be combined together to form a ring together with the atoms to which they are attached.

6. The light emitting device according to claim 1, wherein $n^{H1}$ in the formula (H-1) is 1, and $n^{H3}$ in the formula (H-1) is 1.

7. The light emitting device according to claim 1, wherein the phosphorescent compound represented by the formula (1-B) is a phosphorescent compound represented by (1-B3):

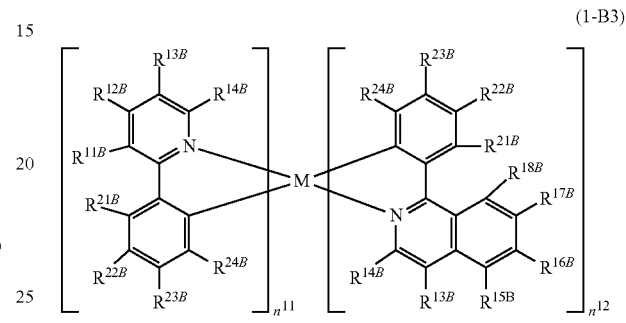

(1-B3)

wherein

M represents the same meaning as described above, $R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group or a halogen atom and these groups each optionally have a substituent, and when a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence, and $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ each may be combined together to form a ring together with the atoms to which they are attached, and at least one selected from the group consisting of $R^{11B}$, $R^{12B}$, $R^{13B}$, $R^{14B}$, $R^{21B}$, $R^{22B}$, $R^{23B}$ and $R^{24B}$ is a group represented by the formula (2), $n^{11}$ and $n^{12}$ each independently represent an integer of 1 or more, and $n^{11}+n^{12}$ is 2 or 3, and $n^{11}+n^{12}$ is 3 when M is a ruthenium atom, a rhodium atom or an iridium atom, while $n^{11}+n^{12}$ is 2 when M is a palladium atom or a platinum atom, $R^{15B}$, $R^{16B}$, $R^{17B}$ and $R^{18B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom and these groups each optionally have a substituent, and when a plurality of $R^{15B}$, $R^{16B}$, $R^{17B}$ and $R^{18B}$ are present, they may be the same or different at each occurrence, and $R^{13B}$ and $R^{15B}$, $R^{15B}$ and $R^{16B}$, $R^{16B}$ and $R^{17B}$, $R^{17B}$ and $R^{18B}$, and $R^{18B}$ and $R^{21B}$ each may be combined together to form a ring together with the atoms to which they are attached.

* * * * *